US011752163B2

(12) United States Patent
Dasseux et al.

(10) Patent No.: US 11,752,163 B2
(45) Date of Patent: Sep. 12, 2023

(54) CER-001 THERAPY FOR TREATING KIDNEY DISEASE

(71) Applicant: ABIONYX PHARMA SA, Balma (FR)

(72) Inventors: Jean-Louis Dasseux, Toulouse (FR); Laura Calabresi, Milan (IT); Cyrille Tupin, Castelmaurou (FR); Ronald Barbaras, Seilh (FR); Constance Peyrottes, Le Castera (FR)

(73) Assignee: Abionyx Pharma SA, Balma (FR)

( * ) Notice: Subject to any disclaimer, the term of this patent is extended or adjusted under 35 U.S.C. 154(b) by 33 days.

(21) Appl. No.: 17/231,659

(22) Filed: Apr. 15, 2021

(65) Prior Publication Data
US 2021/0322448 A1 Oct. 21, 2021

Related U.S. Application Data

(60) Provisional application No. 63/092,072, filed on Oct. 15, 2020, provisional application No. 63/011,048, filed on Apr. 16, 2020.

(30) Foreign Application Priority Data

Jan. 7, 2021 (WO) ................. PCT/IB2021/00021

(51) Int. Cl.
A61K 38/00 (2006.01)
C07K 14/775 (2006.01)
A61P 13/12 (2006.01)
A61K 31/688 (2006.01)
A61K 47/24 (2006.01)

(52) U.S. Cl.
CPC ............ A61K 31/688 (2013.01); A61K 47/24 (2013.01); C07K 14/775 (2013.01); *A61K 38/00* (2013.01)

(58) Field of Classification Search
CPC .... C07K 14/775; A61K 38/00; A61K 9/0019; A61K 38/1709; A61P 13/12
See application file for complete search history.

(56) References Cited

U.S. PATENT DOCUMENTS

| 6,953,840 | B2 | 10/2005 | Zhu et al. |
| 10,517,924 | B2 | 12/2019 | Thaxton et al. |
| 2005/0080013 | A1 | 4/2005 | Dasseux |
| 2014/0213501 | A1 | 7/2014 | Dasseux |
| 2015/0316566 | A1* | 11/2015 | Dasseux ............ C12Q 1/6883 435/6.12 |
| 2016/0235672 | A1 | 8/2016 | Kontush et al. |
| 2018/0203025 | A1 | 7/2018 | Dasseux |

FOREIGN PATENT DOCUMENTS

| WO | 95/34289 A1 | 12/1995 |
| WO | 2004/010939 A2 | 2/2004 |
| WO | 2006/100567 A1 | 9/2006 |
| WO | 2010/093918 A1 | 8/2010 |
| WO | 2012/109162 A1 | 8/2012 |
| WO | 2012/135046 A1 | 10/2012 |
| WO | 2018/022511 A1 | 1/2018 |
| WO | 2018/019911 A1 | 2/2018 |
| WO | 2018/029505 A1 | 2/2018 |
| WO | 2021/048268 A1 | 3/2021 |
| WO | 2021/209808 A1 | 10/2021 |
| WO | 2021/209822 A1 | 10/2021 |
| WO | 2021/209823 A1 | 10/2021 |

OTHER PUBLICATIONS

Kidney Diseases from MedlinePlus, https://medlineplus.gov/kidneydiseases.html, pp. 1-11. Last updated Nov. 18, 2020. (Year : 2020).*
Renal Pelvic and Ureteral Cancers from Merck Manual, pp. 1-3. Modified Sep. 2022. (Year: 2022).*
Acquired Renal Cysts from Merck Manual, p. 1. Modified Sep. 2022. (Year: 2502).*
Urinary Calculi from Merck Manual, pp. 1-8. Modified Sep. 2022. (Year: 2022).*
International Search Report and Written Opinion dated May 14, 2021 corresponding to International Application No. PCT/IB2021/000021.
International Search Report and Written Opinion dated Aug. 13, 2021 corresponding to International Application No. PCT/IB2021/000282.
International Search Report and Written Opinion dated Jul. 29, 2021 corresponding to International Application No. PCT/IB2021/000283.
Anonymous, 2021 "ABIONYX Announces Positive Clinical Results From CER-001 in an Ultrarare Kidney Disease", Annals of Internal Medicine.
Anonymous, 2020 "ABIONYX initiates a Phase 2a clinical trial with CER-001 in septic patients at high risk of developing Acute Kidney Injury".
Anonymous, 2021, "CER-001 helps restore kidney function and vision for patient with rare genetic kidney disease" EurekAlert, all pages.
Barbaras 2015, "Non-clinical development of CER-001" Frontiers in Pharmacology, 6(220): 1-7.
Genga et al., 2017 "Two-year follow-up of patients with septic shock presenting with low HDL: the effect upon acute kidney injury, death and estimated glomerular filtration rate" The Association for the Publication of the Journal of Internal Medicine 281: 518-529.

(Continued)

*Primary Examiner* — Julie Ha
(74) *Attorney, Agent, or Firm* — Biospark Intellectual Property Law

(57) ABSTRACT

Disclosed herein is the use of CER-001, a negatively charged lipoprotein complex which comprises recombinant human apolipoprotein A-I (ApoA-I), sphingomyelin (SM), and 1,2-dihexadecanoyl-sn-glycero-3-phospho-(1'-rac-glycerol) (Dipalmitoylphosphatidyl-glycerol; DPPG) for treating kidney diseases, and methods for treating a subject having kidney diseases with CER-001. For example, the kidney disease can be associated with a lecithin cholesterol acyl transferase (LCAT) deficiency.

13 Claims, 22 Drawing Sheets

(56) References Cited

OTHER PUBLICATIONS

Gibson et al. ,2019 "The CSL112-2001 trial: Safety and tolerability of multiple does of CSL112 (apolipoprotein A—I [human]), an intravenous formulation of plasma-derived apolipoprotein A-I, among subjects with moderate renal impairment after acute myocardial infarction", American Heart Journal, 208: 81-90.

Gille et al., 2019 "Moderate Renal Impairment Does Not Impact the Ability of CSL I 12 (Apolipoprotein A-I [Human]) to Enhance Cholestoral Efflux Capacity" American College of Clinical Pharmacology, 59(3): 427-436.

Gordon et al., 2017 "High density lipoproteins are modulators of protease activity: Implications in inflammation, complement activation, and atherothrombosis" Atherosclerosis 259:104-113.

Kaysen, 2009, "Potential restoration of HDL function with apolipoprotein A-I mimetic peptide in end-stage renal disease", Kidney International, 359-361.

Kootte et al., 2014, "Recombinant human apolipoprotein-a-I prebeta-HDL (cer-001) promotes reverse cholesterol transport and reduces carotid wall thickness in patients with genetically-determined low HDL", Atherosclerosis, 235(2): all pages.

Krause et al., 2013 "Reconstitued HDL for the acute treatment of acute coronary syndrome", Current Opinion in Lipidology, 24(6): 480-486.

Liu et al., 2020 "Effect of low high-density lipoprotein levels on mortality of septic patients: A systematic review and meta-analysis of cohort studies" World J Emerg Med, 11(2): 109-116.

McDonald et al., 2003 "Reconstituted High-Density Lipoprotein Attenuates Organ Injury and Adhesion Molecule Expression in a Rodent Model of Endotoxic Shock" Shock 20(6): 551-557.

Morin et al., 2015 "HDL in sepsis—risk factor and therapeutic approach", Frontiers in Pharmacology, 6: 244-249.

Navab et al., 2009 "HDL as a Biomarker, Potential Therapeutic Target, and Therapy" Diabetes 58:2711-2717.

Niyonzima et al., 2015 "Reconstituted High-Density Lipoprotein Attenuates Cholesterol Crystal-Induced Inflammatory Responses by Reducing Complement Activation" J Immunol 195:000-000.

Ossoli et al., 2020, "CER-001 ameliorates lipid profile and kidney disease in a mouse model of familial LCAT deficiency" Metabolism, Clinical and Experimental, 116(9): all pages.

Ossoli et al., 2019, "Remodeling and Catabolism of Cer-001 in Absence of Leaf Enzyme", Atherosclerosis, 287: all pages.

Säemann et al., 2010"The versatility of HDL: a crucial antiinflammatory" Eur J Clin Invest; 40(12):1131-1143.

Smith et al., 2017 "High-Density Lipoprotein Cholesterol Concentraion and Acute Kidney Injury After Cardiac Surgery" Journal of the American Heart Association.

Pavanello et al., 2021 "The HDL mimetic CER-001 remodels plasma lipoproteins and reduces kidney lipid deposits in inherited lecithin:cholestoral acyltransferase deficiency" Journal of Internal Medicine 0; 1-7.

Pajkrt et al., 1996 "Antiinfalmmatory effects of reconstituted high-density lipoprotein during human endotoxemia", Journal of Experimental Medicine, 184(5): 1601-1608.

Remaley et al., 2008 "HDL-replacement therapy: Mechanism of action, types of agents and potential clinical indications", Expert Review of Cardiovascular Therapy, 6(9): 1203-1215.

Sposito et al., 2019 "HDL-Targeted Therapies During Myocardial Infarction", Cardiovascular Drugs and Therapy, 33(3): 371-381.

Van Lenten et al., 2004 "D-4F, an Apolipoprotein A-I Mimetic Peptide, Inhibits the Inflammatory Response Induced by Influenza A Infection of Human Type II Pneumocytes", Circulation, 110(20): 3252-3258.

Takahashi et al., 2013 "Nephrotic Syndrome Caused by Immune-Mediated Acquired LCAT Deficiency" J Am Soc Nephrol 24:1305-1312.

Tanaka et al., 2020 "High-density lipoproteins during sepsis: from bench to bedside" Critical Care 24:134.

Tanaka et al., 2020 "Reconstituted High-density Lipoprotein Therapy Improves Survival in Mouse Models of Sepsis" Anesthesiology 4(132):825-838.

Thiemermann et al., 2003 "High Density Lipoprotein (HDL) Reduces Renal Ischemia/Reperfusion Injury" J Am Soc Nephrol 14:1833-1843.

Tortorici et al., 2019 "Pharmacokinetics and Safety of CSL112 (Apolipoprotein A-I [Human]) in Adults With Moderate Renal Impairment and Normal Renal Function" Clinical Pharmacology in Drug Development 8(5) 628-636.

Wu et al., 2004 "High-density Lipoproteins in Sepsis and Septic Shock: Metabolism, Actions, and Therapeutic Applications" Shock 21 (3):210-221.

Zhou et al., 2020 "High-density lipoprotein cholesterol concentration and acute kidney injury after noncardiac surgery" BMC Nephrology 21:149.

Guo et al., 2013, "High Density Lipoprotein Protects against Polymicrobe-induced Sepsis in Mice" The Journal of Biological Chemistry 288(25): 17947-17953.

Mattana et al., 2003, "Possible role of high density lipoprotein in the progression of glomerulosclerosis" J Med. 34(1-6):81-6.

* cited by examiner

CER-001 THERAPY FOR TREATING KIDNEY DISEASE

1. CROSS-REFERENCE TO RELATED APPLICATIONS

This application claims the priority benefit of U.S. provisional application nos. 63/011,048, filed Apr. 16, 2020, and 63/092,072, filed Oct. 15, 2020, and PCT international application no. PCT/IB2021/000021, filed Jan. 7, 2021, the contents of each which are incorporated herein in their entireties by reference thereto.

2. BACKGROUND

2.1. Kidney Disease

The kidneys are two bean-shaped organs, each about the size of a fist. They are located just below the rib cage, one on each side of the spine. Healthy kidneys filter about a half cup of blood every minute, removing wastes and extra water to make urine. Urine flows from the kidneys to the bladder through two thin tubes of muscle called ureters, one on each side of the bladder, the bladder stores urine. The kidneys, ureters, and bladder are all part of the urinary tract.

Healthy kidneys remove wastes and extra fluid from the body. Kidneys also remove acid that is produced by the cells and maintain a healthy balance of water, salts, and minerals—such as sodium, calcium, phosphorus, and potassium—in the blood. The kidneys also make hormones that help control blood pressure and make red blood cells.

Each kidney is made up of about a million filtering units called nephrons. The nephrons work through a two-step process to filter the blood and return needed substances to your blood and remove waste. Blood circulates through the kidneys many times a day. In a single day, the kidneys filter about 150 quarts of blood. If blood stops flowing into a kidney, part or all of it could die which can lead to kidney failure.

Kidney disease, also known as renal disease and nephropathy, is damage to or disease of a kidney.

2.1.1. Chronic Kidney Disease

Chronic kidney disease (CKD) is a type of kidney disease in which there is gradual loss of kidney function over a period of months to years. CKD can cause other health problems, such as heart disease, stroke, anemia, increased occurrence of infections, low calcium levels, high potassium levels, and high phosphorus levels in the blood, loss of appetite and depression.

CKD has varying levels of seriousness. It usually gets worse over time though treatment has been shown to slow progression. If left untreated, CKD can progress to kidney failure and early cardiovascular disease. When the kidneys stop working, dialysis or kidney transplant is needed for survival, at this stage the disease is known as end-stage renal disease (ESRD).

CDK is extremely difficult to treat when it progresses often necessitating dialysis or kidney transplantation when end-stage renal failure occurs. Therefore, it is necessary to detect glomerular diseases as early as possible and to treat and stop the progression as much as possible after the onset. About 37 million US adults are estimated to have CKD and most are undiagnosed. CKD places a large economic burden to health care systems and severely reduces the quality of life of subjects suffering from it.

2.1.2. Glomerulopathy

Glomerulopathy refers to kidney disease affecting the glomeruli of the nephron in the kidney. The glomerulus is a network of small capillaries known as a tuft, located at the beginning of a nephron in the kidney. The tuft is structurally supported by the mesangium made up of intraglomerular mesangial cells. Blood is filtered across the capillary walls of this tuft through the glomerular filtration barrier, which yields its filtrate of water and soluble substances to a cup-like sac known as Bowman's capsule. The filtrate then enters the renal tubule of the nephron. The glomerulus receives its blood supply from an afferent arteriole of the renal arterial circulation. Unlike most capillary beds, the glomerular capillaries exit into efferent arterioles rather than venules. The resistance of the efferent arterioles causes sufficient hydrostatic pressure within the glomerulus to provide the force for ultrafiltration. The glomerulus and its surrounding Bowman's capsule constitute a renal corpuscle, the basic filtration unit of the kidney.

The glomerulus filtrates blood to produce a glomerular filtrate containing substantially the same components as plasma components of which molecular weight is 10,000 or less. Generally, the filtration is controlled so as not to leak essential substances from blood, especially serum protein, to urine. Glomerulus damage causes the growth of mesangial cells and the expansion of a neighbor extracellular matrix to increase the amount of urinary protein excretion. It is known that the increase of urinary protein excretion further lowers renal function as a result of damage to renal tubules.

Glomerular diseases can include processes that are inflammatory or noninflammatory. Glomerular diseases are a leading cause of CKD.

2.1.3. Diabetic Nephropathy

Diabetic nephropathy (DN), also known as diabetic kidney disease, is the chronic loss of kidney function occurring in those with diabetes mellitus. DN results in protein loss in the urine due to damage to the glomeruli and cause a low serum albumin with resulting generalized body swelling (edema). In subjects with DN, the estimated glomerular filtration rate (eGFR) may progressively fall from a normal of over 90 ml/min/1.73 $m^2$ to less than 15, at which point the subject is considered to have ESKD.

Pathophysiologic abnormalities in DN begin with long-standing poorly controlled blood glucose levels. This is followed by multiple changes in the filtration units of the kidneys, the nephrons. Initially, there is constriction of the efferent arterioles and dilation of afferent arterioles, with resulting glomerular capillary hypertension and hyperfiltration; this gradually changes to hypofiltration over time. Concurrently, there are changes within the glomerulus itself, these include a thickening of the basement membrane, a widening of the slit membranes of the podocytes, an increase in the number of mesangial cells, and an increase in mesangial matrix. This matrix invades the glomerular capillaries and produces deposits called Kimmelstiel-Wilson nodules. The mesangial cells and matrix can progressively expand and consume the entire glomerulus, shutting off filtration.

Diabetic nephropathy is the most common cause of ESKD and is a serious complication that affects approximately one quarter of adults with diabetes in the United States.

2.2. Lecithin Cholesterol Acyl Transferase

Lecithin cholesterol acyl transferase (LCAT) is an enzyme produced by the liver and is the key enzyme in the reverse cholesterol transport (RCT) pathway. The RCT pathway functions to eliminate cholesterol from most extrahepatic tissues and is crucial to maintaining the structure and function of most cells in the body. RCT consists mainly of three steps: (a) cholesterol efflux, i.e., the initial removal of cholesterol from various pools of peripheral cells; (b) cholesterol esterification by the action of lecithin:cholesterol acyltransferase (LCAT), preventing a re-entry of effluxed cholesterol into cells; and (c) uptake of high density lipoprotein (HDL)-cholesterol and cholesteryl esters to liver cells for hydrolysis, then recycling, storage, excretion in bile or catabolism to bile acids.

LCAT circulates in plasma associated with the HDL fraction. LCAT converts cell-derived cholesterol to cholesteryl esters, which are sequestered in HDL destined for removal (see Jonas 2000, Biochim. Biophys. Acta 1529(1-3):245-56). Cholesteryl ester transfer protein CETP) and phospholipid transfer protein (PLTP) contribute to further remodeling of the circulating HDL population. CETP moves cholesteryl esters made by LCAT to other lipoproteins, particularly ApoB-comprising lipoproteins, such as very low density lipoprotein (VLDL) and low density lipoprotein (LDL). PLTP supplies lecithin to HDL. HDL triglycerides are catabolized by the extracellular hepatic triglyceride lipase, and lipoprotein cholesterol is removed by the liver via several mechanisms.

A deficiency of LCAT causes accumulation of unesterified cholesterol in certain body tissues. Cholesterol effluxes from cells as free cholesterol and is transported in HDL as esterified cholesterol. LCAT is the enzyme that esterifies the free cholesterol on HDL to cholesterol ester and allows the maturation of HDL. LCAT deficiency does not allow for HDL maturation resulting in its rapid catabolism of circulating apoA-1 and apoA-2. The remaining form of HDL resembles nascent HDL. Subjects with LCAT deficiency (both full and partial) have low HDL cholesterol.

Familial LCAT deficiency is a rare genetic disorder in which sufferers lack LCAT activity and are of risk of progressive CKD and in some cases renal failure. Fish eye disease is a partial LCAT deficiency in which LCAT cannot esterify, or make the acid into an alkyl, cholesterol in HDL particles. However, LCAT remains active on the cholesterol particles in VLDL and LDL. Fish-eye disease is characterized by abnormalities like visual impairment, plaques of fatty material, and dense opacification. Both the familial LCAT deficiency and Fish-eye disease are autosomal recessive disorders caused by mutations of the LCAT gene located on chromosome 16q22.1.

Currently, there is no specific treatment to correct the LCAT deficiency so therapy is focused on symptom relief. Dialysis may be required for subjects presenting with renal failure, and kidney transplant may be considered. Renal failure is the major cause of morbidity and mortality in complete LCAT deficiency.

New methods for treating subjects with kidney disease, for example subjects with glomerulopathy, e.g., associated with LCAT deficiency, and subjects with diabetic nephropathy, are needed.

3. SUMMARY

The present disclosure provides methods for treating kidney disease with CER-001. CER-001 is a negatively charged lipoprotein complex, and comprises recombinant human ApoA-I, sphingomyelin (SM), and 1,2-dihexadecanoyl-sn-glycero-3-phospho-(1'-rac-glycerol) (Dipalmitoylphosphatidyl-glycerol; DPPG). It mimics natural, nascent discoidal pre-beta HDL, which is the form that HDL particles take prior to acquiring cholesterol.

In one aspect, the present disclosure provides dosing regimens for CER-001 therapy for subjects with kidney disease, for example subjects having glomerulopathy, e.g., associated LCAT deficiency, and subjects having diabetic nephropathy.

The dosing regimens of the disclosure typically entail administering CER-001 to a subject according to an initial "induction" regimen, followed by administering CER-001 to the subject according to a "consolidation" regimen, followed by administering CER-001 to the subject according to a "maintenance" regimen. Alternatively, dosing regimens can entail administering CER-001 to the subject according to a "maintenance" regimen without a preceding "induction" regimen or "consolidation" regimen. As another alternative, dosing regimens can entail administering CER-001 to the subject according to an "induction" regimen followed by a "maintenance" regimen without an intervening "consolidation" regimen.

The induction regimen typically comprises administering multiple doses of CER-001 to the subject with a period of 1 day or greater between each dose. In some embodiments, the induction regimen comprises three or more doses of CER-001. In some embodiments, the induction regimen comprises three doses a week of CER-001. In some embodiments, the induction regimen comprises three doses a week of CER-001 for a period of more than one week e.g., a period of two weeks or greater. In some embodiments the induction regimen comprises three doses a week of CER-001 for a period of three weeks.

The consolidation regimen typically comprises administering multiple doses of CER-001 to the subject on a less frequent basis than during the induction regimen. The consolidation regimen typically comprises administering multiple doses of CER-001 to the subject with a period of 1 day or greater between each dose e.g., 2 days or greater between each dose. In some embodiments, the consolidation regimen comprises two or more doses of CER-001. In some embodiments, the consolidation regimen comprises two doses a week of CER-001. In some embodiments, the consolidation regimen comprises two doses a week of CER-001 for a period of more than one week e.g., a period of two weeks or greater. In some embodiments the consolidation regimen comprises two doses a week of CER-001 for a period of three weeks.

The maintenance regimen typically comprises administering one or more doses of CER-001 to the subject on a less frequent basis than during the consolidation regimen, for example a period of 5 days or greater, e.g., a period of one week, between doses. In certain embodiments, the multiple doses of CER-001 are administered once every week during the maintenance regimen.

In certain aspects, the disclosure provides methods of treating a subject with CER-001 using an induction regimen comprising administering three doses of CER-001 to the subject within one week for three weeks with at least 1 day between each dose followed by a consolidation regimen comprising administering two doses of CER-001 to the subject within one week for three weeks with at least 2 days between each dose followed by a maintenance regimen comprising administering one dose of CER-001 to the subject every week.

In certain aspects, the disclosure provides methods of treating a subject with CER-001 in accordance with a dosage regimen described herein. In some embodiments, the CER-001 is diluted with saline before intravenous administration such as intravenous infusion using an infusion pump. In certain embodiments the dose of CER-001 is based on subject weight, for example 10 mg/kg by intravenous infusion.

In certain aspects, the disclosure provides methods of treating a subject having kidney disease with CER-001 according to a dosage regimen comprising:

3 doses per week for 3 weeks (induction regimen) followed by 2 doses per week for 3 weeks (consolidation regimen), followed by 1 dose per week until the end of treatment (maintenance regimen).

In certain aspects, an antihistamine (e.g., dexchlorpheniramine, hydroxyzine, diphenhydramine, cetirizine, fexofenadine, or loratadine) can be administered before administration of CER-001. The antihistamine can reduce the likelihood of allergic reactions.

The subject treated according to the dosing regimens of the disclosure can be any subject suffering from kidney disease, for example a subject suffering glomerulopathy associated with LCAT deficiency or a subject having diabetic nephropathy. In some embodiments, the subject treated according to the dosing regimens of the disclosure has glomerulopathy associated with LCAT deficiency (e.g., an LCAT deficiency due to an LCAT mutation or an LCAT deficiency which is an acquired LCAT deficiency). The LCAT deficiency may be full LCAT deficiency or partial LCAT deficiency. In some embodiments, the subject treated according to the dosing regimens of the disclosure has diabetic nephropathy. In some embodiments, the subject has CKD. In some embodiments, the subject has hepatorenal syndrome (HRS) or is at risk of HRS.

4. BRIEF DESCRIPTION OF THE FIGURES

FIGS. 16A-16D are graphs illustrating the profiles of lipoproteins separated by FPLC derived from plasma of LCAT -/- mice at basal condition (FIG. 16A), at the end of 4-weeks of LpX injection (FIG. 16B), and after saline (FIG. 16C) or CER-001 treatment (FIG. 16D) as described in Example 4. Phospholipid (PL), Total Cholesterol (TC), and Unesterified Cholesterol (UC) were measured in collected plasma fractions.

Figure 17A:
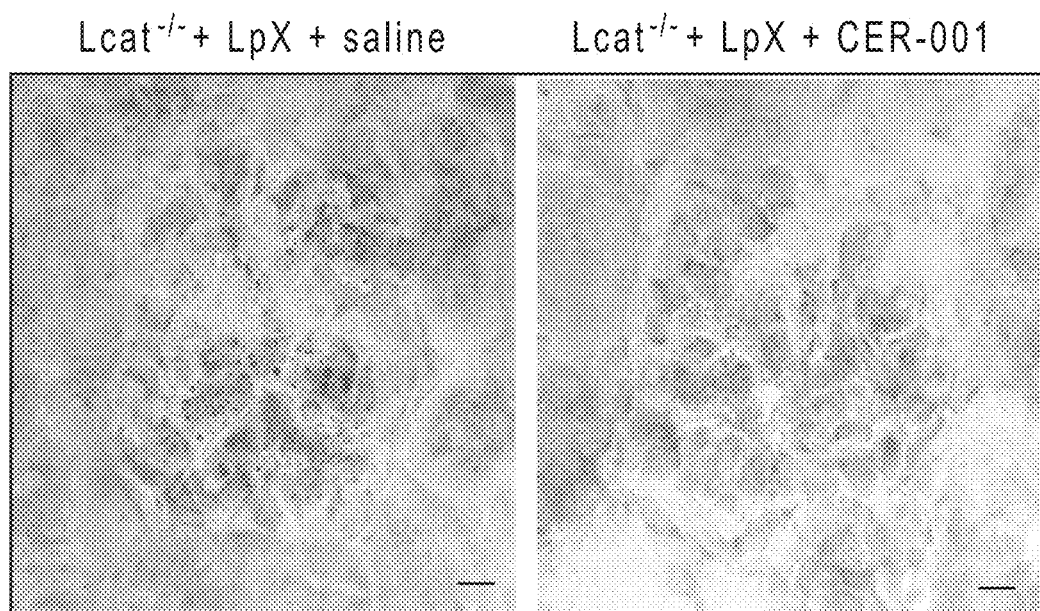
Figure 17B:
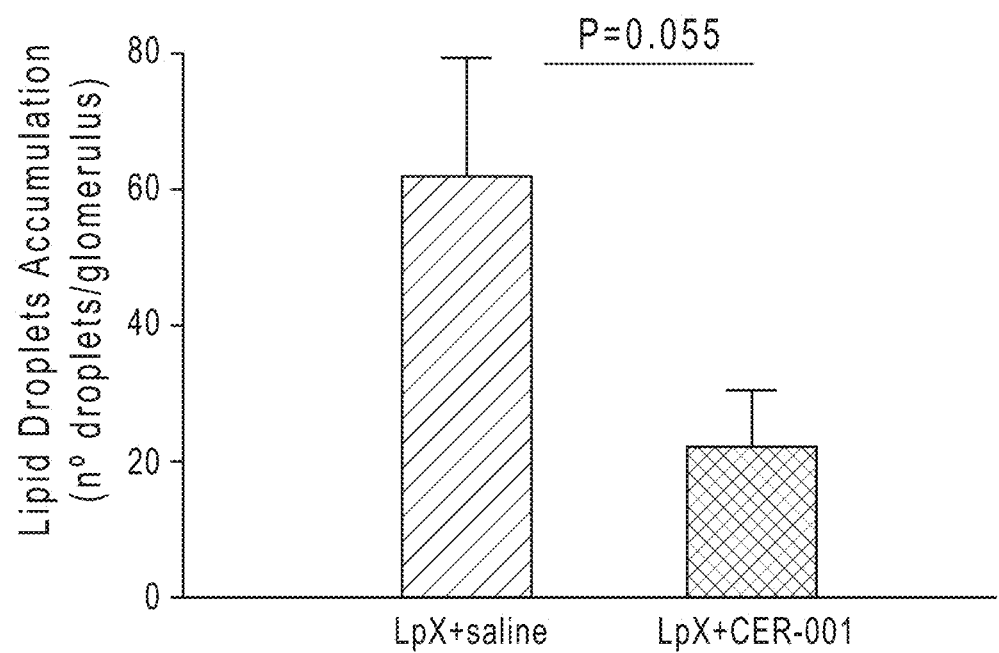

FIGS. 17A-17B are histology images (FIG. 17A) illustrating Oil Red 0 staining of the glomeruli of LpX-injected LCAT -/- mice treated with saline or 10 mg/kg CER-001 to show lipid droplet accumulation as described in Example 4 (Scale bars: 10 μm) and a graph (FIG. 17B) showing the quantification lipid droplet accumulation as described for FIG. 17A. Results are expressed as mean±SEM and were analyzed using unpaired student t-test. P=0.055.

Figure 18:
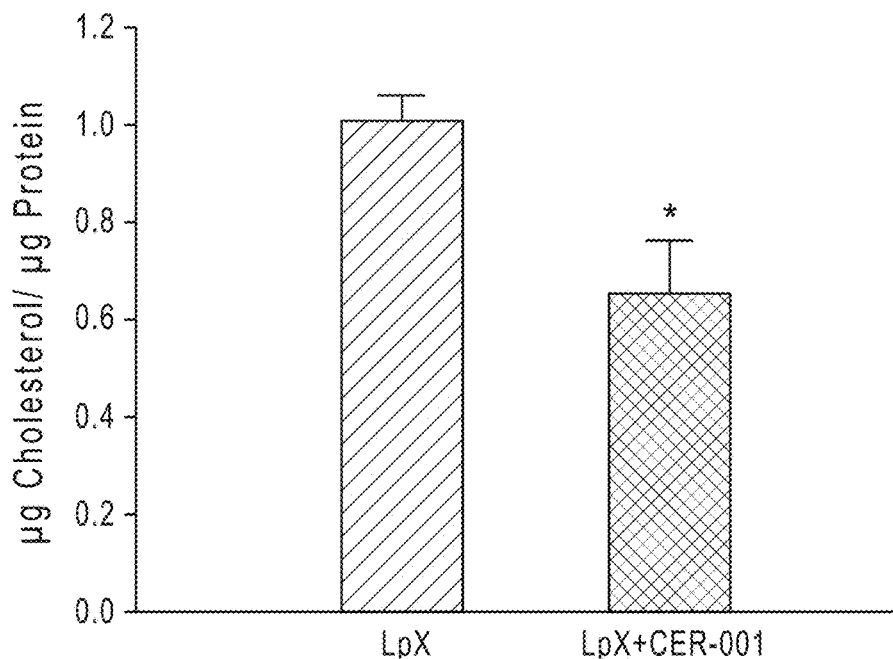

FIG. 18 is graph showing an in vitro evaluation intracellular cholesterol content of podocytes loaded with LpX and treated with saline or CER-001 at a concentration corresponding to the 10 mg/kg dose as described in Example 4. Intracellular cholesterol was assessed by fluorescence. Data are expressed as mean±SEM. N=5, * $P<0.05$ (P=0.015) unpaired student t-test.

Figure 19:
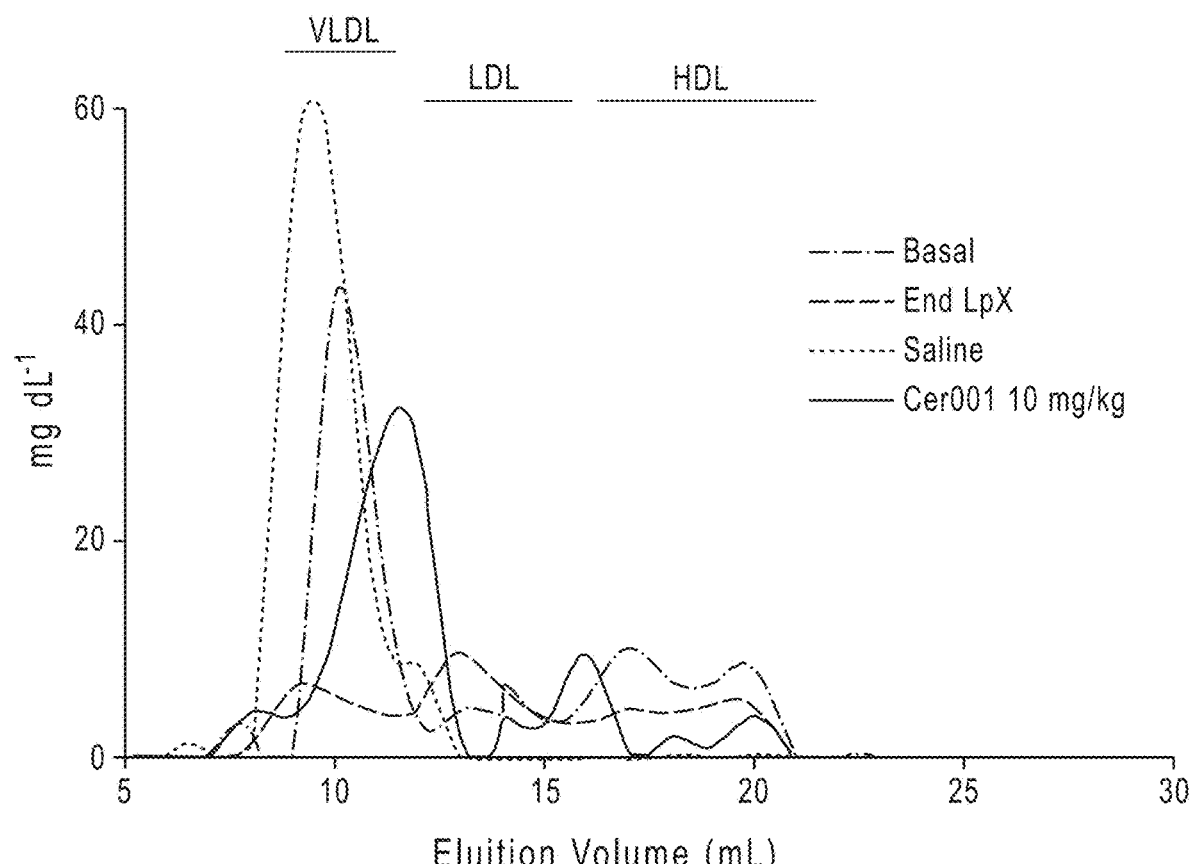

FIG. 19 is a profile of triglyceride distribution as measured by enzymatic technique from lipoproteins separated by FLPC derived from the pooled plasma of LCAT -/- mice at basal condition, at the end of 1-month LpX injection, and after CER-001 or saline treatment as described in Example 4.

Figure 20:
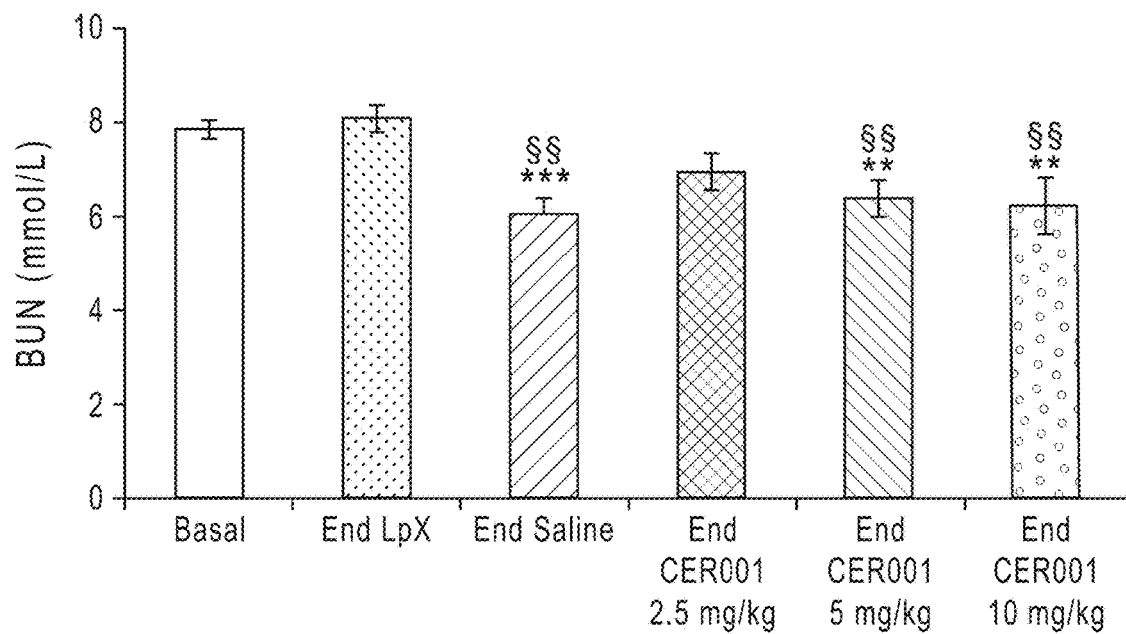

FIG. 20 is a graph showing blood urea nitrogen (BUN) level in LCAT -/- mice in the study described in Example 4.

Figure 21:
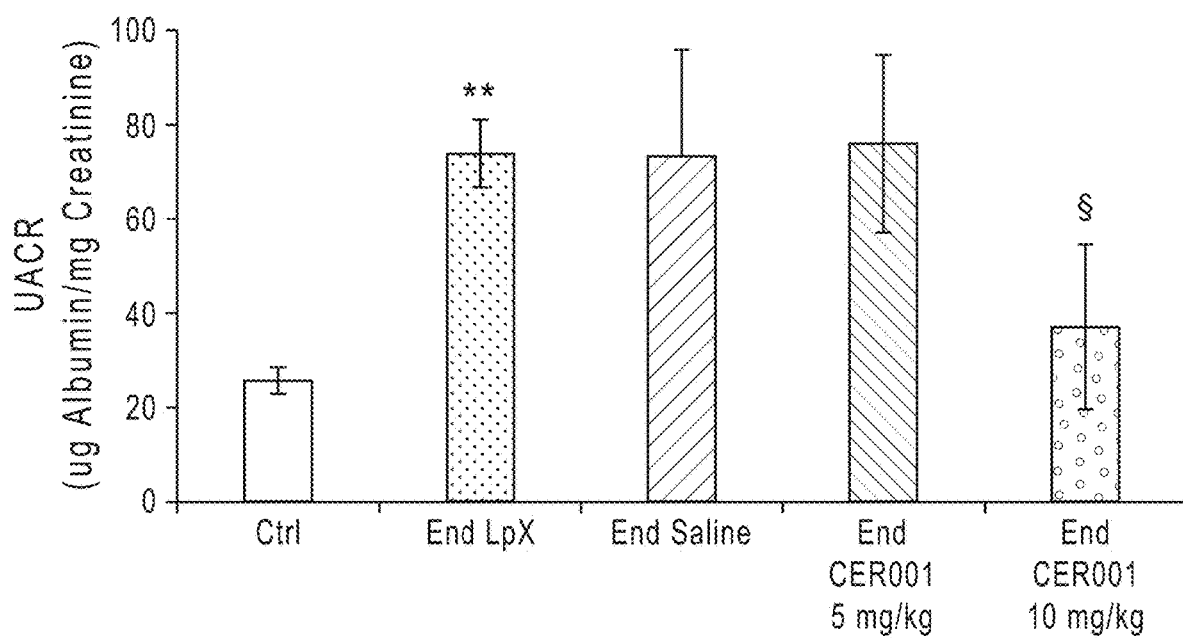

FIG. 21 is a graph showing microalbumin to creatinine ratio (UACR) in urine level in LCAT -/- mice in the study described in Example 4.

Figure 22:
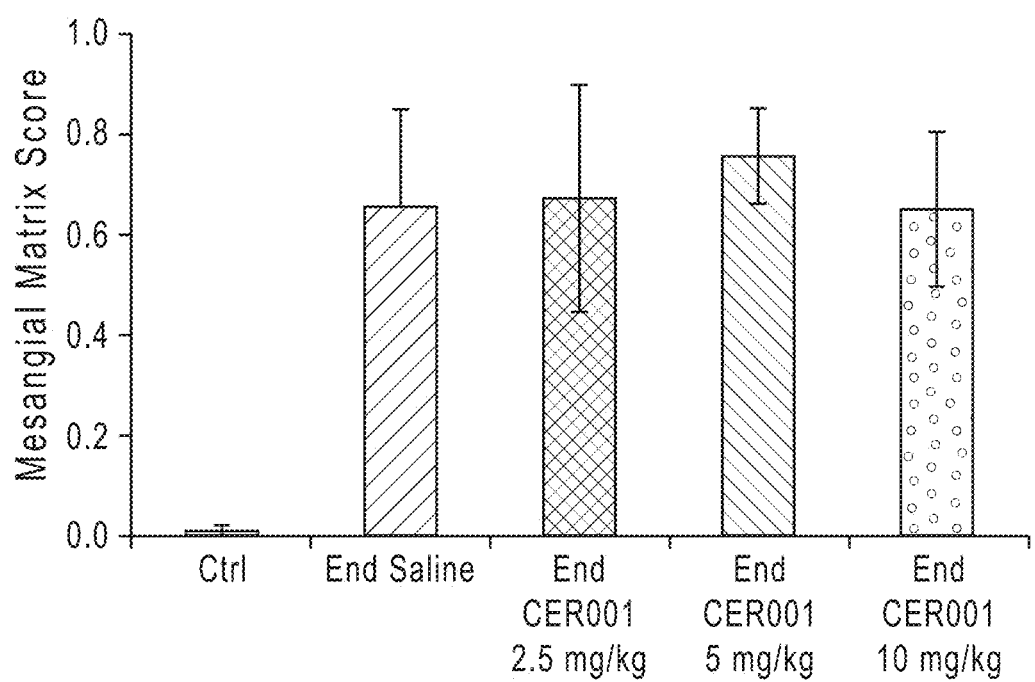

FIG. 22 is a graph showing mesangial matrix expansion measured in kidney of LCAT -/- mice at the end of treatments in the study described in Example 4.

Figure 23:
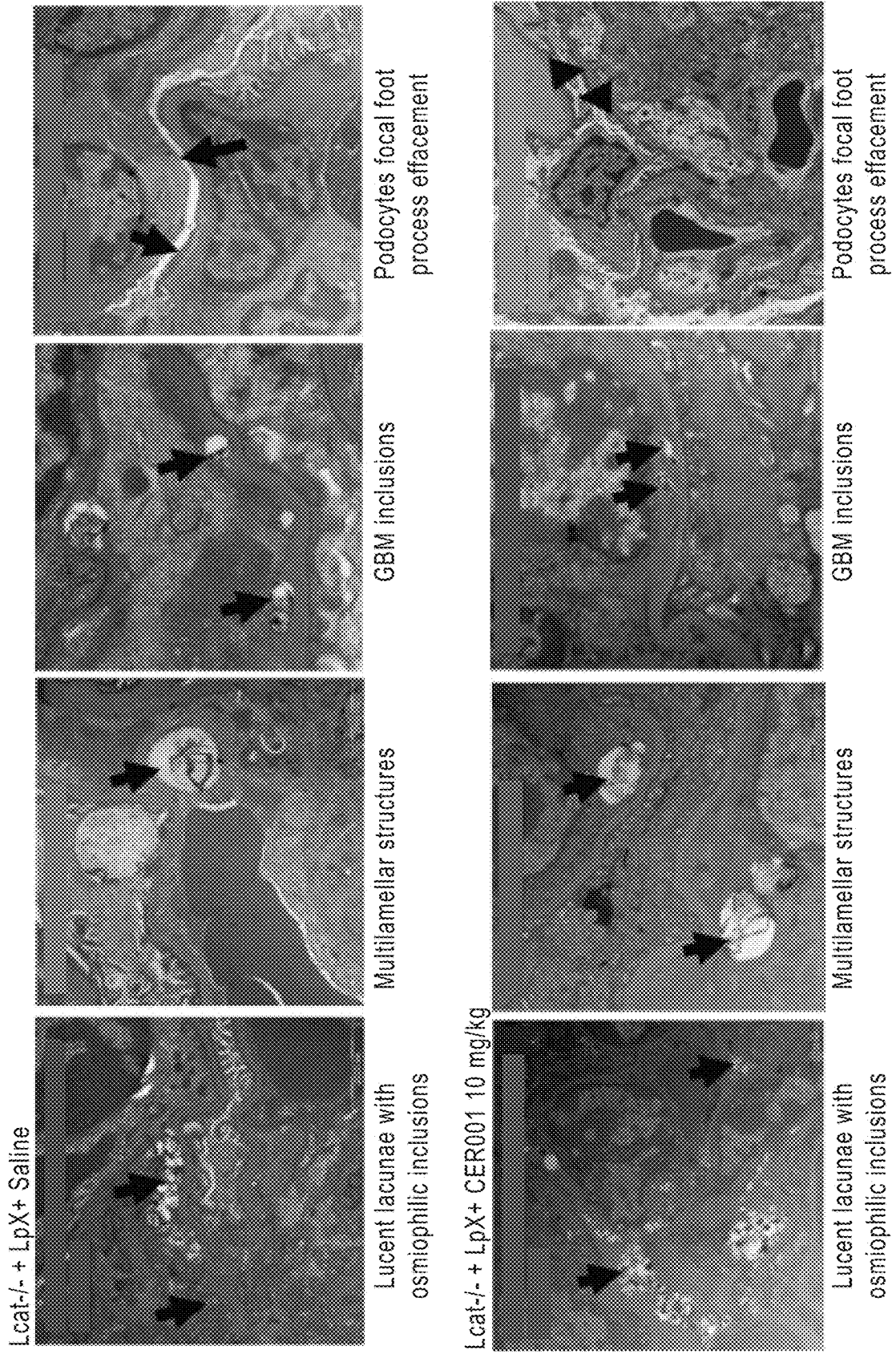

FIG. 23 are representative images showing ultrastructural alterations in kidney of LCAT -/- mice at the end of treatments in the study described in Example 4.

Figure 24:
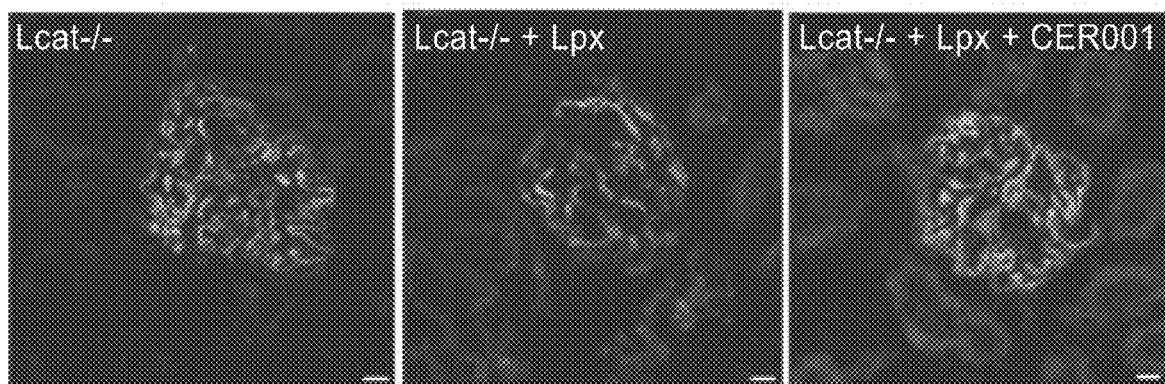

FIG. 24 are representative images showing nephrin expression in kidney of LCAT -/- mice at the end of treatments in the study described in Example 4.

Figure 25:
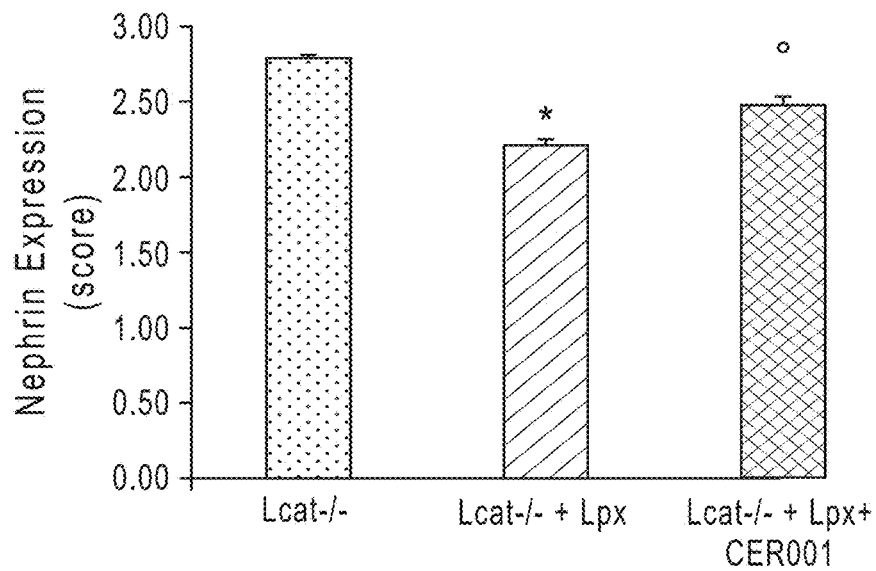

FIG. 25 is a graph showing nephrin expression in kidney of LCAT -/- mice at the end of treatments in the study described in Example 4.

Figure 26:
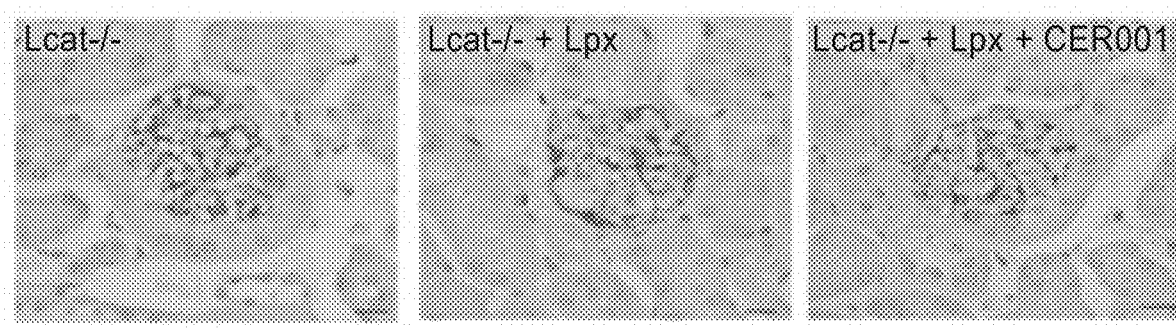

FIG. 26 are representative images showing nestin expression in kidney of LCAT -/- mice at the end of treatments in the study described in Example 4.

Figure 27:
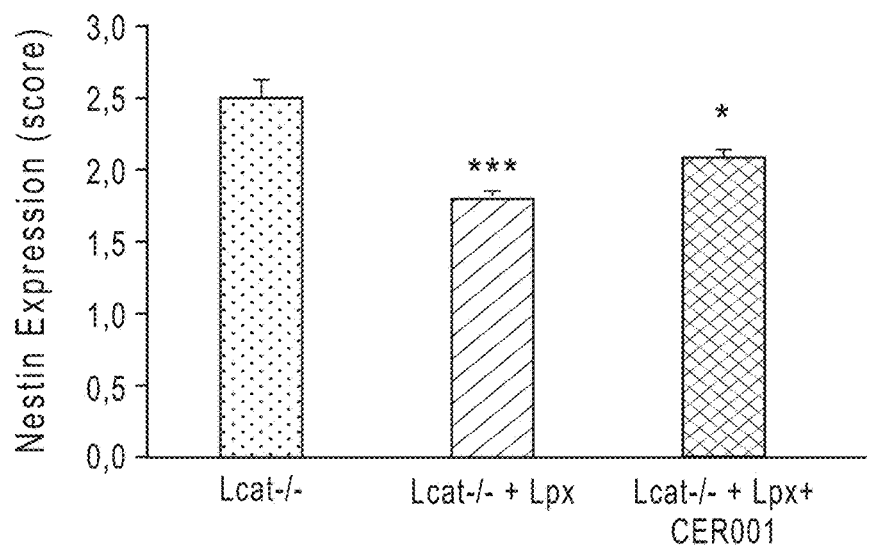

FIG. 27 is a graph showing nestin expression in kidney of LCAT -/- mice at the end of treatments in the study described in Example 4.

Figure 28A:
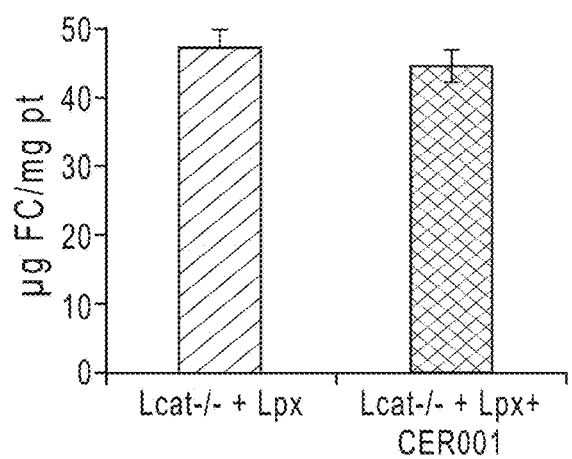
Figure 28B:
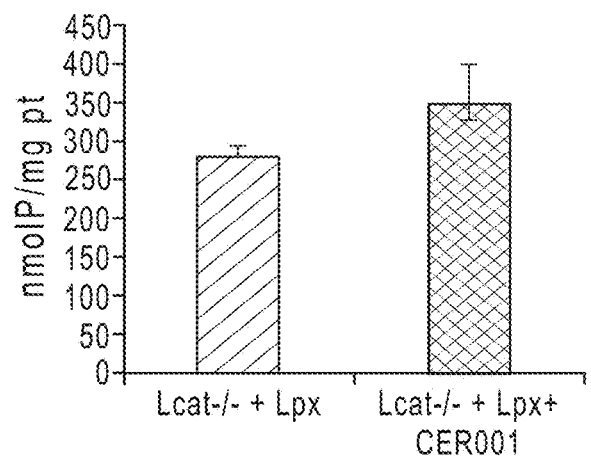

FIGS. 28A-28B are graphs showing unesterified cholesterol (FIG. 28A) and phospholipids (FIG. 28B) content in kidney of LCAT –/– mice at the end of treatments in the study described in Example 4.

5. DETAILED DESCRIPTION

The disclosure provides for treating a subject having kidney disease with CER-001. In some embodiments, methods of the disclosure comprise administering CER-001 to a subject in three phases. First, CER-001 is administered in an initial, intense "induction" regimen. The induction regimen is followed by a less intense "consolidation" regimen. The consolidation regimen is followed by a "maintenance" regimen. In other methods of the disclosure, CER-001 is administered in two phases (e.g., an induction regimen followed by a maintenance regiment) or a single phase (e.g., a maintenance regimen). Induction regimens that can be used in the methods of the disclosure are described in Section 5.2, consolidation regimens that can be used in the methods of the disclosure are described in Section 5.3 and maintenance regimens that can be used in the methods of the disclosure are described in Section 5.4. The dosing regimens of the disclosure comprise administering CER-001 as monotherapy or as part of a combination therapy with one or more medications. Combination therapies are described in Section 5.5. Populations and subpopulations of subjects who can be treated using the methods of the disclosure are described in Section 5.6.

5.1. CER-001

CER-001 as used in the literature and in the Examples below refers to a complex described in Example 4 of WO 2012/109162. WO 2012/109162 refers to CER-001 as a complex having a 1:2.7 lipoprotein weight:total phospholipid weight ratio with a SM:DPPG weight:weight ratio of 97:3. Example 4 of WO 2012/109162 also describes a method of its manufacture.

When used in the context of a dosing regimen of the disclosure, CER-001 refers to a lipoprotein complex whose individual constituents can vary from CER-001 as described in Example 4 of WO 2012/109162 by up to 20%. In certain embodiments, the constituents of the lipoprotein complex vary from CER-001 as described in Example 4 of WO 2012/109162 by up to 10%. Preferably, the constituents of the lipoprotein complex are those described in Example 4 of WO 2012/109162 (plus/minus acceptable manufacturing tolerance variations). The SM in CER-001 can be natural or synthetic. In some embodiments, the SM is a natural SM, for example a natural SM described in WO 2012/109162, e.g., chicken egg SM. In some embodiments, the SM is a synthetic SM, for example a synthetic SM described in WO 2012/109162, e.g., synthetic palmitoylsphingomyelin, for example as described in WO 2012/109162. Methods for synthesizing palmitoylsphingomyelin are known in the art, for example as described in WO 2014/140787. The lipoprotein in CER-001, apolipoprotein A-I (ApoA-I), preferably has an amino acid sequence corresponding to amino acids 25 to 267 of SEQ ID NO:1 of WO 2012/109162. ApoA-I can be purified by animal sources (and in particular from human sources) or produced recombinantly. In preferred embodiments, the ApoA-I in CER-001 is recombinant ApoA-I. CER-001 used in a dosing regimen of the disclosure is preferably highly homogeneous, for example at least 80%, at least 85%, at least 90%, at least 95%, at least 97%, at least 98%, or at least 99% homogeneous, as reflected by a single peak in gel permeation chromatography. See, e.g., Section 6.4 of WO 2012/109162.

5.2. Induction Regimen

Induction regimens suitable for use in the methods of the disclosure entail administering multiple doses of CER-001 separated by 1 or more day between each administration.

The induction regimens typically include at least three doses of CER-001 but can include four or more doses of CER-001, e.g., five, six, seven, eight, nine, ten, eleven or twelve doses.

The induction regimens can last one or more weeks, two or more weeks, three or more weeks, four or more weeks, five or more weeks, six or more weeks, seven or more weeks, eight or more weeks, nine or more weeks, or ten or more weeks.

For example, the induction regimen can comprise administering:
three doses of CER-001 over one week;
three doses of CER-001 over two weeks;
three doses of CER-001 over three weeks;
four doses of CER-001 over two weeks;
four doses of CER-001 over three weeks;
five doses of CER-001 over two weeks;
five doses of CER-001 over three weeks;
five doses of CER-001 over four weeks;
six doses of CER-001 over two weeks;
six doses of CER-001 over three weeks;
six doses of CER-001 over four weeks;
seven doses of CER-001 over three weeks;
seven doses of CER-001 over four weeks;
seven doses of CER-001 over five weeks;
eight doses of CER-001 over three weeks;
eight doses of CER-001 over four weeks;
eight doses of CER-001 over five weeks;
nine doses of CER-001 over three weeks;
nine doses of CER-001 over four weeks;
nine doses of CER-001 over five weeks;
nine doses of CER-001 over six weeks;
ten doses of CER-001 over four weeks;
ten doses of CER-001 over five weeks;
ten doses of CER-001 over six weeks; or
ten doses of CER-001 over seven weeks.

In a preferred embodiment, the induction regimen comprises administering nine doses of CER-001 over three weeks, e.g., on days 1, 2, 4, 7, 9, 11, 14, 16, and 18.

In practice, an administration window can be provided, for example, to accommodate slight variations to a multi-dosing per week dosing schedule. For example, a window of ±2 days or ±1 day around the dosage date can be used.

The dose of CER-001 administered in the induction regimen can range from 4 to 30 mg/kg on a protein weight basis (e.g., 4, 5, 6, 7, 8, 9, 10, 12 15, 20, 25, or 30 mg/kg, or any range bounded by any two of the foregoing values, e.g., 5 to 15 mg/kg, 10 to 20 mg/kg, or 15 to 25 mg/kg). As used herein, the expression "protein weight basis" means that a dose of CER-001 to be administered to a subject is calculated based upon the amount of ApoA-I in the CER-001 to be administered and the weight of the subject. For example, a subject who weighs 70 kg and is to receive a 10 mg/kg dose of CER-001 would receive an amount of CER-001 that provides 700 mg of ApoA-I (70 kg×10 mg/kg). In some embodiments, the dose of CER-001 used in the induction regimen is 8 mg/kg. In some embodiments, the induction regimen comprises nine doses of CER-001 administered over three weeks at a dose of 8 mg/kg. In some embodiments, the dose of CER-001 used in the induction regimen is 10 mg/kg. In some embodiments, the dose of CER-001 used in the induction regimen is 15 mg/kg. In some embodiments, the dose of CER-001 used in the induction regimen is 20 mg/kg. In some embodiments, the induction regimen comprises nine doses of CER-001 administered over three weeks at a dose of 10 mg/kg.

In yet other aspects, CER-001 can be administered on a unit dosage basis. The unit dosage used in the induction phase can vary from 300 mg to 3000 mg per administration.

In particular embodiments, the dosage of CER-001 used during the induction phase is 300 mg to 1500 mg, 400 mg to 1500 mg, 500 mg to 1200 mg, or 500 mg to 1000 mg per administration.

CER-001 is preferably administered as an IV infusion. For example, a stock solution of CER-001 can be diluted in normal saline such as physiological saline (0.9% NaCl) to a total volume between 125 and 250 ml. In a preferred embodiment, subjects weighing less than 80 kg will have a total volume of 125 ml whereas subjects weighing at least 80 kg will have a total volume of 250 ml. CER-001 may be administered over a one-hour period using an infusion pump at a fixed rate of 250 ml/hr. Depending on the needs of the subject, administration can be by slow infusion with a duration of more than one hour (e.g., up to two hours), by rapid infusion of one hour or less, or by a single bolus injection.

5.3. Consolidation Regimen

Consolidation regimens suitable for use in the methods of the disclosure entail administering multiple doses of CER-001 separated by 1 day or greater between each dose e.g., 2 days for greater between each administration.

The consolidation regimens typically include at least two doses of CER-001 but can include three or more doses of CER-001, e.g., four, five, six, seven, eight, nine or ten.

The consolidation regimens can last one or more weeks, two or more weeks, three or more weeks, four or more weeks, five or more weeks, six or more weeks, seven or more weeks, eight or more weeks, nine or more weeks, or ten or more weeks.

For example, the consolidation regimen can comprise administering:
  two doses of CER-001 over one week;
  two doses of CER-001 over two weeks;
  three doses of CER-001 over two weeks;
  three doses of CER-001 over three weeks;
  four doses of CER-001 over two weeks;
  four doses of CER-001 over three weeks;
  five doses of CER-001 over three weeks;
  five doses of CER-001 over four weeks;
  five doses of CER-001 over five weeks;
  six doses of CER-001 over three weeks;
  six doses of CER-001 over four weeks;
  six doses of CER-001 over five weeks;
  seven doses of CER-001 over four weeks;
  seven doses of CER-001 over five weeks;
  seven doses of CER-001 over six weeks;
  eight doses of CER-001 over four weeks;
  eight doses of CER-001 over five weeks;
  eight doses of CER-001 over six weeks;
  nine doses of CER-001 over four weeks;
  nine doses of CER-001 over five weeks;
  nine doses of CER-001 over six weeks;
  nine doses of CER-001 over six weeks;
  ten doses of CER-001 over four weeks;
  ten doses of CER-001 over five weeks;
  ten doses of CER-001 over six weeks; or
  ten doses of CER-001 over seven weeks.

In a preferred embodiment, the consolidation regimen comprises administering six doses of CER-001 over three weeks, e.g., on days 21, 24, 28, 31, 35 and 38 of a treatment regimen that begins with an induction regimen on day 1.

In practice, an administration window can be provided, for example, to accommodate slight variations to a multi-dosing per week dosing schedule. For example, a window of ±2 days or ±1 day around the dosage date can be used.

The dose of CER-001 administered in the consolidation regimen can range from 4 to 30 mg/kg on a protein weight basis (e.g., 4, 5, 6, 7, 8, 9, 10, 12, 15, 20, 25, or 30 mg/kg, or any range bounded by any two of the foregoing values, e.g., 5 to 15 mg/kg, 10 to 20 mg/kg, or 15 to 25 mg/kg). As used herein, the expression "protein weight basis" means that a dose of CER-001 to be administered to a subject is calculated based upon the amount of ApoA-I in the CER-001 to be administered and the weight of the subject. For example, a subject who weighs 70 kg and is to receive a 10 mg/kg dose of CER-001 would receive an amount of CER-001 that provides 700 mg of ApoA-I (70 kg×10 mg/kg). In some embodiments, the dose of CER-001 used in the consolidation regimen is 8 mg/kg. In some embodiments, the consolidation regimen comprises six doses of CER-001 administered over three weeks at a dose of 8 mg/kg. In some embodiments, the dose of CER-001 used in the consolidation regimen is 10 mg/kg. In some embodiments, the dose of CER-001 used in the consolidation regimen is 15 mg/kg. In some embodiments, the dose of CER-001 used in the consolidation regimen is 20 mg/kg. In some embodiments, the consolidation regimen comprises six doses of CER-001 administered over three weeks at a dose of 10 mg/kg.

In yet other aspects, CER-001 can be administered on a unit dosage basis. The unit dosage used in the consolidation phase can vary from 300 mg to 3000 mg per administration.

In particular embodiments, the dosage of CER-001 used during the consolidation phase is 300 mg to 1500 mg, 400 mg to 1500 mg, 500 mg to 1200 mg, or 500 mg to 1000 mg per administration.

In some embodiments, the dose of the CER-001 administered during the consolidation phase is greater than the dose of the CER-001 administered during the induction phase. For example, the dose administered in the consolidation phase can be 1.5 to 3 times the dose administered in the induction phase. In specific embodiments, the dose of CER-001 administered in the consolidation phase is 2 times the dose of the CER-001 administered in the consolidation phase. Increasing the dose in the consolidation phase can offset the reduced frequency of dosing. In other embodiments, the dose of the CER-001 administered during the consolidation phase is the same as the dose of the CER-001 administered during the induction phase.

CER-001 can be administered during the consolidation phase in the same manner as described in Section 5.2, e.g., as an IV infusion over a one-hour period. When the dose of CER-001 administered during the consolidation phase is larger than the dose administered in the induction phase, the CER-001 can optionally be administered in a larger volume and/or infused over a longer period of time. For example, when the dose of CER-001 administered during the consolidation phase is twice the dose administered during the induction phase, the administration volume can be increased (e.g., doubled) and/or the infusion time can be increased (e.g., doubled).

5.4. Maintenance Regimen

The methods of the disclosure can comprise a maintenance regimen, which typically follows an induction regimen and optionally a consolidation regimen. In some embodiments, a maintenance regimen comprises administering CER-001 to a subject on a less frequent basis than during the induction phase and/or the consolidation phase.

Typically, CER-001 is administered once every 3 or more days, for example once every week or twice a week, during the maintenance regimen.

The maintenance regimen can entail administering CER-001 for one month or longer, two months or longer, three months or longer, six months or longer, nine months or longer, a year or longer, 18 months or longer, two years or longer, or indefinitely.

In some embodiments, the maintenance regimen comprises administering CER-001 once every 5 days to one week for at least 16 weeks. In other embodiments, the maintenance regimen comprises administering CER-001 once every week for at least 20 weeks, for at least 30 weeks, or for at least 40 weeks.

Similar to the administration window described above in Section 5.2, an administration window can also be used in the maintenance regimen to accommodate slight variations to a weekly dosing schedule. For example, a window of ±2 days or ±1 day around the weekly date can be used.

The dose of CER-001 administered in the maintenance regimen can range from 4 to 30 mg/kg on a protein weight basis (e.g., 4, 5, 6, 7, 8, 9, 10, 12, 15, 20, 25, or 30 mg/kg, or any range bounded by any two of the foregoing values, e.g., 5 to 15 mg/kg, 10 to 20 mg/kg, or 15 to 25 mg/kg). For example, a subject who weighs 70 kg and is to receive a 10 mg/kg dose of CER-001 would receive an amount of CER-001 that provides 700 mg of ApoA-I (70 kg×10 mg/kg). In some embodiments, the dose of CER-001 used in the maintenance regimen is 8 mg/kg. In some embodiments, the dose of CER-001 used in the maintenance regimen is 10 mg/kg. In some embodiments, the dose of CER-001 used in the consolidation regimen is 15 mg/kg. In some embodiments, the dose of CER-001 used in the consolidation regimen is 20 mg/kg.

In yet other aspects, CER-001 can be administered on a unit dosage basis. The unit dosage used in the maintenance phase can vary from 300 mg to 3000 mg per administration.

In particular embodiments, the dosage of CER-001 used during the maintenance phase is 300 mg to 1500 mg, 400 mg to 1500 mg, 500 mg to 1200 mg, or 500 mg to 1000 mg per administration.

In some embodiments, the dose of the CER-001 administered during the maintenance phase is greater than the dose of the CER-001 administered during the induction phase and/or consolidation phase. For example, the dose administered in the maintenance phase can be 1.5 to 3 times the dose administered in the consolidation phase. In specific embodiments, the dose of CER-001 administered in the maintenance phase is 2 times the dose of the CER-001 administered in the consolidation phase. Increasing the dose in the maintenance phase can offset the reduced frequency of dosing. In other embodiments, the dose of the CER-001 administered during the maintenance phase is the same as the dose of the CER-001 administered during the induction phase and/or consolidation phase. In some embodiments, the dose administered in the maintenance phase can be adjusted, for example increased or decreased.

CER-001 can be administered during the maintenance phase in the same manner as described in Section 5.2, e.g., as an IV infusion. When the dose of CER-001 administered during the maintenance phase is larger than the dose administered in the consolidation phase, the CER-001 can optionally be administered in a larger volume and/or infused over a longer period of time. For example, when the dose of CER-001 administered during the maintenance phase is twice the dose administered during the consolidation phase, the administration volume can be increased (e.g., doubled) and/or the infusion time can be increased (e.g., doubled).

5.5. Combination Therapies

The subjects can be treated with CER-001 as a monotherapy or a part of a combination therapy regimen, e.g., with one or more lipid control medications such as a statin (e.g., atorvastatin, rosuvastatin, simvastatin, fluvastatin, lovastatin, pravastatin), a cholesterol absorption inhibitor (e.g., ezetimibe), niacin, aspirin, a proprotein convertase subtilisin/kexin type 9 (PCSK9) inhibitor (e.g., an antibody such as alirocumab, bococizumabevolocumab, 1D05-IgG2 (Ni et al., 2011, J Lipid Res. 52(1):78-86), and LY3015014 (Kastelein et al., 2016, Eur Heart J 37(17):1360-9) or an RNAi therapeutic such as ALN-PCSSC (the Medicines Company)).

A combination therapy regimen can entail administering CER-001 in combination with one or more of the foregoing medicines and/or one or more of the foregoing classes of medications. In some embodiments, the subject is treated with CER-001 in combination with atorvastatin. In some embodiments, the subject is treated with CER-001 in combination with ezetimibe. In some embodiments, the subject is treated with CER-001 in combination with niacin. In some embodiments, the subject is treated with CER-001 in combination with rosuvastatin. In some embodiments, the subject is treated with CER-001 in combination with simvastatin. In some embodiments, the subject is treated with CER-001 in combination with aspirin. In some embodiments, the subject is treated with CER-001 in combination with fluvastatin. In some embodiments, the subject is treated with CER-001 in combination with lovastatin. In some embodiments, the subject is treated with CER-001 in combination with pravastatin. In some embodiments, the subject is treated with CER-001 in combination with alirocumab. In some embodiments, the subject is treated with CER-001 in combination with evolocumab. In some embodiments, the subject is treated with CER-001 in combination with ALN-PCSsc. In each of the foregoing embodiments, the lipid control medicine can be the only lipid control medicine that the subject receives in combination with CER-001 therapy, or can be part of a combination of lipid control medicines administered in combination with CER-001 therapy.

Therapy with CER-001 can be added to a background lipid lowering therapy started before therapy with CER-001.

In some embodiments, the subject is treated with a stable dose of a lipid control medication for at least 6 weeks (e.g., 6 weeks, 8 weeks, 2 months, 6 months, 1 year, or more than one year) before beginning therapy with CER-001 according to a dosing regimen of the disclosure. Alternatively, CER-001 therapy can be started before or concurrently with treatment with one or more lipid control medications.

5.6. Subject Populations

The subject treated according to the dosing regimens of the disclosure can be any subject in need of therapy for kidney disease. In some embodiments, the subject treated according to the dosing regimens has glomerulopathy. In some embodiments the subject treated according to the dosing regimens of the disclosure has an LCAT deficiency (e.g., an LCAT deficiency due to an LCAT mutation or an LCAT deficiency which is an acquired LCAT deficiency). In some embodiments the subject treated according to the dosing regimens of the disclosure has diabetic nephropathy. In some embodiments the subject treated according to the dosing regimens of the disclosure has CKD. CKD can be defined as three or more months of: decreased kidney function (e.g., an estimated Glomerular Filtration Rate (GFR) of <60 mL/min/1.73 $m^2$) and/or evidence of kidney damage (e.g., a Urine Albumin-to-Creatinine Ratio (UACR) of 30 mg/g, abnormal kidney imaging or biopsy).

In some embodiments the subject treated according to the dosing regimens of the disclosure is undergoing kidney dialysis treatment. In some embodiments the subject treated according to the dosing regimens of the disclosure has undergone a kidney transplant.

In some embodiments, the subject treated according to the dosing regimens of the disclosure is not undergoing kidney dialysis treatment. In some embodiments, the treatment delays the need for kidney dialysis in the subject.

In some embodiments, the subject treated according to the dosing regimens of the disclosure has not undergone a kidney transplant. In some embodiments, the treatment delays the need for a kidney transplant in the subject.

In certain embodiments the subject treated according to the dosing regimens of the disclosure is suffering from glomerulopathy associated with LCAT deficiency (e.g., an LCAT deficiency due to an LCAT mutation or an LCAT deficiency which is an acquired LCAT deficiency). Subjects having a mutation in one or more of their LCAT genes can be treated by the therapeutic methods described herein. The subject can be homozygous or heterozygous for the mutation. In some embodiments, the subject has familial LCAT deficiency (e.g., a subject lacking LCAT activity). In other embodiments, the subject has a partial LCAT deficiency (e.g., the subject can be a subject with Fish eye disease).

In some embodiments, the subject has an LCAT deficiency that is acquired (e.g., not due to an LCAT mutation). Acquired LCAT deficiency is associated with, for example, CKD, alcoholic liver disease and hepatorenal syndrome (Calabresi et al., 2014, Journal of Internal Medicine, 277 (5):552-561; Baragetti et al., 2020, J. Clin. Med. 9(7):2289; Hovig et al., 1978, Lab Invest. 38(5):540-9; Sasso et al., 1989 Panminerva Med. 31(1):30-3). LCAT deficiency has also been observed in subjects having inhibitory autoantibodies directed against LCAT (Takahashi et al., 2013, JASN 24(8):1305-1312).

Subjects having an LCAT deficiency typically have low cholesteryl ester (CE) to total cholesterol (TC) ratios. In some embodiments, a subject having an LCAT deficiency has a CE to TC ratio of 60% or less, for example 0% to 60%, 0% to 50%, 0% to 25%, 25% to 60%, or 25% to 50%. Subjects having an LCAT deficiency can have low levels of plasma LCAT. In some embodiments, a subject having an LCAT deficiency has a plasma LCAT concentration of 0 µg/ml to 4 µg/ml, for example, 0 µg/ml to 3 µg/ml, 0 µg/ml to 2 µg/ml, 1 µg/ml to 4 µg/ml, or 1 µg/ml to 3 µg/ml.

In some embodiments, a subject treated according to a dosing regimen of the disclosure has hepatorenal syndrome (HRS) or is at risk of HRS. Subjects at risk of HRS include subjects having chronic liver disease, for example subjects with advanced cirrhosis. In some embodiments, the subject has chronic liver disease. In some embodiments, the subject has alcoholic liver disease. HRS has historically been classified as type 1 HRS, where renal function rapidly deteriorates over days to weeks, and type 2 HRS, where deterioration occurs over months. See, e.g., Amin et al., 2019, Seminars in Nephrology 39(1):17-30, the contents of which are incorporated herein by reference in their entireties. In some embodiments, a subject treated according to a dosage regimen of the disclosure has type 1 HRS. In other embodiments, a subject treated according to a dosage regiment of the disclosure has type 2 HRS.

6. EXAMPLES

5.1 Example 1: Absorption of CER-001 Following Administration

Figure 1:
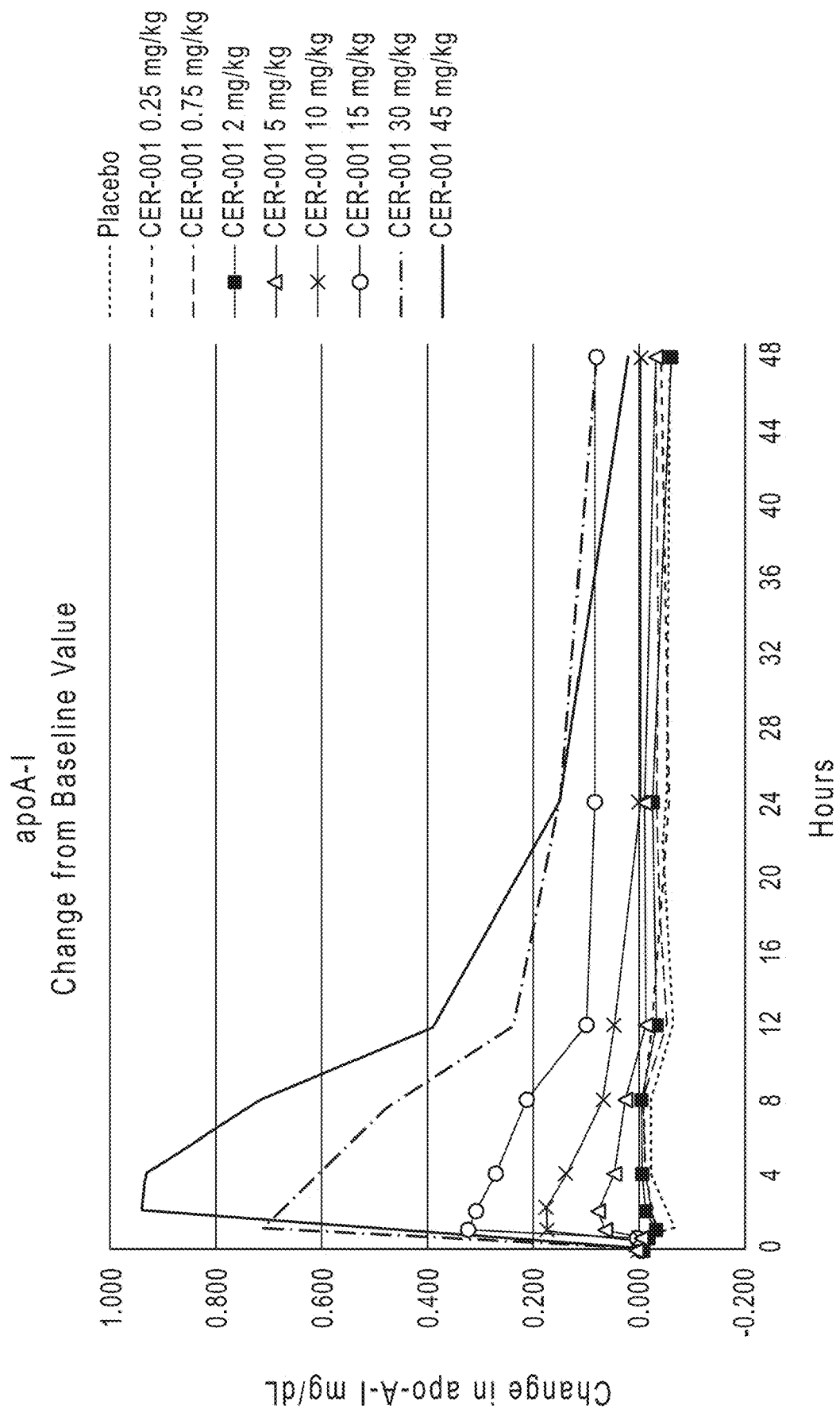
FIG. 1 is a graph showing the change from baseline value of apoA-1 in the study described in Example 1.
Figure 2:
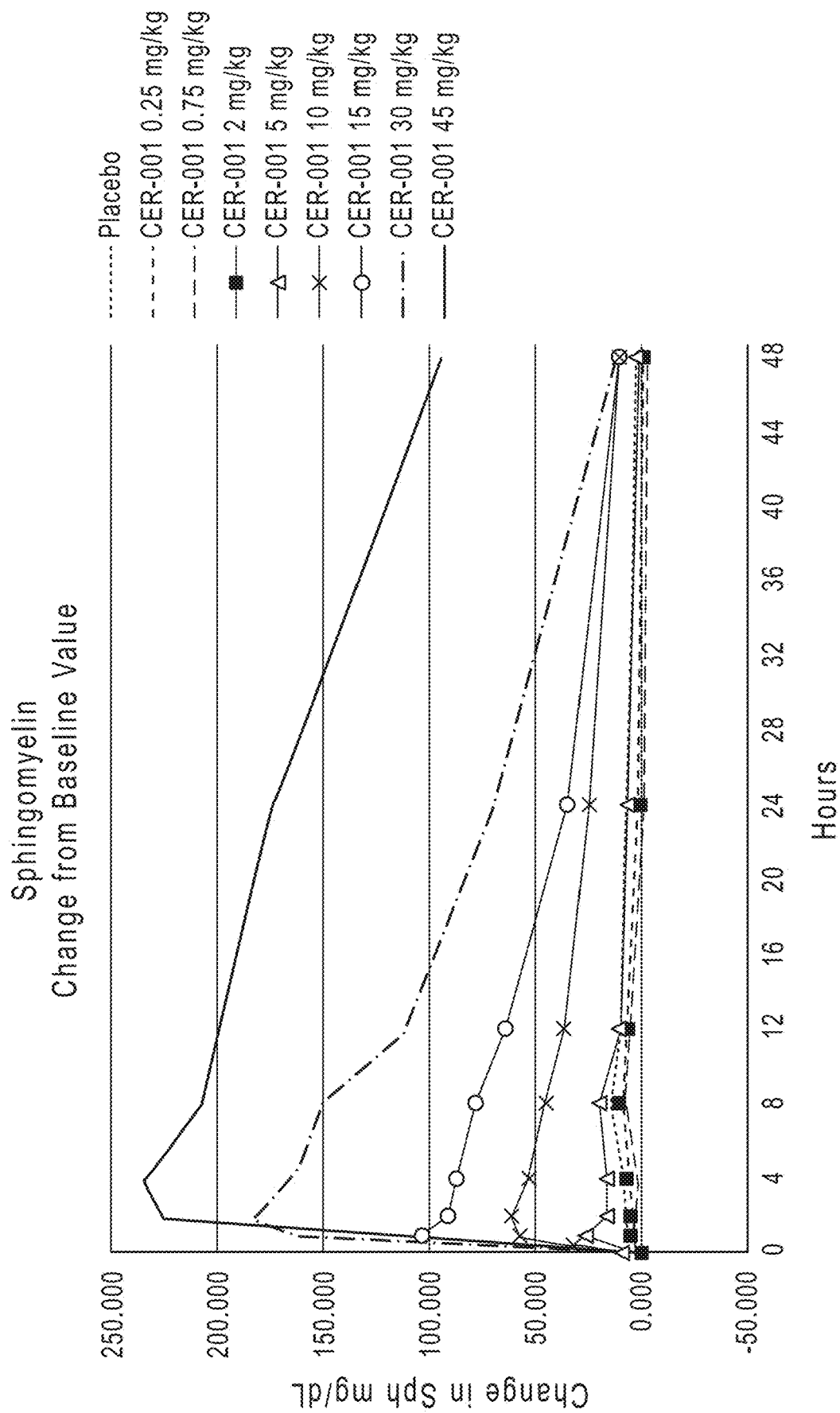
FIG. 2 is a graph showing the change from baseline value of sphingomyelin in the study described in Example 1.

CER-001 was administered to human subjects as single IV doses. As shown in FIG. 1 and FIG. 2 there was a rapid rise in plasma apoA-I and sphingomyelin, with the highest concentrations observed between 2 and 4 hours from the start of infusion. Concentrations return to baseline levels within 24 to 48 hours for doses less than 15 mg/kg.

5.2 Example 2: Preclinical Safety Data

A 20 mg/kg dose was considered a no-adverse effect dose in a 4-week dose studies in rats, as well as in 4-week and 26-week dose studies in monkeys.

CER-001 caused a dose-dependent increase in total and unesterified cholesterol, an expected pharmacodynamic effect, following the mobilization of cholesterol, in both rats and monkeys. CER-001 caused moderate to marked, but transient, increases in liver transaminases, ALT and AST, alkaline phosphatase, total bilirubin and triglycerides at higher doses (100 mg/kg and above). These changes were generally reversible within 24 to 48 hours of administration.

The liver, spleen and bone marrow were considered to be the target organs for the toxic effect of CER-001. The changes in hepatic enzyme and renal parameters noted in the single-dose study in rats and the increasing-dose study in monkeys at doses greater than or equal to 100 mg/kg were transient and secondary to effects exaggerated pharmacology. These changes were reversible over a short period without treatment.

CER-001 did not induce any antibodies against recombinant human apoA-I in rats. Antibodies to human apoA-I were detectable in monkeys when administered in multiple doses.

5.3 Example 3: Effect of LCAT on Remodeling and Catabolic Fate of CER-001

The aim of the study was to investigate whether the absence of LCAT affects the remodeling and catabolic fate of CER-001.

Three groups of animals were used in the study:
- LCAT -/- mice (see Manzini et al., 2015, Vascul Pharmacol, 74:114-121)
- LCAT -/- mice injected with LpX as a model of renal disease (see Ossoli et al., 2016, PlosOne 11:e0150083)
- WT mice LCAT -/- and WT mice (n=3 per group) were injected with CER-001 at the doses of 2.5 mg/kg, 5 mg/kg, or 10 mg/kg every other day for 2 weeks (a total of 8 injections). Blood was collected before starting the injections, and at day 1 and day 14 at the following time points: 30 minutes, 1 hrs, 4 hrs, 24 hrs, 48 hrs. Plasma lipid profile Plasma lipid profile was evaluated at baseline and at each time-point. Tables 1-4 below report the lipid values measured at baseline and at the end of treatment. Baseline end of treatment (48 h after last injection).

TABLE 1

Total Cholesterol Profile

| | Baseline | End of treatment (48 h after last injection) | P value |
|---|---|---|---|
| TOTAL CHOLESTEROL | | | |
| 2.5 mg/kg | | | |
| WT | 72.50 ± 7.06 | 70.93 ± 2.47 | 0.719 |
| LCAT-/- | 28.31 ± 5.13 | 21.63 ± 2.80 | 0.011 |
| 5 mg/kg | | | |
| WT | 71.00 ± 4.97 | 80.20 ± 21.22 | 0.194 |
| LCAT-/- | 32.78 ± 7.19 | 22.47 ± 1.63 | 0.038 |
| 10 mg/kg | | | |
| WT | 68.74 ± 8.68 | 61.20 ± 6.75 | 0.193 |
| LCAT-/- | 28.57 ± 6.41 | 23.13 ± 3.29 | 0.190 |

Referring to Table 1, plasma total cholesterol levels slightly decreased in LCAT-/- mice at the end of treatment, while levels remained unchanged in WT mice. Plasma cholesterol levels significantly increased in plasma of both LCAT -/- and WT mice treated with rHDL containing phosphatidylcholine, apoA-I and cholesterol (data not shown).

TABLE 2

Triglycerides Profile

| | Baseline | End of treatment (48 h after last injection) | P value |
|---|---|---|---|
| TRIGLYCERIDES | | | |
| 2.5 mg/kg | | | |
| WT | 81.51 ± 27.89 | 127.80 ± 15.97 | 0.062 |
| LCAT-/- | 134.67 ± 39.77 | 134.80 ± 28.17 | 0.764 |
| 5 mg/kg | | | |
| WT | 64.71 ± 16.70 | 69.17 ± 28.30 | 0.733 |
| LCAT-/- | 150.02 ± 34.33 | 108.33 ± 37.59 | 0.092 |
| 10 mg/kg | | | |
| WT | 78.64 ± 24.27 | 43.27 ± 11.17 | 0.033 |
| LCAT-/- | 136.61 ± 31.81 | 50.03 ± 22.02 | 0.001 |

Referring to Table 2, plasma triglyceride levels significantly decreased in both WT and LCAT-/- mice after treatment with CER-001 at the highest dose (10 mg/kg). On the contrary, in mice treated with rHDL containing phosphatidylcholine, apoA-I and cholesterol significantly increased triglyceride levels in plasma were observed.

TABLE 3

Phospholipids Profile

| | Baseline | End of treatment (48 h after last injection) | P value |
|---|---|---|---|
| PHOSPHOLIPIDS | | | |
| 2.5 mg/kg | | | |
| WT | 139.98 ± 37.82 | 184.90 ± 23.23 | 0.078 |
| LCAT-/- | 115.73 ± 33.61 | 83.90 ± 6.52 | 0.128 |
| 5 mg/kg | | | |
| WT | 141.20 ± 42.60 | 118.40 ± 21.63 | 0.401 |
| LCAT-/- | 111.08 ± 39.38 | 64.73 ± 8.78 | 0.072 |
| 10 mg/kg | | | |
| WT | 134.04 ± 29.42 | 79.83 ± 9.48 | 0.008 |
| LCAT-/- | 124.78 ± 30.90 | 47.07 ± 4.24 | 0.001 |

Referring to Table 3, plasma phospholipids (measured as phosphatidylcholine) decreased in LCAT-/- mice in a dose dependent way, while in WT mice the decrease was evident only at the highest dose. On the contrary, when mice were treated with rHDL containing phosphatidylcholine, apoA-I and cholesterol a significant increase of phospholipids in plasma were observed.

TABLE 4

HDL-Cholesterol Profile

| | Baseline | End of treatment (48 h after last injection) | P value |
|---|---|---|---|
| HDL-CHOLESTEROL | | | |
| 2.5 mg/kg | | | |
| WT | 59.87 ± 9.49 | 66.77 ± 2.90 | 0.252 |
| LCAT-/- | 0.98 ± 0.68 | 2.20 ± 1.48 | 0.041 |
| 5 mg/kg | | | |
| WT | 59.88 ± 5.34 | 67.63 ± 6.73 | 0.060 |
| LCAT-/- | 1.28 ± 0.84 | 1.20 ± 0.26 | 0.696 |
| 10 mg/kg | | | |
| WT | 55.83 ± 9.62 | 56.63 ± 6.73 | 0.895 |
| LCAT-/- | 1.01 ± 0.44 | 2.37 ± .075 | 0.001 |

Referring to Table 4, plasma HDL-C levels tended to increase in all treated groups. The increase reached statistical significance in the LCAT-/- mice (except at 5 mg/kg dose). The same effect was detectable in mice treated with rHDL containing phosphatidylcholine, apoA-I and cholesterol.

Plasma lipoproteins were separated by Fast Protein Liquid Chromatography (FPLC) with a size exclusion method that permits the separation of lipoproteins in plasma according to size (Simonelli et al., 2013, Biologicals. 41:446-449). By this method, it is possible to identify three main regions that correspond to VLDL (the first to be eluted), LDL, and HDL (which are smaller and eluted as the last particles). Pooled plasma of 3 animals for each dose was used for FPLC analysis; total cholesterol and phospholipid content was measured in each elution fraction by enzymatic assay (Simonelli et al., 2013, Biologicals. 41:446-449). Since the most evident changes in plasma lipid were observed at the highest dose, the lipoprotein profiles obtained after treatment with CER-001 at 10 mg/kg after the first injection and at the end of treatment are reported in FIGS. 3A-6B.

Figure 3A:
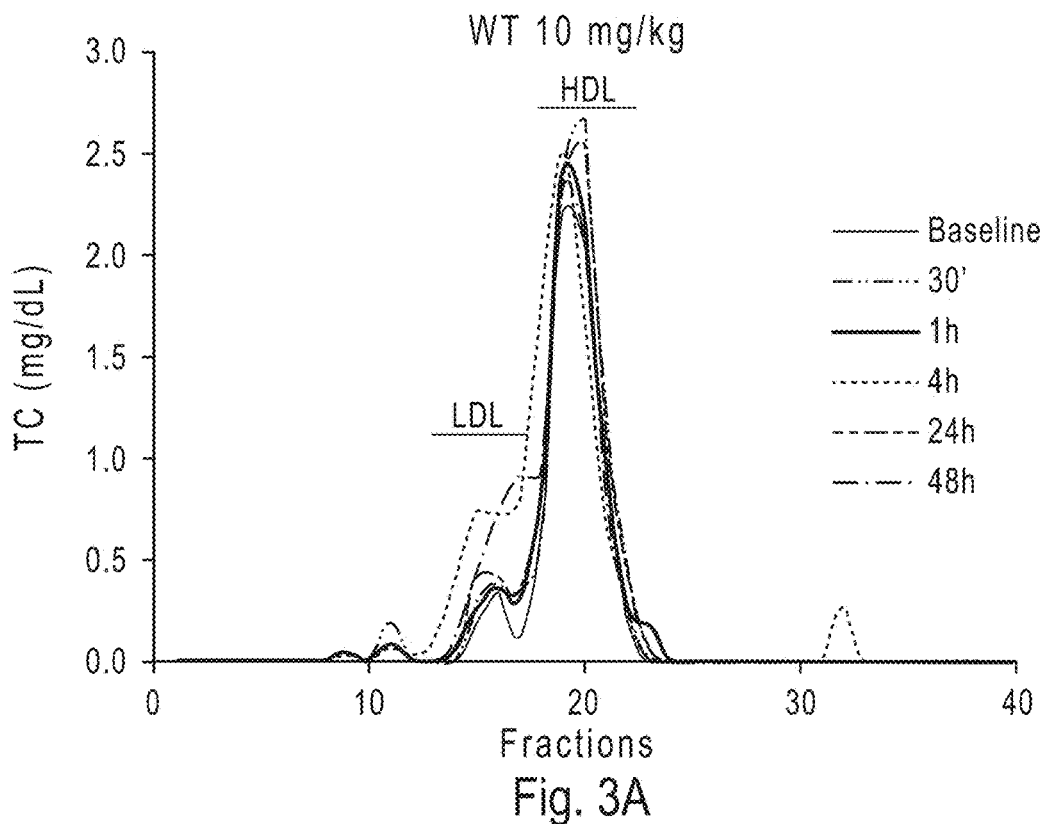
FIGS. 3A-3B are graphs showing the total cholesterol distribution obtained after treatment with CER-001 at 10 mg/kg after the first injection (FIG. 3A) and at the end of treatment (FIG. 3B) in the study described in Example 3.
Figure 3B:
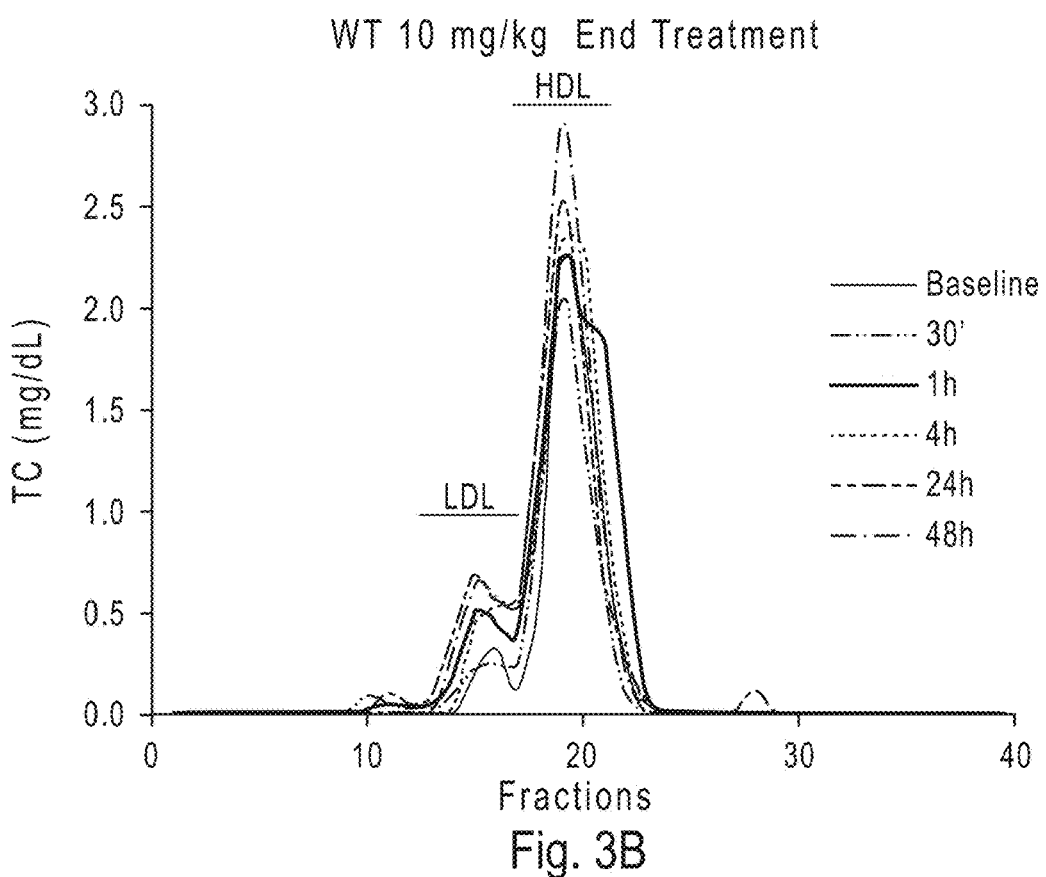

Referring to FIGS. 3A-3B, total cholesterol distribution did not show important changes after CER-001 administration in WT mice. Interestingly, the peak corresponding to LDL region increased only at the end of treatment 1 hour after last administration and remained elevated until the next 48 hours.

Figure 4A:
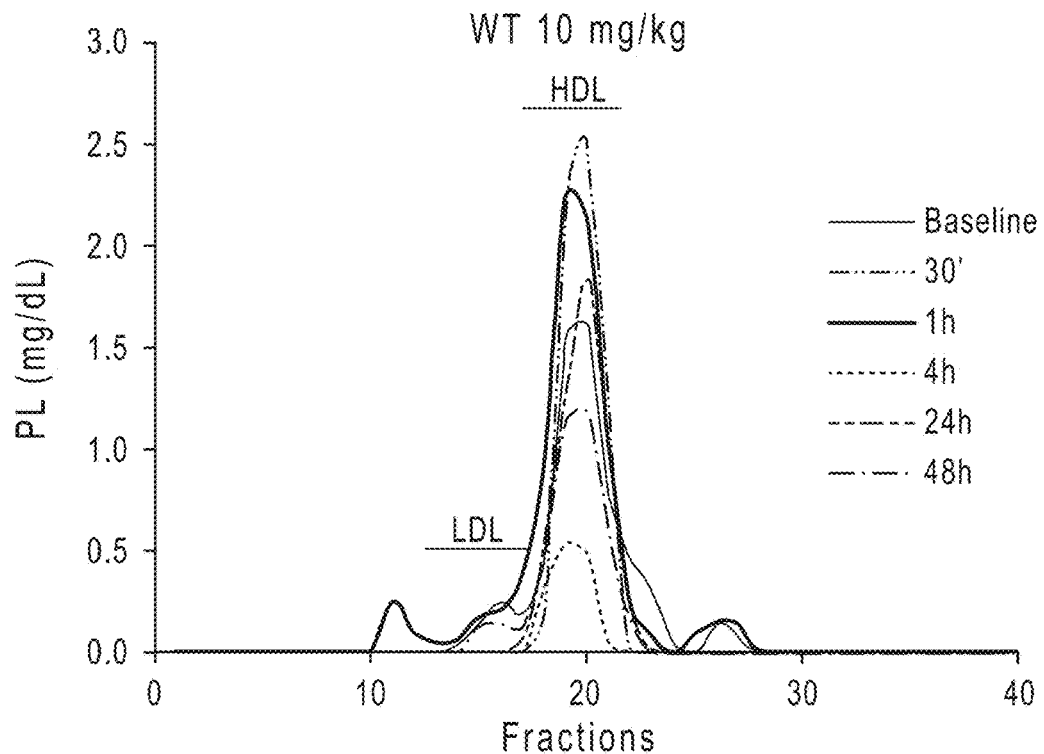
FIGS. 4A-4B are graphs showing the phospholipid content obtained after treatment with CER-001 at 10 mg/kg after the first injection (FIG. 4A) and at the end of treatment (FIG. 4B) in the study described in Example 3.
Figure 4B:
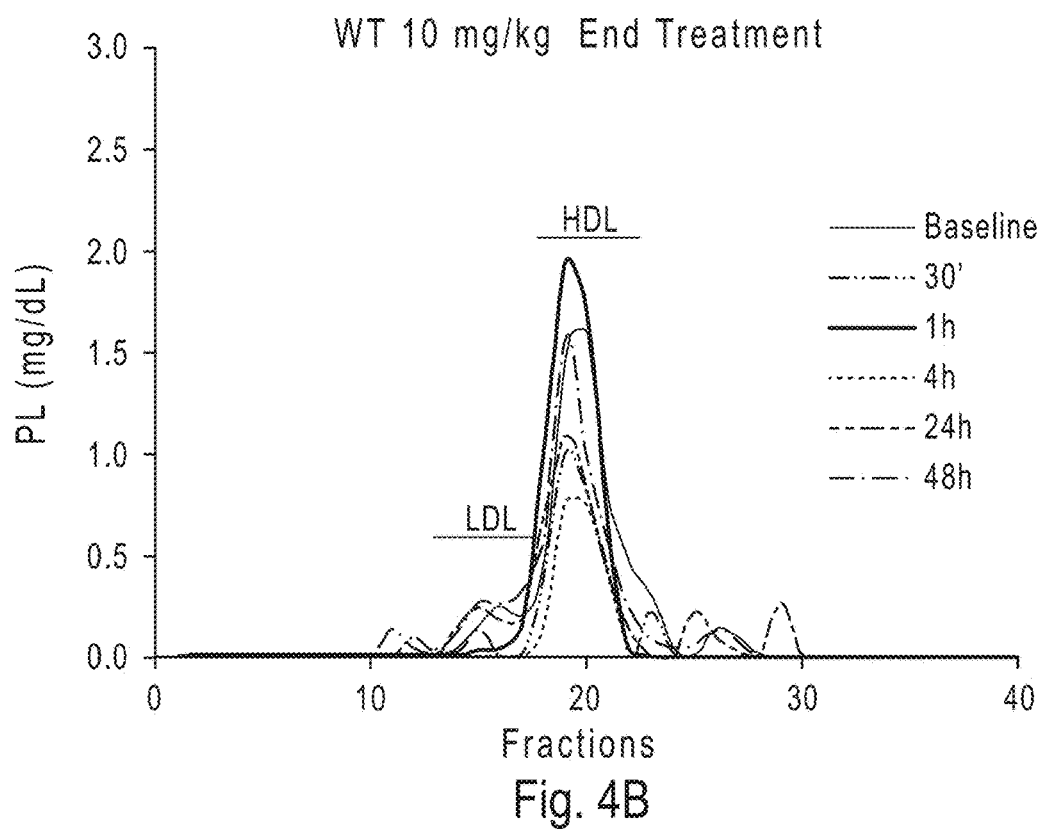

Referring to FIGS. 4A-4B, phospholipid content in the HDL region significantly increased in the 30 minutes/1 hour after the first injection in WT mice. Interestingly, this effect was not observed after the last injection and the phospholipid distribution in lipoprotein at the end of treatment did not show marked differences compared to baseline, despite the reduction observed in HDL peak after 4 and 24 hours after the last injection.

Figure 5A:
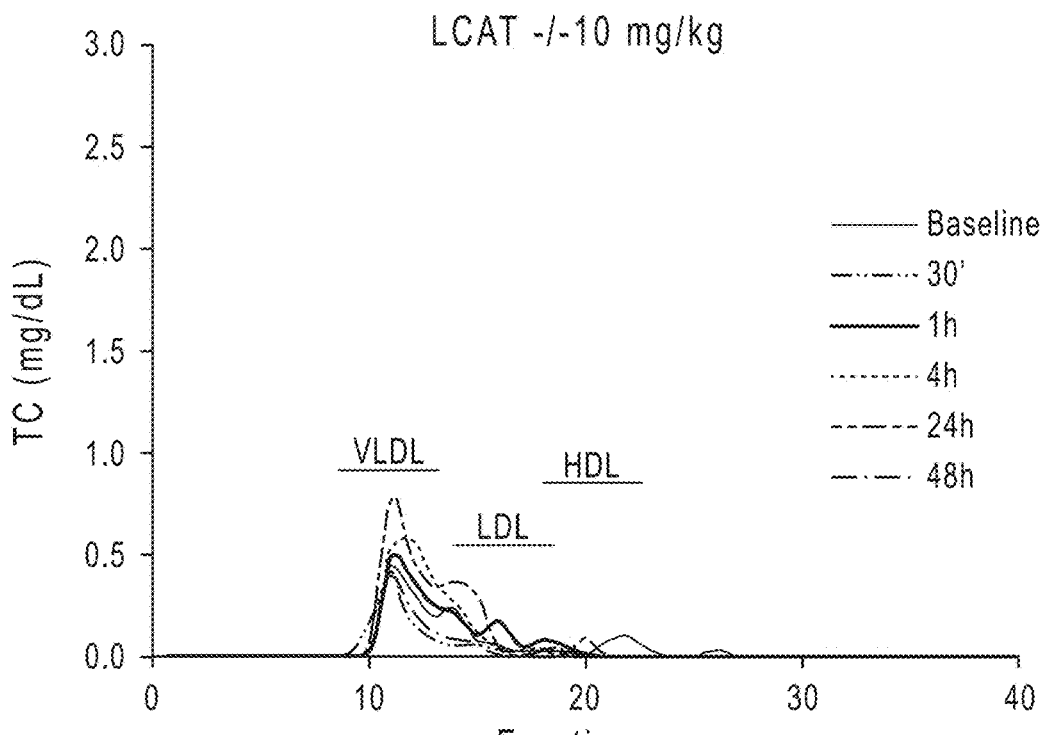
FIGS. 5A-5B are graphs showing the total cholesterol distribution obtained in LCAT deficient mice after treatment with CER-001 at 10 mg/kg after the first injection (FIG. 5A) and at the end of treatment (FIG. 5B) in the study described in Example 3.
Figure 5B:
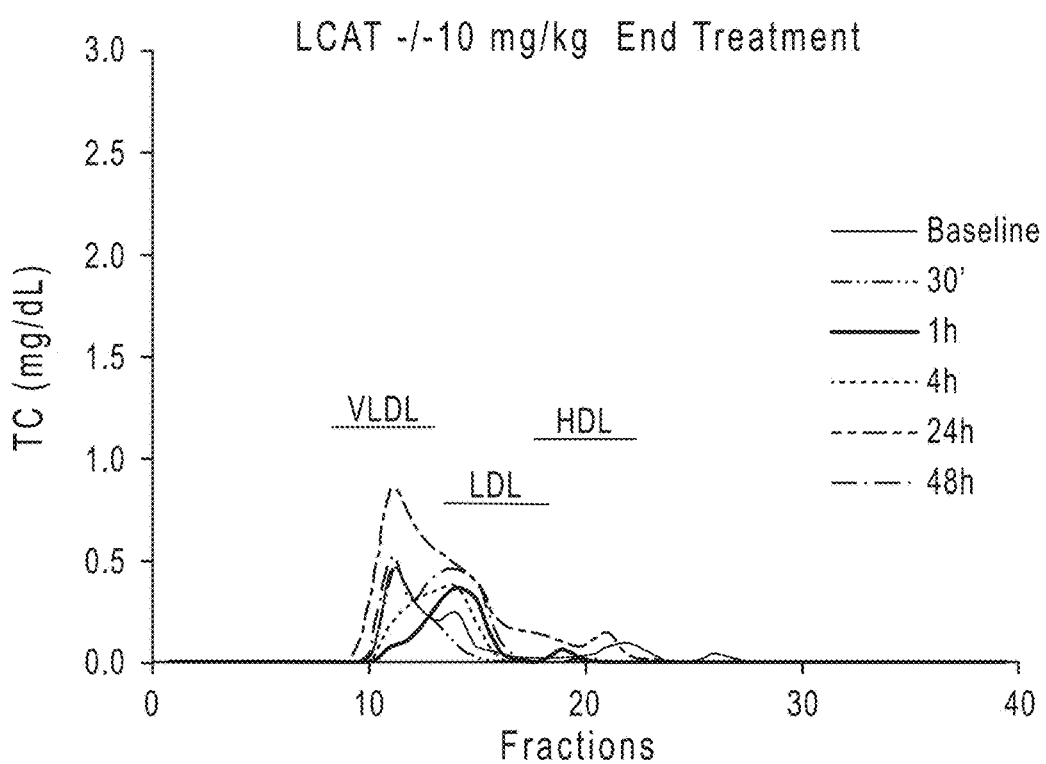

Referring to FIGS. 5A-5B, LCAT−/− mice displayed a different FPLC profile compared to WT mice, characterized by the total lack of peak in the HDL region. Most of the cholesterol was concentrated in the VLDL region and cholesterol distribution did not change after CER-001 administration.

Figure 6A:
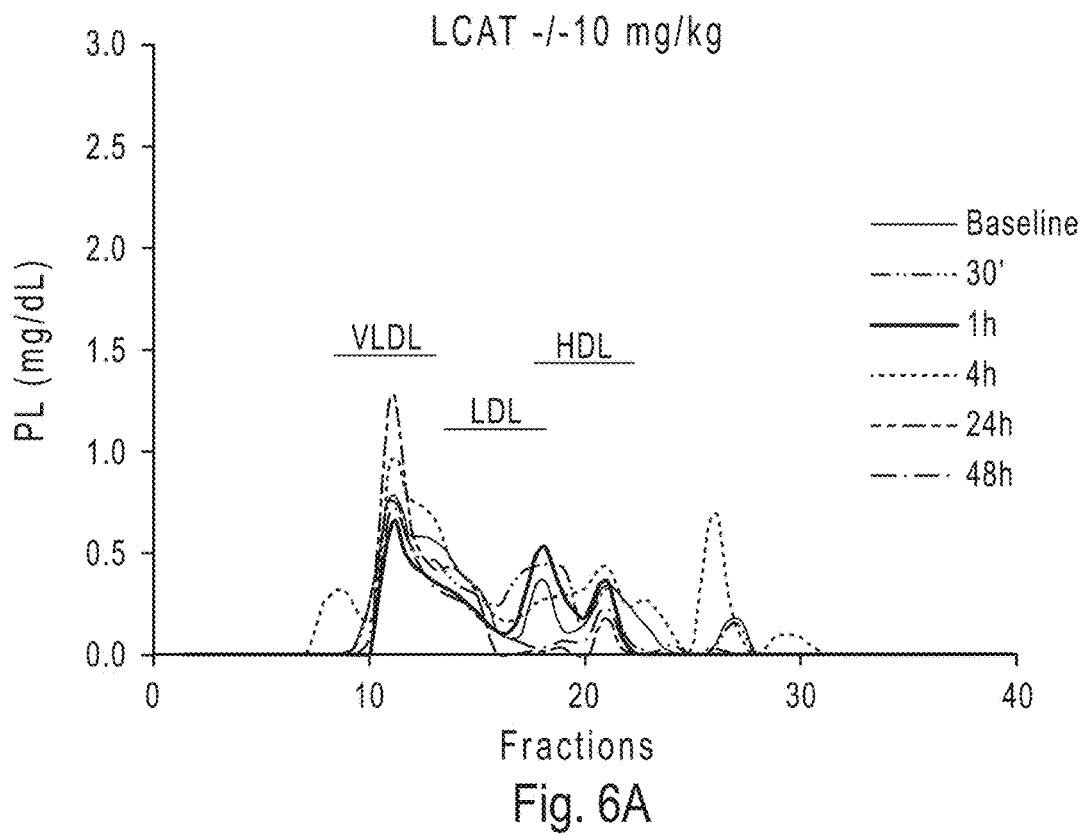
FIGS. 6A-6B are graphs showing the phospholipid content obtained in LCAT deficient mice after treatment with CER-001 at 10 mg/kg after the first injection (FIG. 6A) and at the end of treatment (FIG. 6B) in the study described in Example 3.
Figure 6B:
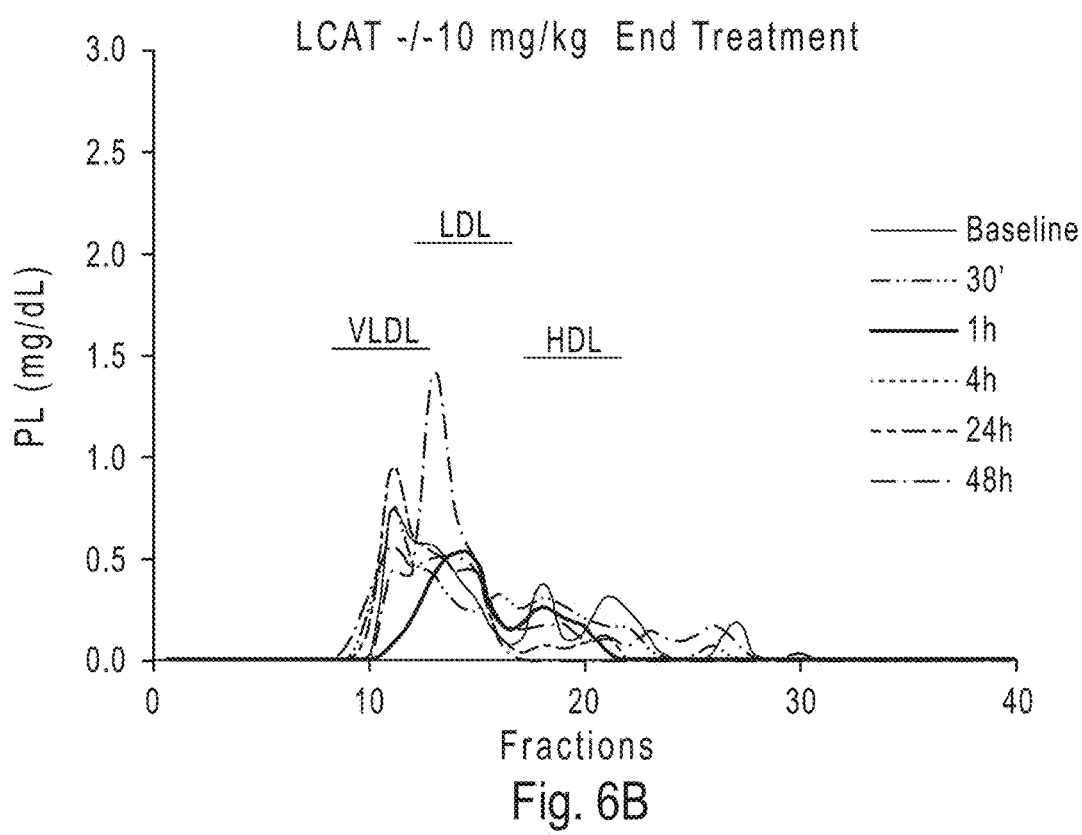

Referring to FIGS. 6A-6B, a transitory increase in VLDL/LDL peak was observed 4/24 hours after CER-001 administration that returned to baseline 48 hours after the injection.

Figure 7A:
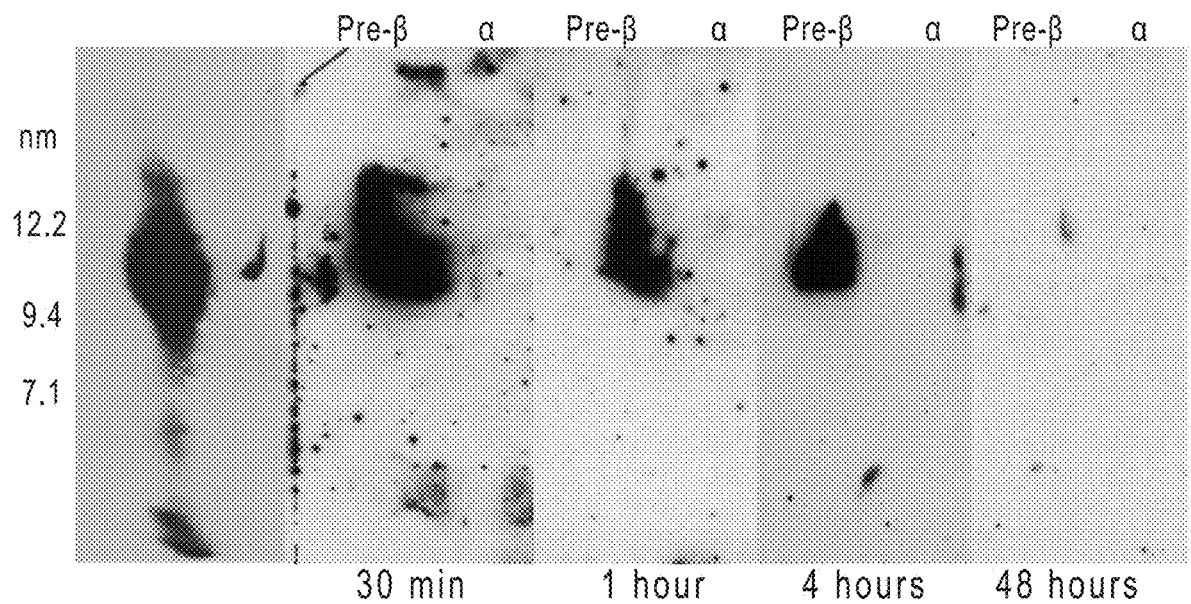
FIGS. 7A-7B show 2D-electrophoretic analyses of HDL followed by immunodetection of CER-001. CER-001 was injected at 10 mg/kg in wild-type (FIG. 7A) and LCAT deficient mice (FIG. 7B), and blood was collected after 30 minutes, 1 hrs, 4 hrs, 24 hrs, and 48 hrs as described in Example 3.
Figure 7B:
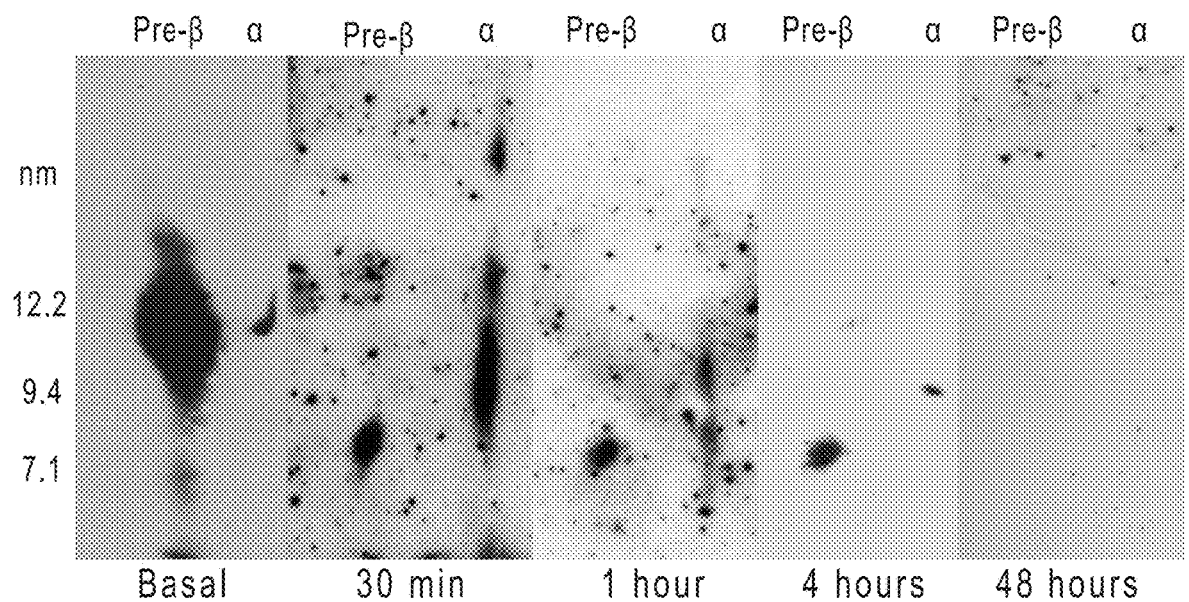

Referring to FIG. 7A, as shown by 2D electrophoretic analysis, CER-001 appeared as a large discoidal particle migrating in pre-β position and when injected in wild-type mice the particle was detectable as unchanged until 4 hours (detected as human apoA-I) after administration, and disappeared thereafter, whereas referring to FIG. 7B in LCAT−/− mice, CER-001 was weakly detectable in pre-β position 30 minutes after administration and completely disappeared 4 hours after injection.

Figure 8A:
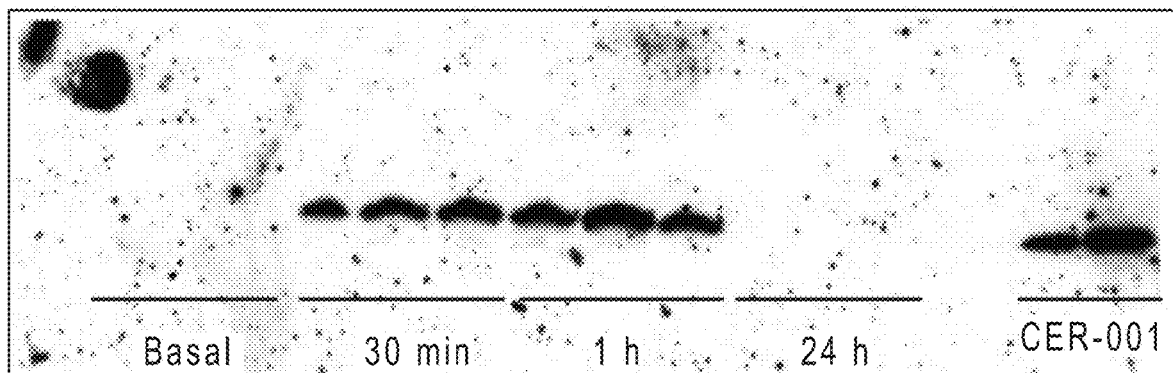
FIGS. 8A-8B show Western blot analyses detecting CER-001 in kidney (FIG. 8A) and liver (FIG. 8B) of LCAT deficient mice collected before, 30 minutes, 1 hour, and 24 hours after CER-001 administration as described in Example 3.
Figure 8B:
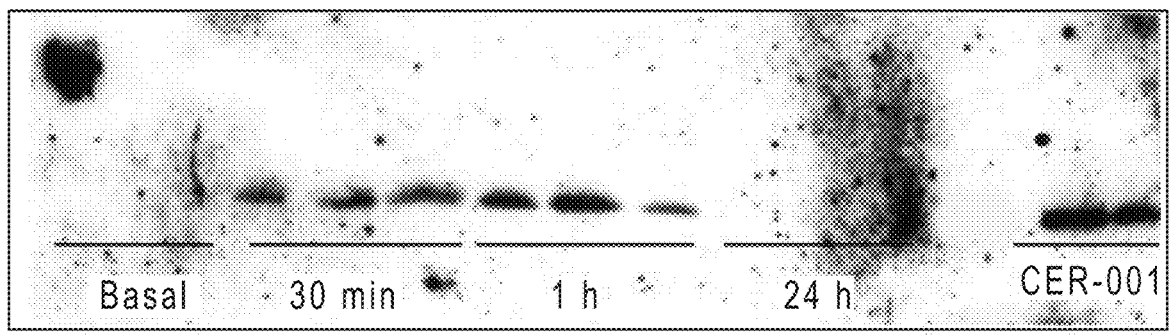

Referring to FIGS. 8A-8B, to investigate the rapid catabolic fate of CER-001 in absence of LCAT, the presence of CER-001 in the kidneys (FIG. 8A) and livers (FIG. 8B) of LCAT−/− mice collected before, and 30 minutes, 1 hour, and 24 hours after CER-001 administration was analyzed by Western blot analysis. CER-001 was detected principally in the kidney and to a lesser extent in liver 30 minutes and 1 hour after injection, and the signal completely disappeared 24 hours later.

Figure 9:
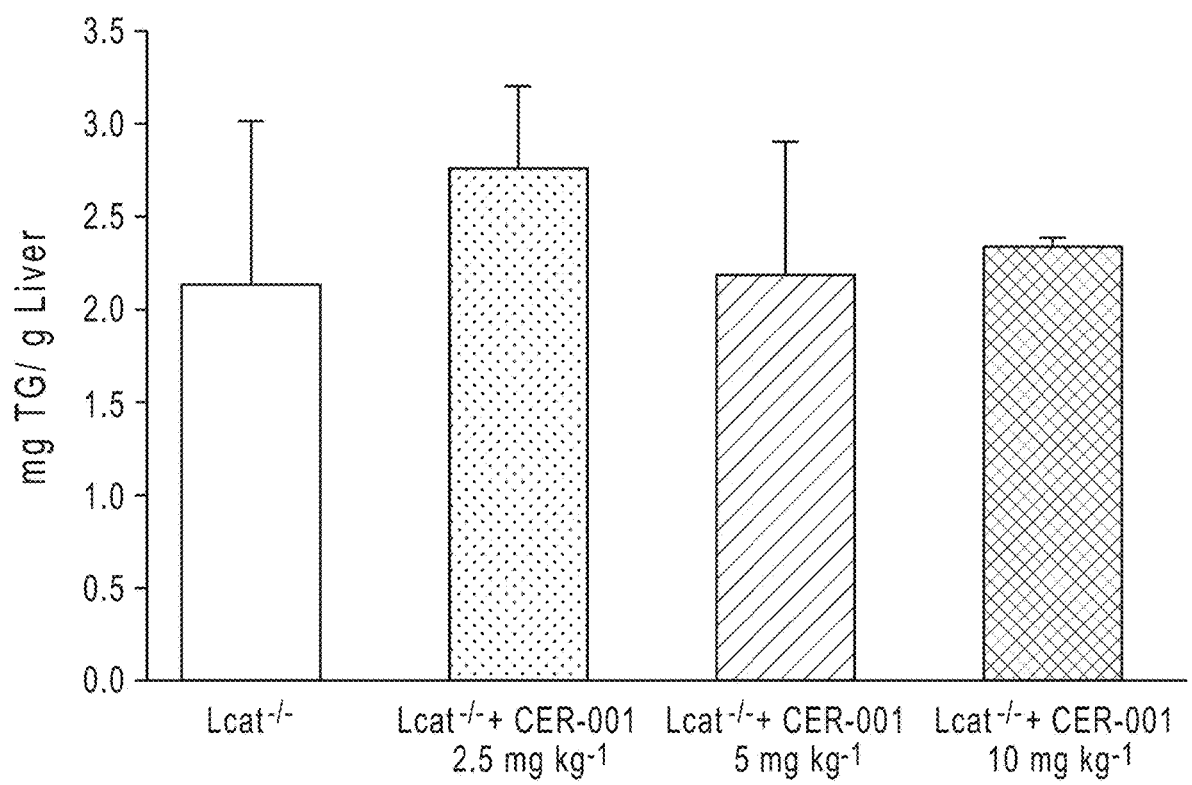
FIG. 9 is a graph showing the triglyceride content in livers of LCAT deficient mice after treatment with CER-001 as described in Example 3.

Referring to FIG. 9, to confirm that triglycerides did not accumulate in livers of LCAT−/− mice, the total content of hepatic triglycerides was analyzed in animals treated with 2.5 mg/kg, 5 mg/kg and 10 mg/kg CER-001. LCAT−/− mice did not show any difference compared to untreated mice.

Figure 10A:
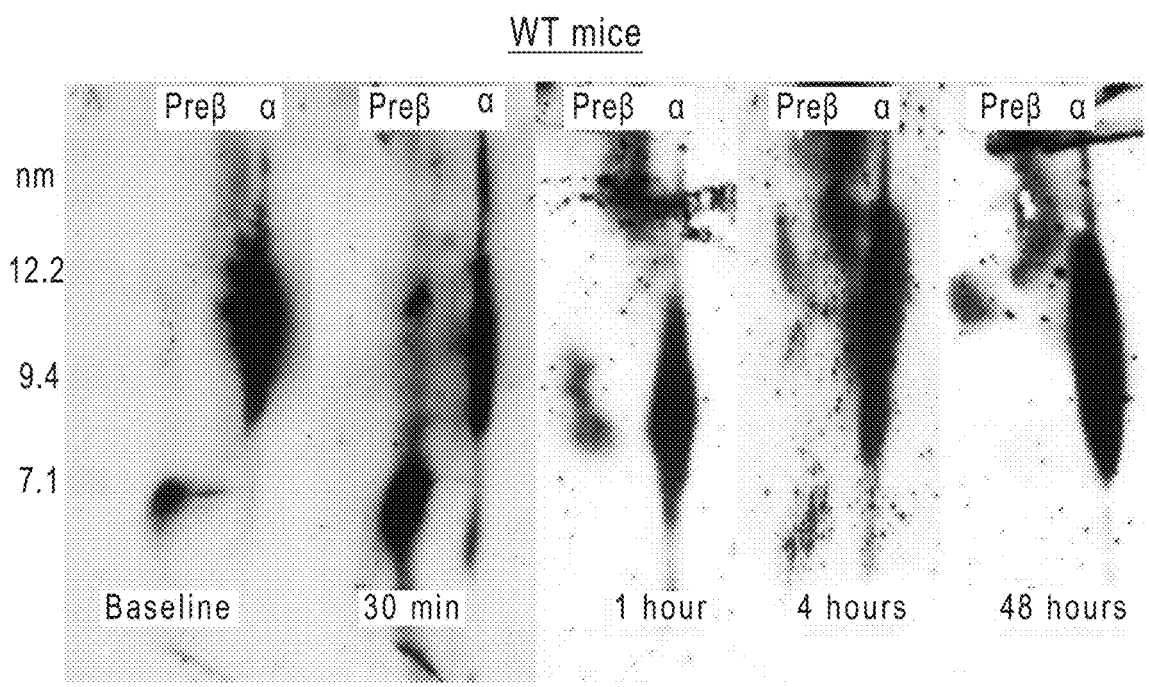
FIGS. 10A-10B are representative images of HDL subclasses in LCAT -/- (FIG. 10B) and wild type (WT) (FIG. 10A) mice after treatment with CER-001 at 10 mg/kg in the study described in Example 3.
Figure 10B:
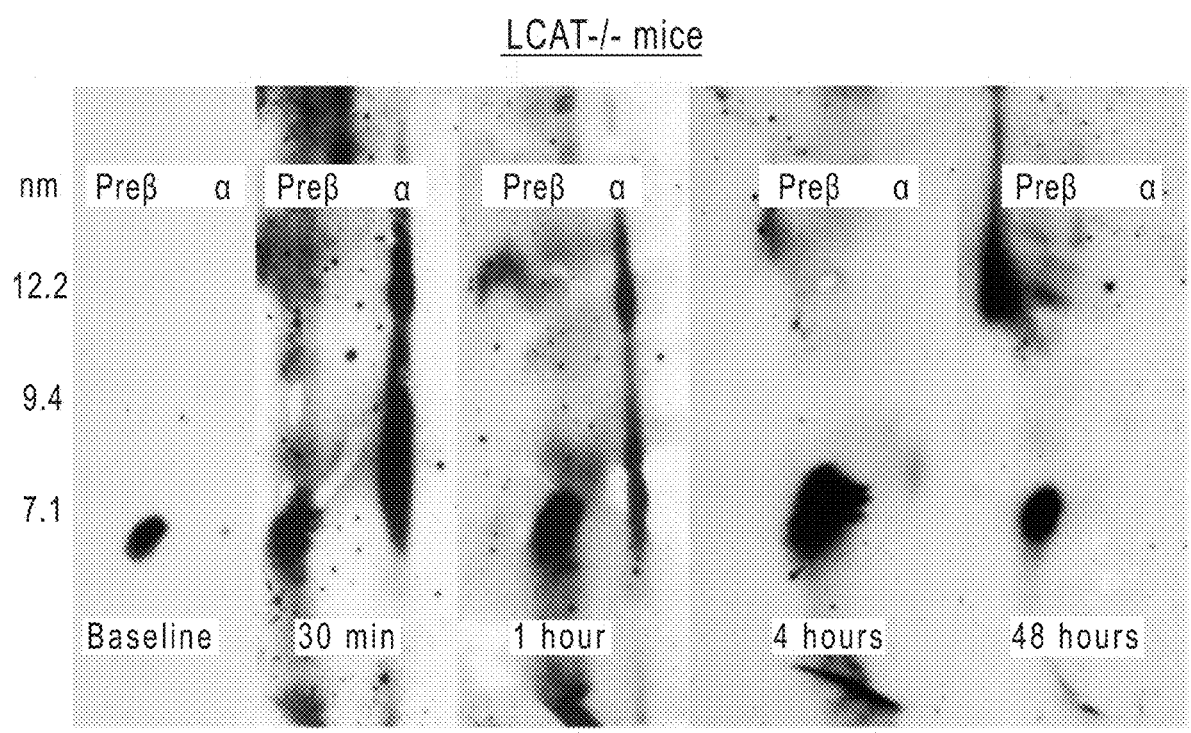

HDL subclasses distribution according to surface charge and size was assessed by 2D electrophoresis analysis followed by immunodetection against apoA-I (see Franceschini et al., 2013, J. Clin. Lipidol. 7:414-422). This technique allows the separation of the small, discoidal HDL (preβ-HDL) from the large, spherical and mature particles (α-HDL). FIGS. 10A-10B show representative images of HDL subclasses in LCAT−/− (FIG. 10B) and WT (FIG. 10A) mice treated at the highest dose (10 mg/kg). As can be seen in FIGS. 10A-10B, 30 minutes after CER-001 injection, the majority of the apoA-I signal was detectable in preβ-HDL; notably, this signal disappeared at 1 hour after injection. This was likely due to LCAT reaction that allowed the maturation of preβ-HDL into α-HDL. Later after injection (4 and 48 hours), a shift of apoA-I signal towards α-HDL of larger size was also detectable. At baseline, LCAT−/− mice show the typical absence of α-HDL, and only preβ-HDL could be detected. Earlier after CER-001 injection (30 min/1 hour) the signal of apoA-I in prep was enhanced and a small signal in α-HDL appeared. At 4 hours after injection the apoA-I signal in prep was still enhanced, but it returned comparable to baseline levels 48 hours later.

To verify the potential accumulation of apoA-I in kidney, urine samples were collected during the last 24 hrs after the last injection and kidneys were analyzed at the end of the study to assess the presence of human apoA-I (hapoA-I) by immunodetection (see Gomaraschi et al., 2013, Biochem Pharmacol. 85:525-530). No hapoA-I was detected in kidneys and urine of both WT and LCAT−/− treated animals.

The results of this study clearly show that the absence of LCAT modifies the remodeling of CER-001 when injected in mice. In WT mice, the injected particles enter the classical HDL remodeling pathway, being converted into larger particles. In LCAT−/− mice the injected particles cannot be converted, but interestingly they do not accumulate in plasma and not in the kidney. Changes observed in plasma lipids clearly show that CER-001 injection leads to an amelioration of the lipid profile in WT and LCAT−/− mice, with a general decrease in total cholesterol and triglycerides, and an increase in HDL-C, particularly evident in LCAT−/− mice characterized by a dramatic HDL defect. Finally, results observed after CER-001 injection differ from what we observed after injection in the same animal models of reconstituted HDL (rHDL) made of phosphatidylcholine, apoA-I, and cholesterol (data not shown); specifically, the injection of rHDL produces a significant increase in plasma triglycerides, as also shown in other animal models with different discoidal particles (see Kempen et al., 2013, J Lipid Res 54:2341-2353). Interestingly, the results described in this Example showed that there is no accumulation of CER-001 in the kidney, as well as no detectable human apoA-I in urine of treated animals.

5.4 Example 4: CER-001 Remodeling and Effects on Kidney in LCAT Deficiency

The aim of the study was to evaluate the effects of CER-001 on kidney disease associated with LCAT deficiency.

Three groups of animals were used in the study:

LCAT −/− mice (see Manzini et al., 2015, Vascul Pharmacol 74:114-121)

LCAT −/− mice injected with LpX as a model of renal disease (see Ossoli et al., 2016, *PlosOne* 11:e0150083)

WT mice

Figure 11:
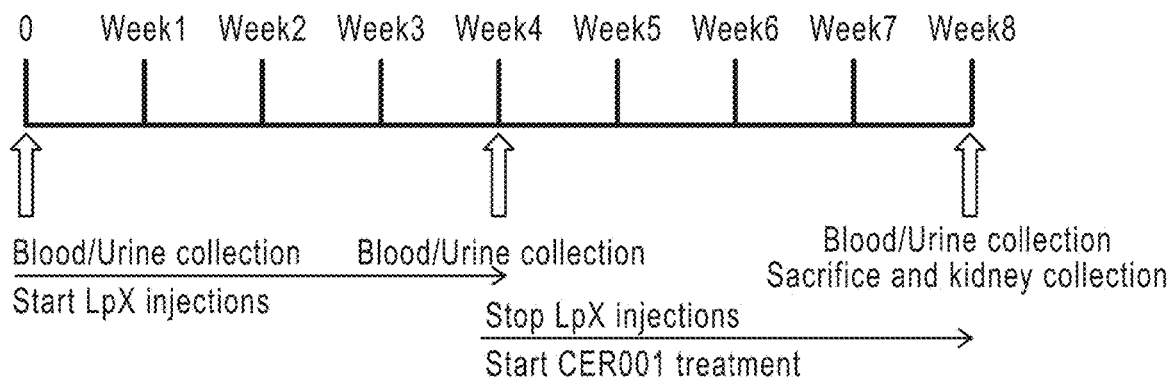
FIG. 11 shows the design of the study described in Example 4.

A mouse model of renal disease was created by 1-month injections of LpX in LCAT −/− mice at 8 to 9 months of age as previously described (see, Ossoli et al., 2016, *PlosOne* 11:e0150083). To evaluate the capacity of CER-001 infusion to reverse renal disease, LCAT −/− LpX-injected mice were treated at 9 to 10 months of age with 1-month injections of CER-001 (2.5, 5, and 10 mg/kg) 3 times a week. Control group mice (LCAT −/− LpX-injected mice) received the same volume amount of saline solution (FIG. 11).

Plasma Lipid Profile

Figure 12:
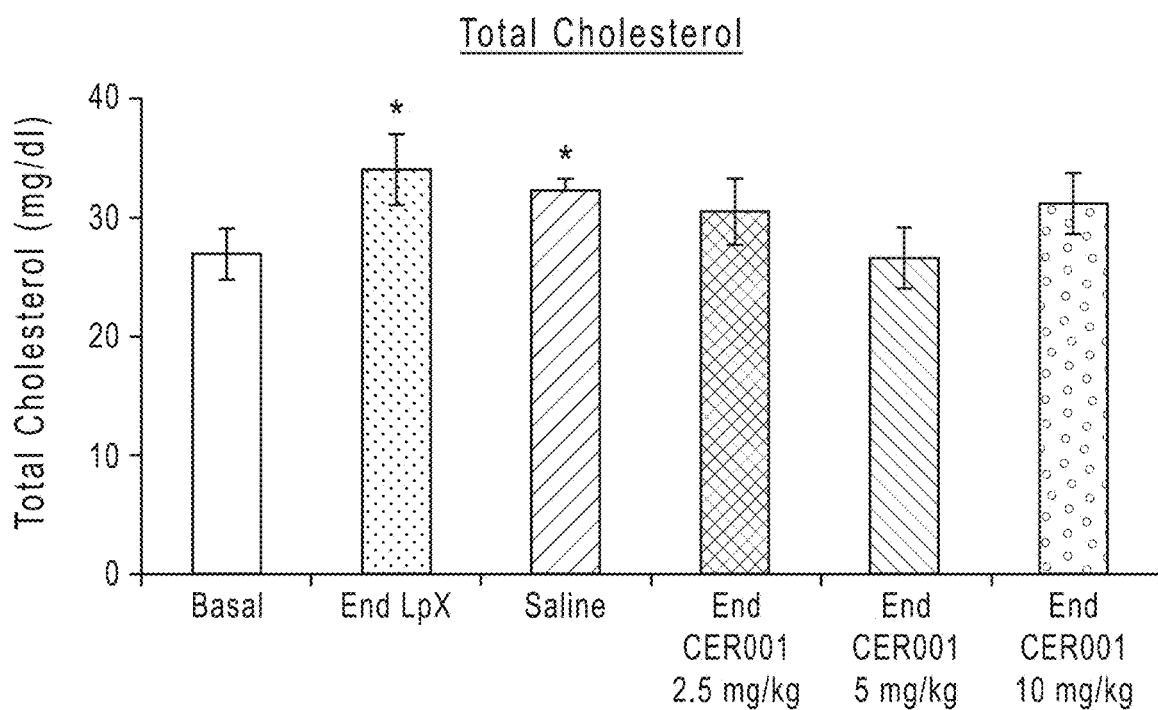
FIG. 12 is a graph showing plasma cholesterol level in LCAT -/- mice in the study described in Example 4.

Plasma lipids and lipoproteins were analyzed before starting treatment, after LpX treatment, and at the sacrifice. Referring to FIG. 12 (Data are mean±SEM. *P<0.05 vs basal level), plasma total cholesterol levels increased after LpX administration, the treatment with CER-001 slightly decreased plasma total cholesterol levels, which returned comparable to basal values.

TABLE 5

| | Basal | End LpX | End Saline | End CER001 2.5 mg/kg | End CER001 5 mg/kg | End CER001 10 mg/kg |
|---|---|---|---|---|---|---|
| Plasma lipid Profile | | | | | | |
| Total cholesterol (mg/dL) | 26.9 ± 2.2 | 34.0 ± 3.0* | 32.1 ± 1.2* | 30.5 ± 2.8 | 26.6 ± 2.6 | 31.2 ± 2.6 |
| Unesterified cholesterol (mg/dL) | 21.0 ± 1.8 | 26.2 ± 3.0 | 23.7 ± 1.0 | 25.8 ± 2.6 | 20.3 ± 2.3 | 27.4 ± 3.2 |
| Esterified cholesterol (mg/dL) | 14.0 ± 3.1 | 12.9 ± 0.9 | 12.4 ± 1.1 | 8.0 ± 1.9§ | 10.6 ± 1.1 | 10.0 ± 1.3 |

Data are mean ± SEM.
*P < 0.05 vs basal level.
§P < 0.05 vs LpX

Figure 13:
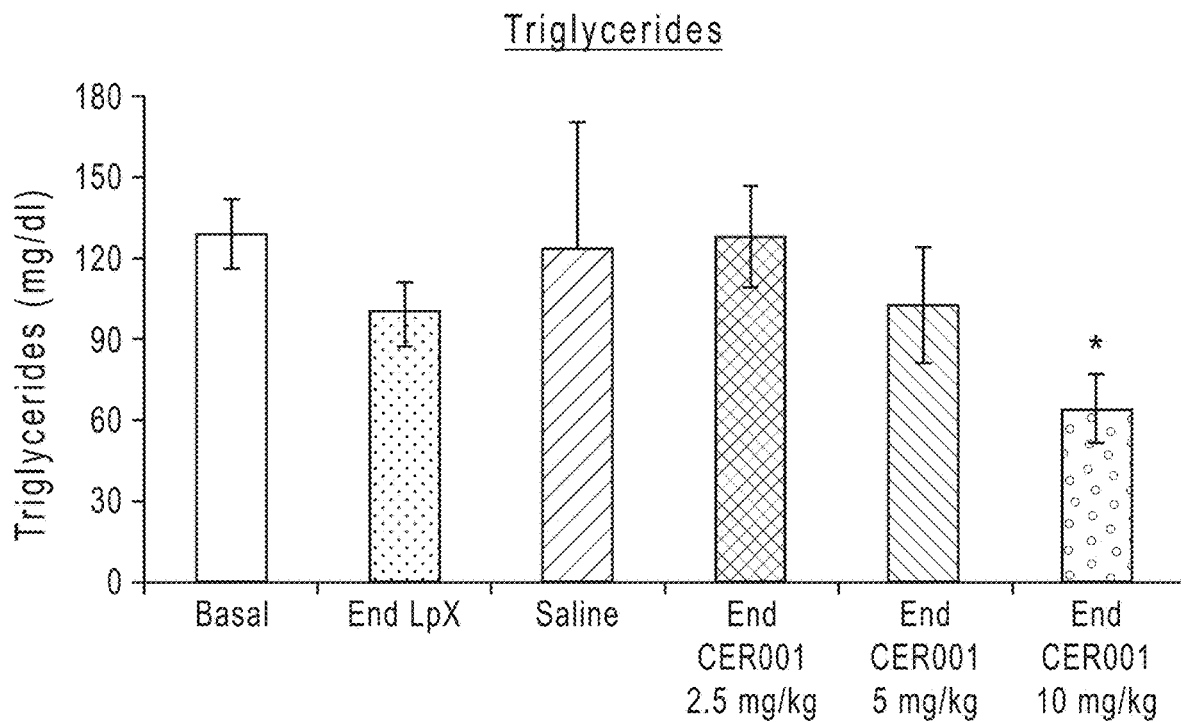
FIG. 13 is a graph showing plasma triglycerides level in LCAT -/- mice in the study described in Example 4.

Referring to FIG. 13 (Data are mean±SEM. *P<0.05 vs basal level), the treatment with LpX did not alter plasma triglycerides level; after treatment with CER-001 at the highest dose (10 mg/kg) triglycerides were significantly reduced, confirming also in this condition, the results observed in Example 3 above.

Figure 14:
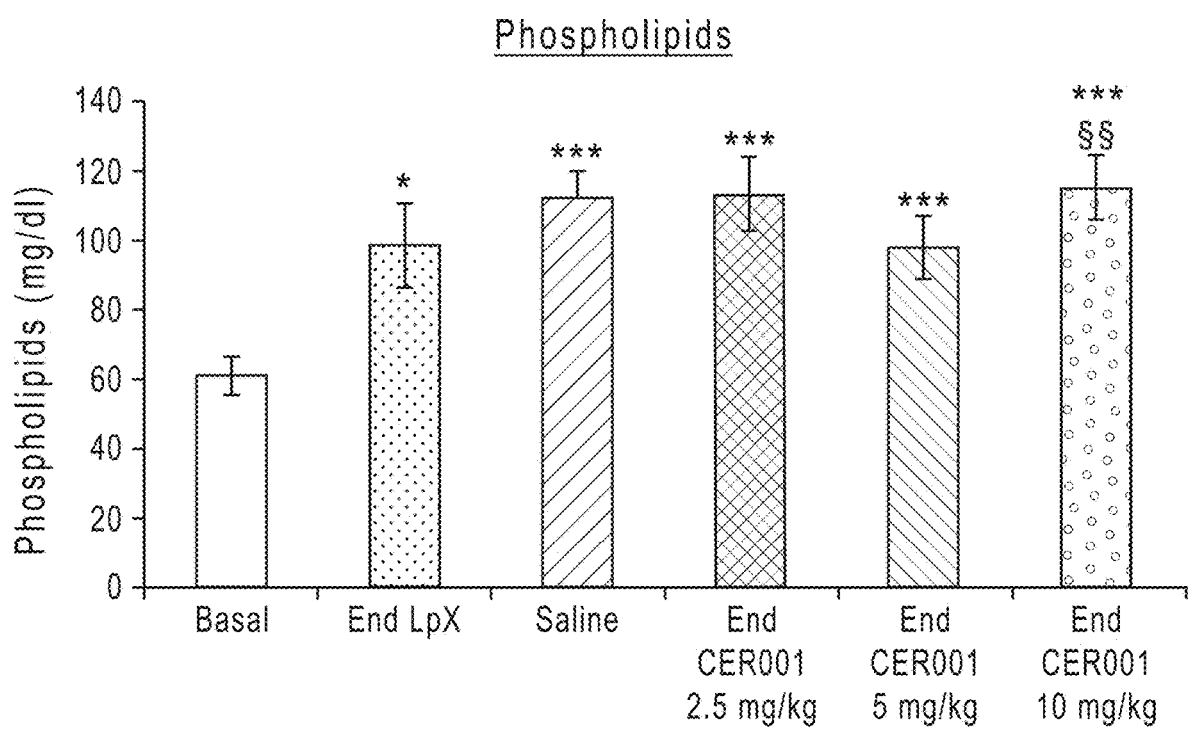
FIG. 14 is a graph showing plasma phospholipids level in LCAT -/- mice in the study described in Example 4.

Referring to FIG. 14 (Data are mean±SEM. *P<0.05, P<0.01 and *P<0.001 vs basal level, §§ P<0.01 vs LpX) plasma phospholipids (measured as phosphatidylcholine) significantly increased after LpX treatment; the treatment with CER-001 did not reverse this condition. This result is in contrast with those obtained in Example 3 above, where we observed a reduction of phosphatidylcholine.

Figure 15:
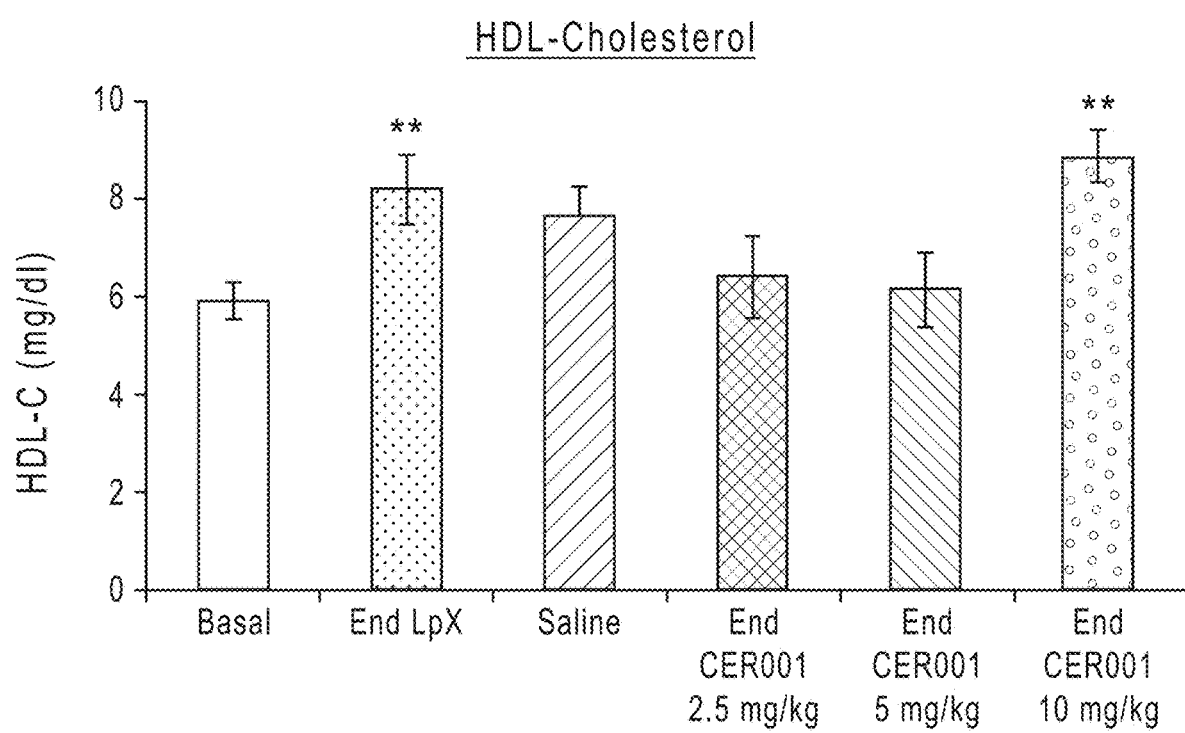
FIG. 15 is a graph showing plasma HDL-C level in LCAT-/- mice in the study described in Example 4.

Referring to FIG. 15 (Data are mean±SEM. *P<0.01 vs basal level) as previously reported (see Ossoli et al., 2016, PlosOne 11:e0150083), the formation of a small HDL particle in LCAT−/− mice after LpX administration was observed that can explain the increased HDL-C levels after LpX treatment. Increased HDL-C levels were also observed at the end of treatment with CER-001 at highest dose (10 mg/kg).

Figure 16A:
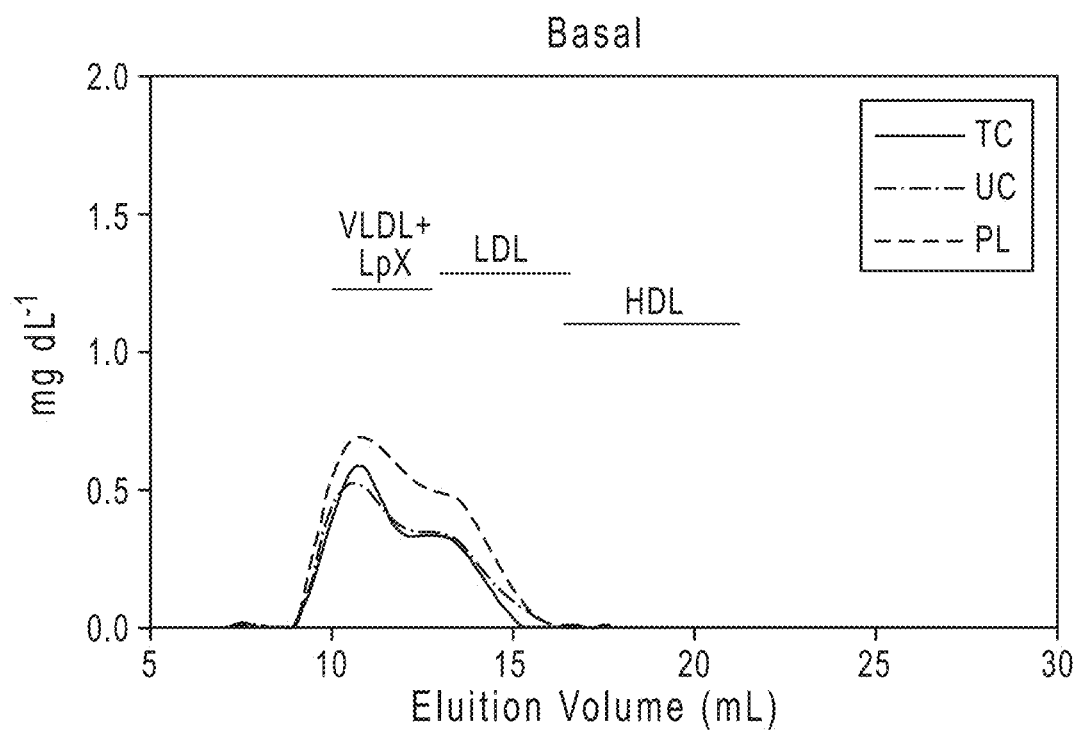
Figure 16B:
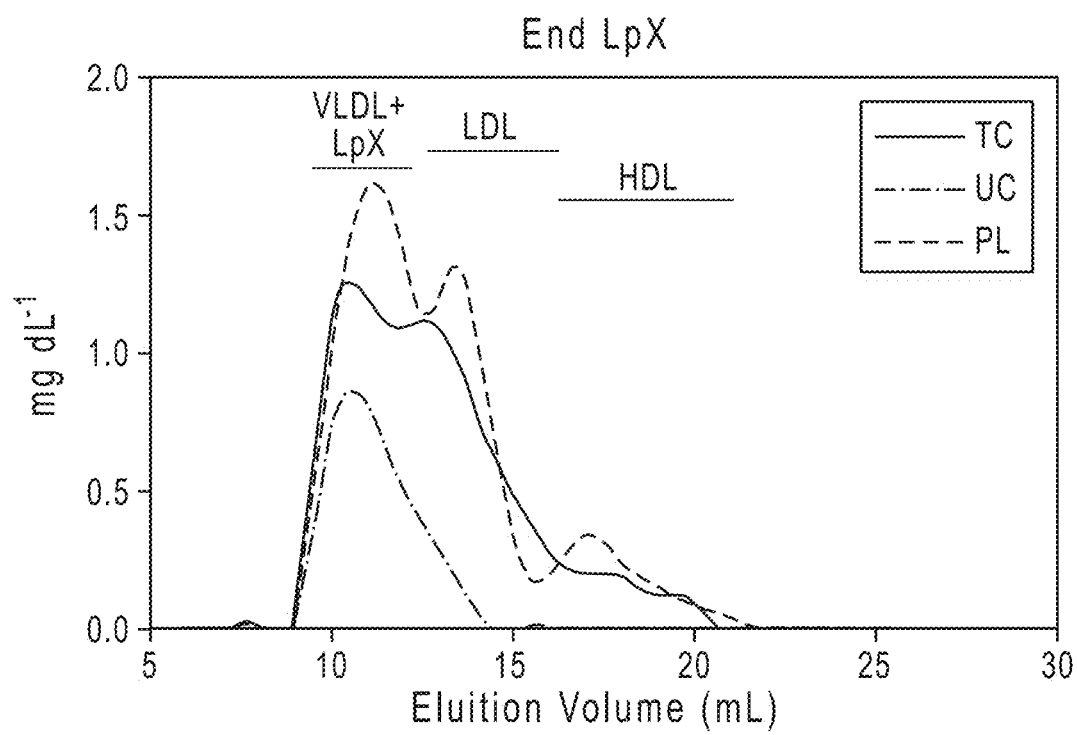
Figure 16C:
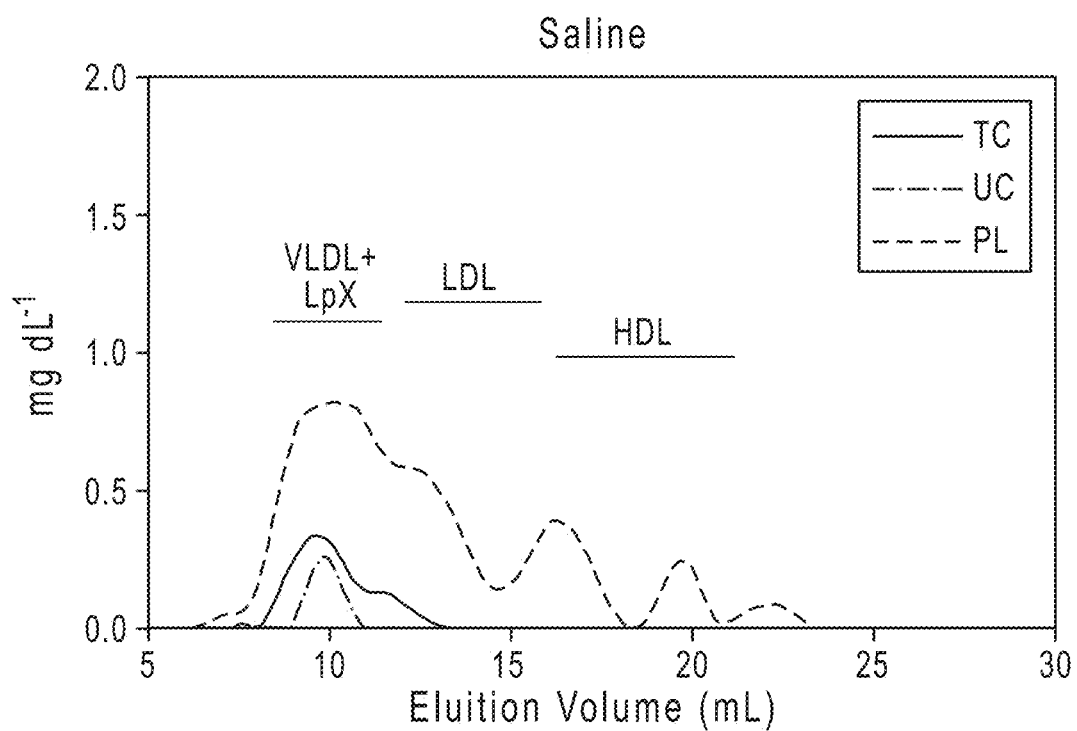
Figure 16D:
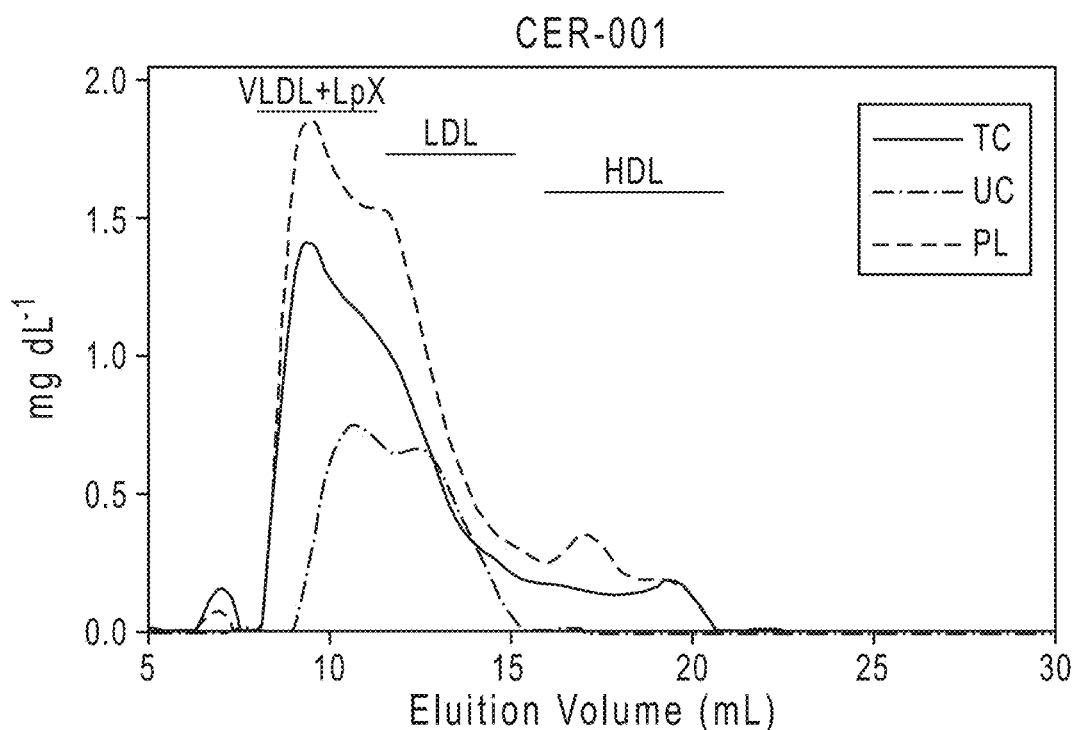

Referring to FIG. 16D, the analysis of plasma lipoproteins by FPLC showed the presence of a peak of phospholipids in the VLDL/LpX fraction at the end of CER-001 treatment; however, referring to FIG. 16B, this peak was shifted towards particles of larger size compared to the one present after LpX injection. On the contrary, referring to FIG. 16C C, the phospholipid profile returned similar to baseline in mice that received saline.

Referring to FIGS. 17A-17B, the increase in phospholipids observed after CER-001 treatment is likely due to the ability of CER-001 to remove lipids (cholesterol and phospholipids) from glomeruli of treated mice.

Referring to FIG. 18, the increase in phospholipids observed after CER-001 treatment is likely due to be specifically from podocytes after LpX loading.

Referring to FIG. 19 the removed lipids are assembled in large particles, detectable in the VLDL region but with reduced content of triglycerides.

Renal Function Evaluation

Renal function was evaluated as microalbumin to creatinine ratio in urine by ELISA and colorimetric assay, and by measuring plasma blood urea nitrogen before starting treatment, after LpX treatment and at the sacrifice. Referring to FIG. 20 (Data are mean±SEM. P<0.01 and *P<0.001 vs basal level, §§ P<0.01 vs LpX) as already reported, BUN levels were not altered after LpX treatment (see Ossoli et al., 2016, PlosOne 11:e0150083); at the end of treatments with saline or CER-001 a reduction of BUN level was observed in all groups. Referring to FIG. 21 (Data are mean±SEM. **P<0.01 vs basal level, §§ P<0.05 vs LpX; results of 2.5 mg CER-001 are not available), consistent with data previously reported (see Ossoli et al., 2016, PlosOne 11:e0150083), LCAT−/− mice injected with LpX showed a more than two-fold increase in the urine μg albumin/mg creatinine ratio (UACR). A significant reduction of UACR was observed only in mice treated with CER-001 at the highest dose (10 mg/Kg), suggesting an improvement of renal function after treatment.

ApoA-I and ApoB in Kidney

To verify the potential accumulation of apoA-I and apoB in kidney, urine samples were collected during the last 24 hours after the last injection and kidneys were analyzed at the end of the study. The presence of human apoA-I (hapoA-I) and mouse apoB (mapoB) was immunodetected (see Gomaraschi et al., 2013, Biochem Pharmacol. 85:525-530). No hapoA-I and mapoB were detected in kidneys and urine in treated animals of all groups.

Histological Analysis of Kidney

At the end of treatments, animals were sacrificed and kidneys were collected for histological analysis. Mesangial matrix expansion was evaluated in three micrometer sections stained with periodic acid-Schiff (PAS) reagent, and at least 50 glomeruli were examined for each animal. The degree of glomerular matrix expansion was quantified using a score from 0 to 3 (0=no mesangial matrix expansion; 1=minimal; 2=moderate; 3=diffuse mesangial matrix expansion). Biopsies were analyzed by the same pathologist who was unaware of experimental groups.

Referring to FIG. 22 (data are mean±SD) mild mesangial matrix expansion was observed in mouse kidney of all groups at the end of treatments, with no differences among treatments. Similar mesangial matrix expansion was reported in LCAT−/− mice treated with LpX alone (0.9±0.2) and sacrificed 24 hours after last injection (see Ossoli et al., 2016, PlosOne 11:e0150083). Tubular analysis was also performed and highlighted a minimal vacuolization only in two mice (one treated with saline and one treated with 2.5 mg/kg CER-001) not correlated at glomerular alterations.

Ultrastructural Analysis of Kidney

Fragments of cortical kidney tissue were fixed overnight in 2.5% glutaraldehyde in 0.1 M cacodylate buffer and washed repeatedly in the same buffer. After postfixation in 1% OsO4, specimens were dehydrated through ascending grades of alcohol and embedded in Epon resin. Ultrathin sections were stained with uranyl acetate replacement (UAR-EMS) and lead citrate and examined using a Philips Morgagni electron microscope. The analysis was performed in mice treated with saline solution and in mice treated with CER-001 at the highest dose (10 mg/kg).

As can be seen in FIG. 23, in both groups ultrastructural alterations typical of renal disease in LCAT deficiency (see Santamarina-Fojo et al In: Scriver C R, Beaudet A L, Sly W S, Valle D, editors. The Metabolic and Molecular Bases of Inherited Diseases. New York: McGraw-Hill; 2001. p. 2817-33) and already described after LpX administration (see Ossoli et al., 2016, *PlosOne* 11:e0150083) were observed. These alterations include formation of irregular lucent lacunae containing membrane-like lamellar osmiophilic dense inclusions in the glomerular basement membranes (GBM), electron dense deposits and dense areas in the mesangium, a thickened GBM and podocytes focal foot process effacement. The treatment with CER-001 apparently did not modify pattern and entity of ultrastructural alterations.

Lipid modifications observed after treatment with CER-001 in mice previously injected with LpX were clearly different from changes observed in Example 3 above. Specifically, total cholesterol and phospholipid did not decrease.

As shown in Example 3 above, CER-001 did not accumulate in kidney of treated animals. Treatment with CER-001 at the highest dose (10 mg/kg) promoted an amelioration of renal function measured as UACR. However, the ultrastructural analysis carried out on kidneys at the sacrifice did not show significant changes in CER-001 treated mice.

Renal Function Evaluation

In addition to measurement of microalbumin to creatinine ratio in urine plasma blood urea nitrogen, the expression of nephrin in kidney was assessed by immunofluorescence before treatment, after LpX injection, and after CER-001 (10 mg/kg) treatment. Nephrin is a relevant protein in podocyte functionality. The podocyte is a highly specialized epithelial cell endowed with foot processes, which constitutes a crucial component of the glomerular filtration barrier. Neighboring foot processes are bridged by slit diaphragms, specialized intracellular junctions with filtration slits formed by nephrin and nephrin-like protein 1 that act to maintain slit pore integrity and renal filtration capacity. As shown in the FIG. 24, in LpX-treated LCAT−/− mice a reduction in the signal intensity of nephrin was observed, compared with LCAT−/− mice receiving saline. The nephrin expression significantly increased after treatment with CER-001 at 10 mg/kg, suggesting that the treatment was able to reverse podocyte damage.

The quantification of nephrin expression, using a score, confirmed the results as reported in FIG. 25. Treatment with CER-001 at the highest dose (10 mg/kg) promoted an amelioration of renal function measured as microalbumin to creatinine ratio in urine, associated to an increased nephrin expression.

In addition to measurement of microalbumin to creatinine ratio in urine plasma blood urea nitrogen and the expression of nephrin in kidney, the expression of nestin was assessed after LpX injection and after CER-001 (10 mg/kg) treatment. Nestin is a cytoskeleton-associated filament protein expressed in fully differentiated podocytes. Since nestin has been reported to interact with all three classes of cytoskeletal proteins, it is involved in the organization of the cellular cytoskeleton and also play an important role in the maintenance of normal podocyte function. As shown in the FIG. 26, in LpX-treated LCAT−/− mice a reduction in nestin expression was observed, compared with LCAT+/+ mice. The nestin expression increased after treatment with CER-001 at 10 mg/kg, suggesting that the treatment was able to reverse podocyte damage and recover podocyte function. The quantification of nestin expression, using a score, confirmed the results as reported in FIG. 27.

Lipid Content in the Kidney

The content of unesterified cholesterol and phospholipids was measured in the kidney of treated mice. The content of unesterified cholesterol slightly decreased after treatment with CER-001 at the highest dose (10 mg/kg), while the total content of phospholipids increased after treatment, probably due to the high content of phospholipids injected with CER-001 (FIGS. 28A-28B). Treatment with CER-001 at the highest dose (10 mg/kg) promoted an amelioration of renal function measured as microalbumin to creatinine ratio in urine, associated to an increased nephrin and nestin expression. CER-001 was also able to slightly reduce the content of unesterified cholesterol in the kidney.

Discussion

The study of this Example shows for an amelioration of the lipid/lipoprotein profile in Lcat$^{-/-}$ mice treated with CER-001, and an improvement of renal function after CER-001 treatment in a mouse model of renal disease in LCAT deficiency. Moreover, the study supports the use of CER-001 as a treatment of kidney disease.

6.5. Example 5: Treatment of Subjects with LCAT Deficiency

Subjects with an LCAT deficiency (partial or full) suffering from glomerulopathy are administered CER-001 according to a treatment regimen comprising an induction regimen, a consolidation regimen, and a maintenance regimen.

The induction regimen comprises nine doses of CER-001 administered over three weeks, with the first dose administered on day 1, and subsequent doses administered on days 1, 2, 4, 7, 9, 11, 14, 16, and 18. The dose of CER-001 administered in the induction regimen is 10 mg/kg, calculated based upon the amount of ApoA-I in the CER-001 to be administered and the weight of the subject.

Following the induction regimen, the subjects are administered CER-001 according to a consolidation regimen comprising six doses of CER-001 over three weeks. The induction regimen doses are administered on days 21, 24, 28, 31, 35 and 38 of the treatment. The dose of CER-001 administered in the induction regimen is 10 mg/kg, calculated based upon the amount of ApoA-I in the CER-001 to be administered and the weight of the subject.

Following the induction regiment, the subjects are administered CER-001 according to a maintenance regimen comprising once a week administration of CER-001. The duration of the maintenance regimen is subject specific and is at least one month to indefinitely. The dose of CER-001 administered in the maintenance regimen is 10 mg/kg or 20 mg/kg calculated based upon the amount of ApoA-I in the CER-001 to be administered and the weight of the subject.

In the induction, consolidation and maintenance regimens, CER-001 is administered as an IV infusion. A stock solution of CER-001 is diluted in physiological saline (0.9% NaCl) to a total volume between 125 and 250 ml. Subjects weighing less than 80 kg are administered a total volume of 125 ml per infusion whereas subjects weighing at least 80 kg are administered a total volume of 250 ml per infusion. CER-001 is administered using an infusion pump at a fixed rate of 250 ml/hr. All doses are administered at a constant infusion rate of 250 mL/h.

The treatment regimen maintains or improves kidney function in the subjects.

6.6. Example 6: Treatment Regimen for Subjects with Diabetic Nephropathy

Subjects with an diabetic nephropathy are administered CER-001 according to a treatment regimen comprising an induction regimen, a consolidation regimen, and a maintenance regimen.

The induction regimen comprises nine doses of CER-001 administered over three weeks, with the first dose administered on day 1, and subsequent doses administered on days 1, 2, 4, 7, 9, 11, 14, 16, and 18. The dose of CER-001 administered in the induction regimen is 10 mg/kg, calculated based upon the amount of ApoA-I in the CER-001 to be administered and the weight of the subject.

Following the induction regimen, the subjects are administered CER-001 according to a consolidation regimen comprising six doses of CER-001 over three weeks. The induction regimen doses are administered on days 21, 24, 28, 31, 35 and 38 of the treatment. The dose of CER-001 administered in the induction regimen is 10 mg/kg, calculated based upon the amount of ApoA-I in the CER-001 to be administered and the weight of the subject.

Following the induction regiment, the subjects are administered CER-001 according to a maintenance regimen comprising once a week administration of CER-001. The duration of the maintenance regimen is subject specific and is at least one month to indefinitely. The dose of CER-001 administered in the maintenance regimen is 10 mg/kg or 20 mg/kg calculated based upon the amount of ApoA-I in the CER-001 to be administered and the weight of the subject.

In the induction, consolidation and maintenance regimens, CER-001 is administered as an IV infusion. A stock solution of CER-001 is diluted in physiological saline (0.9% NaCl) to a total volume between 125 and 250 ml. Subjects weighing less than 80 kg are administered a total volume of 125 ml per infusion whereas subjects weighing at least 80 kg are administered a total volume of 250 ml per infusion. CER-001 is administered using an infusion pump at a fixed rate of 250 ml/hr. All doses are administered at a constant infusion rate of 250 mL/h.

The treatment regimen maintains or improves kidney function in the subjects.

7. SPECIFIC EMBODIMENTS

Various aspects of the present disclosure are described in the embodiments set forth in the following numbered paragraphs.

1. A method for treating a subject with kidney disease, comprising administering to the subject a therapeutically effective amount of CER-001.

2. The method of embodiment 1, which comprises administering CER-001 to the subject according to a maintenance regimen comprising administering a dose of CER-001 to the subject once every 3 or more days.

3. The method of embodiment 1, which comprises
   (a) administering CER-001 to the subject according to an induction regimen comprising administering at least three doses of CER-001 to the subject separated by 1 or more days; and, subsequently
   (b) administering CER-001 to the subject according to a maintenance regimen comprising administering a dose of CER-001 to the subject once every 3 or more days.

4. The method of embodiment 1, which comprises:
   (a) administering CER-001 to the subject according to an induction regimen comprising administering at least three doses of CER-001 to the subject separated by 1 or more days; and, subsequently
   (b) administering CER-001 to the subject according to a consolidation regimen comprising administering at least two doses of CER-001 to the subject separated by 2 or more days; and, subsequently
   (c) administering CER-001 to the subject according to a maintenance regimen comprising administering a dose of CER-001 to the subject once every 3 or more days.

5. The method of embodiment 3 or embodiment 4, wherein the induction regimen comprises administering at least three doses of CER-001 to the subject in one week.

6. The method of embodiment 3 or embodiment 4, wherein the doses of the induction regimen are separated by no more than three days.

7. The method of any one of embodiments 3 to 6, wherein the second and subsequent doses of the induction regimen are separated from the prior dose by one, two or three days.

8. The method of any one of embodiments 3 to 7, wherein the induction regimen comprises administering CER-001 to the subject for at least 3 weeks.

9. The method of embodiment 8, wherein the induction regimen comprises administering CER-001 to the subject for 3 weeks.

10. The method of any one of embodiments 4 to 9, wherein the consolidation regimen comprises administering at least two doses of CER-001 to the subject in one week.

11. The method of any one of embodiments 4 to 10, wherein the doses of the consolidation regimen are separated by no more than four days.

12. The method of any one of embodiments 4 to 11, wherein the second and subsequent doses of the consolidation regimen are separated from the prior dose by three or four days.

13. The method of any one of embodiments 4 to 12, wherein the consolidation regimen comprises administering CER-001 to the subject for at least 3 weeks.

14. The method of embodiment 13, wherein the consolidation regimen comprises administering CER-001 to the subject for 3 weeks.

15. The method of any one of embodiments 2 to 14, wherein the doses of the maintenance regimen are administered once every 5 or more days.

16. The method of any one of embodiments 2 to 14, wherein the doses of the maintenance regimen are administered weekly.

17. The method of embodiment 16, wherein the doses of the maintenance regimen are administered +/−2 days around the strict weekly date.

18. The method of any one of embodiments 2 to 14, wherein the doses of the maintenance regimen are administered twice weekly.

19. The method of any one of embodiments 3 to 18, wherein the induction regimen comprises administering three or more doses of CER-001 to the subject.

20. The method of any one of embodiments 3 to 18, wherein the induction regimen comprises administering four or more doses of CER-001 to the subject.

21. The method of any one of embodiments 3 to 18, wherein the induction regimen comprises administering five or more doses of CER-001 to the subject.

22. The method of any one of embodiments 3 to 18, wherein the induction regimen comprises administering six or more doses of CER-001 to the subject.

23. The method of any one of embodiments 3 to 18, wherein the induction regimen comprises administering seven or more doses of CER-001 to the subject.

24. The method of any one of embodiments 3 to 18, wherein the induction regimen comprises administering eight or more doses of CER-001 to the subject.

25. The method of any one of embodiments 3 to 18, wherein the induction regimen comprises administering nine or more doses of CER-001 to the subject.

26. The method of embodiment 25, wherein the induction regimen comprises administering nine doses of CER-001 to the subject.

27. The method of embodiment 26, wherein the induction regimen comprises administering the first dose of CER-001 to the subject on day 1 and administering subsequent doses of the induction regimen to the subject on days 2, 4, 7, 9, 11, 14, 16, and 18.

28. The method of any one of embodiments 3 to 18, wherein the induction regimen comprises administering ten or more doses of CER-001 to the subject.

29. The method of any one of embodiments 4 to 28, wherein the consolidation regimen comprises administering three or more doses of CER-001 to the subject.

30. The method of any one of embodiments 4 to 28, wherein the consolidation regimen comprises administering four or more doses of CER-001 to the subject.

31. The method of any one of embodiments 4 to 28, wherein the consolidation regimen comprises administering five or more doses of CER-001 to the subject.

32. The method of any one of embodiments 4 to 28, wherein the consolidation regimen comprises administering six or more doses of CER-001 to the subject.

33. The method of embodiment 32, wherein the consolidation regimen comprises administering six doses of CER-001 to the subject.

34. The method of embodiment 33, wherein the consolidation regimen comprises administering the six doses of CER-001 to the subject on days 21, 24, 28, 31, 35, and 38 following an induction regimen which begins on day 1.

35. The method of any one of embodiments 4 to 28, wherein the consolidation regimen comprises administering seven or more doses of CER-001 to the subject.

36. The method of any one of embodiments 4 to 28, wherein the consolidation regimen comprises administering eight or more doses of CER-001 to the subject.

37. The method of any one of embodiments 4 to 28, wherein the consolidation regimen comprises administering nine or more doses of CER-001 to the subject.

38. The method of any one of embodiments 4 to 28, wherein the consolidation regimen comprises administering ten or more doses of CER-001 to the subject.

39. The method of any one of embodiments 2 to 38, wherein the maintenance regimen comprises administering CER-001 to the subject for at least one month.

40. The method of any one of embodiments 2 to 38, wherein the maintenance regimen comprises administering CER-001 to the subject for at least two months.

41. The method of any one of embodiments 2 to 38, wherein the maintenance regimen comprises administering CER-001 to the subject for at least three months.

42. The method of any one of embodiments 2 to 38, wherein the maintenance regimen comprises administering CER-001 to the subject for least six months.

43. The method of any one of embodiments v, wherein the maintenance regimen comprises administering CER-001 to the subject for at least nine months.

44. The method of any one of embodiments 2 to 38, wherein the maintenance regimen comprises administering CER-001 to the subject for at least a year.

45. The method of any one of embodiments 2 to 38, wherein the maintenance regimen comprises administering CER-001 to the subject for at least 18 months.

46. The method of any one of embodiments 2 to 38, wherein the maintenance regimen comprises administering CER-001 to the subject for at least 2 years.

47. The method of any one of embodiments 2 to 38, wherein the maintenance regimen comprises administering CER-001 to the subject indefinitely.

48. The method of any one of embodiments 2 to 38, wherein the maintenance regimen comprises administering CER-001 for 16 or more weeks.

49. The method of any one of embodiments 2 to 38, wherein the maintenance regimen comprises administering CER-001 for 20 or more weeks.

50. The method of any one of embodiments 2 to 38, wherein the maintenance regimen comprises administering CER-001 for 30 or more weeks.

51. The method of any one of embodiments 2 to 38, wherein the maintenance regimen comprises administering CER-001 for 40 or more weeks.

52. The method of any one of embodiments 3 to 51, wherein the dose of CER-001 administered in the induction regimen is 4 to 30 mg/kg (on a protein weight basis).

53. The method of embodiment 52, wherein the dose of CER-001 administered in the induction regimen is 5 to 15 mg/kg (on a protein weight basis).

54. The method of embodiment 52, wherein the dose of CER-001 administered in the induction regimen is 10 to 20 mg/kg (on a protein weight basis).

55. The method of embodiment 52, wherein the dose of CER-001 administered in the induction regimen is 15 to 25 mg/kg (on a protein weight basis).

56. The method of embodiment 52, wherein the dose of CER-001 administered in the induction regimen is 8 mg/kg (on a protein weight basis).

57. The method of embodiment 52, wherein the dose of CER-001 administered in the induction regimen is 10 mg/kg (on a protein weight basis).

58. The method of any one of embodiments 3 to 51, wherein the dose of CER-001 administered in the induction regimen is 300 mg to 3000 mg.

59. The method of embodiment 58, wherein the dose of CER-001 administered in the induction regimen is 300 mg to 1500 mg.

60. The method of embodiment 58, wherein the dose of CER-001 administered in the induction regimen is 400 mg to 1500 mg.

61. The method of embodiment 58, wherein the dose of CER-001 administered in the induction regimen is 500 mg to 1200 mg.

62. The method of embodiment 58, wherein the dose of CER-001 administered in the induction regimen is 500 mg to 1000 mg.

63. The method of any one of embodiments 4 to 62, wherein the dose of CER-001 administered in the consolidation regimen is 4 to 30 mg/kg (on a protein weight basis).

64. The method of embodiment 63, wherein the dose of CER-001 administered in the consolidation regimen is 5 to 15 mg/kg (on a protein weight basis).

65. The method of embodiment 63, wherein the dose of CER-001 administered in the consolidation regimen is 10 to 20 mg/kg (on a protein weight basis).

66. The method of embodiment 63, wherein the dose of CER-001 administered in the consolidation regimen is 15 to 25 mg/kg (on a protein weight basis).

67. The method of embodiment 63, wherein the dose of CER-001 administered in the consolidation regimen is 8 mg/kg (on a protein weight basis).

68. The method of embodiment 63, wherein the dose of CER-001 administered in the consolidation regimen is 10 mg/kg (on a protein weight basis).

69. The method of any one of embodiments 4 to 62, wherein the dose of CER-001 administered in the consolidation regimen is 300 mg to 3000 mg.

70. The method of embodiment 69, wherein the dose of CER-001 administered in the consolidation regimen is 300 mg to 1500 mg.

71. The method of embodiment 69, wherein the dose of CER-001 administered in the consolidation regimen is 400 mg to 1500 mg.

72. The method of embodiment 69, wherein the dose of CER-001 administered in the consolidation regimen is 500 mg to 1200 mg.

73. The method of embodiment 69, wherein the dose of CER-001 administered in the consolidation regimen is 500 mg to 1000 mg.

74. The method of any one of embodiments 2 to 73, wherein the dose of CER-001 administered in the maintenance regimen is 4 to 30 mg/kg (on a protein weight basis).

75. The method of embodiment 74, wherein the dose of CER-001 administered in the maintenance regimen is 5 to 15 mg/kg (on a protein weight basis).

76. The method of embodiment 74, wherein the dose of CER-001 administered in the maintenance regimen is 10 to 20 mg/kg (on a protein weight basis).

77. The method of embodiment 74, wherein the dose of CER-001 administered in the maintenance regimen is 15 to 25 mg/kg (on a protein weight basis).

78. The method embodiment 74, wherein the dose of CER-001 administered in the maintenance regimen is 8 mg/kg (on a protein weight basis).

79. The method embodiment 74, wherein the dose of CER-001 administered in the maintenance regimen is 10 mg/kg (on a protein weight basis).

80. The method embodiment 74, wherein the dose of CER-001 administered in the maintenance regimen is 20 mg/kg (on a protein weight basis).

81. The method of any one of embodiments 2 to 73, wherein the dose of CER-001 administered in the maintenance regimen is 300 mg to 3000 mg.

82. The method embodiment 81, wherein the dose of CER-001 administered in the maintenance regimen is 300 mg to 1500 mg.

83. The method of embodiment 81, wherein the dose of CER-001 administered in the maintenance regimen is 400 mg to 1500 mg.

84. The method of embodiment 81, wherein the dose of CER-001 administered in the maintenance regimen is 500 mg to 1200 mg.

85. The method of embodiment 81, wherein the dose of CER-001 administered in the maintenance regimen is 500 mg to 1000 mg.

86. The method of any one of embodiments 1 to 85, wherein the CER-001 is administered by infusion.

87. The method of any one of embodiments 3 to 86, wherein the dose of CER-001 administered in the induction regimen and the dose of CER-001 administered in the maintenance regimen are the same.

88. The method of any one of embodiments 3 to 86, wherein the dose of CER-001 administered in the induction regimen and the dose of CER-001 administered in the maintenance regimen are different.

89. The method of embodiment 88, wherein the dose of CER-001 administered in the maintenance regimen is greater than the dose of CER-001 administered in the induction regimen.

90. The method of embodiment 89, wherein the dose of CER-001 administered in the maintenance regimen is 1.5 to 3 times the dose of CER-001 administered in the induction regimen.

91. The method of embodiment 90, wherein the dose of CER-001 administered in the maintenance regimen is 2 times the dose administered in the induction regimen.

92. The method of any one of embodiments 89 to 91, wherein CER-001 is administered by infusion and the duration of each infusion of CER-001 during the maintenance regimen is longer than the duration of each infusion of CER-001 during the consolidation regimen.

93. The method of embodiment 92, wherein the duration of each infusion of CER-001 during the maintenance regimen is twice as long as the duration of each infusion of CER-001 during the consolidation regimen.

94. The method of any one of embodiments 4 to 93, wherein the dose of CER-001 administered in the consolidation regimen and the dose of CER-001 administered in the maintenance regimen are the same.

95. The method of any one of embodiments 4 to 93, wherein the dose of CER-001 administered in the consolidation regimen and the dose of CER-001 administered in the maintenance regimen are different.

96. The method of embodiment 95, wherein the dose of CER-001 administered in the maintenance regimen is greater than the dose administered in the consolidation regimen.

97. The method of embodiment 96, wherein the dose of CER-001 administered in the maintenance regimen is 1.5 to 3 times the dose of CER-001 administered in the consolidation regimen.

98. The method of embodiment 97, wherein the dose of CER-001 administered in the maintenance regimen is 2 times the dose administered in the consolidation regimen.

99. The method of any one of embodiments 96 to 98, wherein CER-001 is administered by infusion and the duration of each infusion of CER-001 during the maintenance regimen is longer than the duration of each infusion of CER-001 during the consolidation regimen.

100. The method of embodiment 99, wherein the duration of each infusion of CER-001 during the maintenance regimen is twice as long as the duration of each infusion of CER-001 during the consolidation regimen.

101. The method of any one of embodiments 1 to 100, wherein the subject has glomerulopathy.

102. The method of any one of embodiments 1 to 101, wherein the subject has an LCAT deficiency.

103. The method of embodiment 102, wherein the subject has a cholesteryl ester (CE) to total cholesterol (TC) ratio of 60% or less.

104. The method of embodiment 102, wherein the subject has a cholesteryl ester (CE) to total cholesterol (TC) ratio of 0% to 60%.

105. The method of embodiment 102, wherein the subject has a cholesteryl ester (CE) to total cholesterol (TC) ratio of 0% to 50%.

106. The method of embodiment 102, wherein the subject has a cholesteryl ester (CE) to total cholesterol (TC) ratio of 0% to 25%.

107. The method of embodiment 102, wherein the subject has a cholesteryl ester (CE) to total cholesterol (TC) ratio of 25% to 60%.

108. The method of embodiment 102, wherein the subject has a cholesteryl ester (CE) to total cholesterol (TC) ratio of 25% to 50%.

109. The method of any one of embodiments 102 to 108, wherein the subject has a plasma LCAT concentration of 0 µg/ml to 4 µg/ml.

110. The method of any one of embodiments 102 to 108, wherein the subject has a plasma LCAT concentration of 0 µg/ml to 3 µg/ml.

111. The method of any one of embodiments 102 to 108, wherein the subject has a plasma LCAT concentration of 0 µg/ml to 2 µg/ml.

112. The method of any one of embodiments 102 to 108, wherein the subject has a plasma LCAT concentration of 1 µg/ml to 4 µg/ml.

113. The method of any one of embodiments 102 to 108, wherein the subject has a plasma LCAT concentration of 1 µg/ml to 3 µg/ml.

114. The method of any one of embodiments 102 to 113, wherein the LCAT deficiency is an acquired LCAT deficiency.

115. The method of embodiment 114, wherein the LCAT deficiency is not due to an LCAT mutation.

116. The method of any one of embodiments 1 to 113, wherein the subject has an LCAT mutation.

117. The method of embodiment 116, wherein the subject is homozygous for an LCAT mutation.

118. The method of embodiment 116, wherein the subject is heterozygous for an LCAT mutation.

119. The method of any one of embodiments 1 to 118, wherein the subject has diabetic nephropathy.

120. The method of any one of embodiments 1 to 119, wherein the subject has chronic kidney disease (CKD).

121. The method of any one of embodiments 1 to 120, wherein the subject has liver disease.

122. The method of embodiment 121, wherein the subject has chronic liver disease. 123. The method of embodiment 121, wherein the wherein the subject has alcoholic liver disease.

124. The method of any one of embodiments 1 to 123, wherein the subject is at risk of hepatorenal syndrome (HRS).

125. The method of embodiment 124, wherein the therapeutically effective amount of CER-001 is an amount effective to prevent HRS.

126. The method of embodiment 124, wherein the therapeutically effective amount of CER-001 is an amount effective to delay the onset of HRS and/or reduce the severity of HRS.

127. The method of any one of embodiments 1 to 123, wherein the subject has hepatorenal syndrome (HRS).

128. The method of embodiment 127, wherein the HRS is type 1 HRS. 129. The method of embodiment 127, wherein the HRS is type 2 HRS. 130. The method of any one of embodiments 1 to 129, wherein the subject is undergoing kidney dialysis.

131. The method of any one of embodiments 1 to 129, wherein the subject is not undergoing kidney dialysis.

132. The method of embodiment 131, wherein the treatment delays the subject's need for kidney dialysis.

133. The method of any one of embodiments 1 to 132, wherein the subject has undergone a kidney transplant.

134. The method of any one of embodiments 1 to 132, wherein the subject has not undergone a kidney transplant.

135. The method of any one of embodiments 1 to 134, wherein the treatment delays the subject's need for a kidney transplant.

136. The method of any one of embodiments 1 to 135, wherein an antihistamine is administered prior to administration of one or more of the CER-001 doses.

137. The method of any one of embodiments 1 to 136, wherein the subject is also treated with a lipid control medication.

138. The method of embodiment 137, wherein the lipid control medication comprises a statin.

139. The method of embodiment 139, wherein the statin is atorvastatin, rosuvastatin, simvastatin, fluvastatin, lovastatin, or pravastatin.

140. The method of any one of embodiments 137 to 139, wherein the lipid control medication comprises a cholesterol absorption inhibitor.

141. The method of embodiment 140, wherein the cholesterol absorption inhibitor is ezetimibe.

142. The method of any one of embodiments 137 to 141, wherein the lipid control medication comprises niacin.

143. The method of any one of embodiments 137 to 142, wherein the lipid control medication comprises aspirin.

144. The method of any one of embodiments 137 to 143, wherein the lipid control medication comprises a proprotein convertase subtilisin/kexin type 9 (PCSK9) inhibitor.

145. The method of embodiment 144, wherein the PCSK9 inhibitor is an antibody. 146. The method of embodiment 145, wherein the antibody is alirocumab, bococizumabevolocumab, 1D05-IgG2 or LY3015014.

147. The method of embodiment 144, wherein the PCSK9 inhibitor is RNAi therapeutic.

148. The method of embodiment 147, wherein the RNAi therapeutic is ALN-PCSSC. 149. The method of any one of embodiments 137 to 148, further comprising administering a therapeutically effective amount of the lipid control medication to the subject.

150. A method for treating a subject with kidney disease, comprising administering to the subject a therapeutically effective amount of CER-001, optionally according to a dosing regimen which comprises:
  (a) an induction regimen; and/or
  (b) a consolidation regimen; and/or
  (c) a maintenance regimen.

151. The method of embodiment 150, which comprises administering one or more doses of CER-001 according to an induction regimen.

152. The method of embodiment 151, wherein the induction regimen comprises administering multiple doses of CER-001 to the subject.

153. The method of embodiment 152, wherein the induction regimen comprises administering at least three doses of CER-001 to the subject.

154. The method of embodiment 152 or embodiment 153, in which multiple doses in the induction regimen are separated by 1 or more days.

155. The method of any one any one of embodiments 150 to 154, wherein the doses following the initial dose of the induction regimen are separated by no more than 3 days.

156. The method of embodiment 155, wherein the doses following the initial dose of the induction regimen are separated by one to three days.

157. The method of embodiment 155, wherein the doses following the initial dose of the induction regimen are separated by two to three days.

158. The method of embodiment 155, wherein the doses following the initial dose of the induction regimen are separated by one to two days.

159. The method of any one of embodiments 150 to 158, wherein the induction regimen is for a duration of at least one week.

160. The method of embodiment 159, wherein the induction regimen is for a duration of two weeks.

161. The method of embodiment 159, wherein the induction regimen is for a duration of three weeks.

162. The method of any one of embodiments 150 to 161, in which the induction regimen comprises administering to the subject three doses of CER-001 per week.

163. The method of any one of embodiments 150 to 162, wherein the induction regimen comprises administering four or more doses of CER-001 to the subject.

164. The method of any one of embodiments 150 to 162, wherein the induction regimen comprises administering five or more doses of CER-001 to the subject.

165. The method of any one of embodiments 150 to 162, wherein the induction regimen comprises administering six or more doses of CER-001 to the subject.

166. The method of any one of embodiments 150 to 162, wherein the induction regimen comprises administering seven or more doses of CER-001 to the subject.

167. The method of any one of embodiments 150 to 162, wherein the induction regimen comprises administering eight or more doses of CER-001 to the subject.

168. The method of any one of embodiments 150 to 162, wherein the induction regimen comprises administering nine or more doses of CER-001 to the subject.

169. The method of embodiment 168, wherein the induction regimen comprises administering the first dose of CER-001 to the subject on day 1 and administering subsequent doses of the induction regimen to the subject on days 2, 4, 7, 9, 11, 14, 16, and 18.

170. The method of any one of embodiments 150 to 162, wherein the induction regimen comprises administering ten or more doses of CER-001 to the subject.

171. The method of any one of embodiments 150 to 170, which comprises administering to the subject one or more doses of CER-001 according to a consolidation regimen.

172. The method of embodiment 171, wherein the consolidation regimen comprises administering multiple doses of CER-001 to the subject.

173. The method of embodiment 172, in which multiple doses in the consolidation regimen are separated by 2 or more days.

174. The method of any one of embodiments 171 to 173, wherein the consolidation regimen comprises administering at least two doses of CER-001 to the subject in one week.

175. The method of any one of embodiments 171 to 174, wherein the doses of the consolidation regimen are separated by no more than four days.

176. The method of any one of embodiments 171 to 175, wherein the doses of the consolidation regimen are separated from one another by three or four days.

177. The method of any one of embodiments 171 to 176, wherein the consolidation regimen is for a duration of at least 3 weeks.

178. The method of any one of embodiments 171 to 177, wherein the consolidation regimen comprises administering three or more doses of CER-001 to the subject.

179. The method of any one of embodiments 171 to 177, wherein the consolidation regimen comprises administering four or more doses of CER-001 to the subject.

180. The method of any one of embodiments 171 to 177, wherein the consolidation regimen comprises administering five or more doses of CER-001 to the subject.

181. The method of any one of embodiments 171 to 177, wherein the consolidation regimen comprises administering six or more doses of CER-001 to the subject.

182. The method of embodiment 181, wherein the consolidation regimen comprises administering six doses of CER-001 to the subject.

183. The method of embodiment 182, wherein the consolidation regimen comprises administering the six doses of CER-001 to the subject on days 21, 24, 28, 31, 35, and 38 following an induction regimen which begins on day 1.

184. The method of any one of embodiments 171 to 177, wherein the consolidation regimen comprises administering seven or more doses of CER-001 to the subject.

185. The method of any one of embodiments 171 to 177, wherein the consolidation regimen comprises administering eight or more doses of CER-001 to the subject.

186. The method of any one of embodiments 171 to 177, wherein the consolidation regimen comprises administering nine or more doses of CER-001 to the subject.

187. The method of any one of embodiments 171 to 177, wherein the consolidation regimen comprises administering ten or more doses of CER-001 to the subject.

188. The method of any one of embodiments 150 to 187, which comprises administering to the subject multiple doses of CER-001 according to a maintenance regimen.

189. The method of embodiment 188, wherein the maintenance regimen comprises administering a dose of CER-001 to the subject once every 3 or more days.

190. The method of embodiment 188, wherein the maintenance regimen comprises administering a dose of CER-001 to the subject once every 5 or more days.

191. The method of embodiment 188, wherein the maintenance regimen comprises administering a dose of CER-001 to the subject weekly.

192. The method of embodiment 191, wherein the doses of the maintenance regimen are administered +/−2 days around the strict weekly date.

193. The method of embodiment 188, wherein the maintenance regimen comprises administering a dose of CER-001 to the subject twice weekly.

194. The method of any one of embodiments 188 to 193, wherein the maintenance regimen comprises administering CER-001 to the subject for at least one month.

195. The method of any one of embodiments 188 to 193, wherein the maintenance regimen comprises administering CER-001 to the subject for at least two months.

196. The method of any one of embodiments 188 to 193, wherein the maintenance regimen comprises administering CER-001 to the subject for at least three months.

197. The method of any one of embodiments 188 to 193, wherein the maintenance regimen comprises administering CER-001 to the subject for at least six months.

198. The method of any one of embodiments 188 to 193, wherein the maintenance regimen comprises administering CER-001 to the subject for at least nine months.

199. The method of any one of embodiments 188 to 193, wherein the maintenance regimen comprises administering CER-001 to the subject for at least a year.

200. The method of any one of embodiments 188 to 193, wherein the maintenance regimen comprises administering CER-001 to the subject for at least 18 months.

201. The method of any one of embodiments 188 to 193, wherein the maintenance regimen comprises administering CER-001 to the subject for at least 2 years.

202. The method of any one of embodiments 188 to 193, wherein the maintenance regimen comprises administering CER-001 to the subject indefinitely.

203. The method of any one of embodiments 188 to 193, wherein the maintenance regimen comprises administering CER-001 to the subject for 16 or more weeks.

204. The method of any one of embodiments 188 to 193, wherein the maintenance regimen comprises administering CER-001 to the subject for 20 or more weeks.

205. The method of any one of embodiments 188 to 193, wherein the maintenance regimen comprises administering CER-001 to the subject for 30 or more weeks.

206. The method of any one of embodiments 188 to 193, wherein the maintenance regimen comprises administering CER-001 to the subject for 40 or more weeks.

207. The method of any one of embodiments 150 to 206, wherein the dose of CER-001 administered in the induction regimen is 4 to 30 mg/kg (on a protein weight basis).

208. The method of any one of embodiments 150 to 206, wherein the dose of CER-001 administered in the induction regimen is 5 to 15 mg/kg (on a protein weight basis).

209. The method of any one of embodiments 150 to 206, wherein the dose of CER-001 administered in the induction regimen is 10 to 20 mg/kg (on a protein weight basis).

210. The method of any one of embodiments 150 to 206, wherein the dose of CER-001 administered in the induction regimen is 15 to 25 mg/kg (on a protein weight basis).

211. The method of any one of embodiments 150 to 206, wherein the dose of CER-001 administered in the induction regimen is 8 mg/kg (on a protein weight basis).

212. The method of any one of embodiments 150 to 206, wherein the dose of CER-001 administered in the induction regimen is 10 mg/kg (on a protein weight basis).

213. The method of any one of embodiments 150 to 206, wherein the dose of CER-001 administered in the induction regimen is 300 mg to 3000 mg.

214. The method of any one of embodiments 150 to 206, wherein the dose of CER-001 administered in the induction regimen is 300 mg to 1500 mg.

215. The method of any one of embodiments 150 to 206, wherein the dose of CER-001 administered in the induction regimen is 400 mg to 1500 mg.

216. The method of any one of embodiments 150 to 206, wherein the dose of CER-001 administered in the induction regimen is 500 mg to 1200 mg.

217. The method of any one of embodiments 150 to 206, wherein the dose of CER-001 administered in the induction regimen is 500 mg to 1000 mg.

218. The method of any one of embodiments 150 to 217, wherein the dose of CER-001 administered in the consolidation regimen is 4 to 30 mg/kg (on a protein weight basis).

219. The method of any one of embodiments 150 to 217, wherein the dose of CER-001 administered in the consolidation regimen is 5 to 15 mg/kg (on a protein weight basis).

220. The method of any one of embodiments 150 to 217, wherein the dose of CER-001 administered in the consolidation regimen is 10 to 20 mg/kg (on a protein weight basis).

221. The method of any one of embodiments 150 to 217, wherein the dose of CER-001 administered in the consolidation regimen is 15 to 25 mg/kg (on a protein weight basis).

222. The method of any one of embodiments 150 to 217, wherein the dose of CER-001 administered in the consolidation regimen is 8 mg/kg (on a protein weight basis).

223. The method of any one of embodiments 150 to 217, wherein the dose of CER-001 administered in the consolidation regimen is 10 mg/kg (on a protein weight basis).

224. The method of any one of embodiments 150 to 217, wherein the dose of CER-001 administered in the consolidation regimen is 300 mg to 3000 mg.

225. The method of any one of embodiments 150 to 217, wherein the dose of CER-001 administered in the consolidation regimen is 300 mg to 1500 mg.

226. The method of any one of embodiments 150 to 217, wherein the dose of CER-001 administered in the consolidation regimen is 400 mg to 1500 mg.

227. The method of any one of embodiments 150 to 217, wherein the dose of CER-001 administered in the consolidation regimen is 500 mg to 1200 mg.

228. The method of any one of embodiments 150 to 217, wherein the dose of CER-001 administered in the consolidation regimen is 500 mg to 1000 mg.

229. The method of any one of embodiments 150 to 228, wherein the dose of CER-001 administered in the maintenance regimen is 4 to 30 mg/kg (on a protein weight basis).

230. The method of any one of embodiments 150 to 228, wherein the dose of CER-001 administered in the maintenance regimen is 5 to 15 mg/kg (on a protein weight basis).

231. The method of any one of embodiments 150 to 228, wherein the dose of CER-001 administered in the maintenance regimen is 10 to 20 mg/kg (on a protein weight basis).

232. The method of any one of embodiments 150 to 228, wherein the dose of CER-001 administered in the maintenance regimen is 15 to 25 mg/kg (on a protein weight basis).

233. The method of any one of embodiments 150 to 228, wherein the dose of CER-001 administered in the maintenance regimen is 8 mg/kg (on a protein weight basis).

234. The method of any one of embodiments 150 to 228, wherein the dose of CER-001 administered in the maintenance regimen is 10 mg/kg (on a protein weight basis).

235. The method of any one of embodiments 150 to 228, wherein the dose of CER-001 administered in the maintenance regimen is 20 mg/kg (on a protein weight basis).

236. The method of any one of embodiments 150 to 228, wherein the dose of CER-001 administered in the maintenance regimen is 300 mg to 3000 mg.

237. The method of any one of embodiments 150 to 228, wherein the dose of CER-001 administered in the maintenance regimen is 300 mg to 1500 mg.

238. The method of any one of embodiments 150 to 228, wherein the dose of CER-001 administered in the maintenance regimen is 400 mg to 1500 mg.

239. The method of any one of embodiments 150 to 228, wherein the dose of CER-001 administered in the maintenance regimen is 500 mg to 1200 mg.

240. The method of any one of embodiments 150 to 228, wherein the dose of CER-001 administered in the maintenance regimen is 500 mg to 1000 mg.

241. The method of any one of embodiments 150 to 240, which comprises a maintenance regimen and wherein the dose of CER-001 administered in the maintenance regimen is administered by infusion.

242. The method of any one of embodiments 150 to 241, which comprises both an induction regimen and a maintenance regimen.

243. The method of embodiment 242, wherein the dose of CER-001 administered in the induction regimen and the dose of CER-001 administered in the maintenance regimen are the same.

244. The method of embodiment 242, wherein the dose of CER-001 administered in the induction regimen and the dose of CER-001 administered in the maintenance regimen are different.

245. The method of embodiment 244, wherein the dose of CER-001 administered in the maintenance regimen is greater than the dose of CER-001 administered in the induction regimen.

246. The method of embodiment 245, wherein the dose of CER-001 administered in the maintenance regimen is 1.5 to 3 times the dose of CER-001 administered in the induction regimen.

247. The method of embodiment 245, wherein the dose of CER-001 administered in the maintenance regimen is 2 times the dose administered in the induction regimen.

248. The method of any one of embodiments 150 to 247, which comprises both a consolidation regimen and a maintenance regimen.

249. The method of embodiment 248, wherein CER-001 is administered by infusion. 250. The method of embodiment 249, wherein the duration of each infusion of CER-001 during the maintenance regimen is longer than the duration of each infusion of CER-001 during the consolidation regimen.

251. The method of embodiment 250, wherein the duration of each infusion of CER-001 during the maintenance regimen is twice as long as the duration of each infusion of CER-001 during the consolidation regimen.

252. The method of any one of embodiments 248 to 251, wherein the dose of CER-001 administered in the consolidation regimen and the dose of CER-001 administered in the maintenance regimen are the same.

253. The method of any one of embodiments 248 to 251, wherein the dose of CER-001 administered in the consolidation regimen and the dose of CER-001 administered in the maintenance regimen are different.

254. The method of embodiment 253, wherein the dose of CER-001 administered in the maintenance regimen is greater than the dose administered in the consolidation regimen.

255. The method of embodiment 253, wherein the dose of CER-001 administered in the maintenance regimen is 1.5 to 3 times the dose of CER-001 administered in the consolidation regimen.

256. The method of embodiment 253, wherein the dose of CER-001 administered in the maintenance regimen is 2 times the dose administered in the consolidation regimen.

257. The method of any one of embodiments 150 to 256, wherein the subject has glomerulopathy.

258. The method of any one of embodiments 150 to 257, wherein the subject has an LCAT deficiency 259. The method of embodiment 258, wherein the subject has a cholesteryl ester (CE) to total cholesterol (TC) ratio of 60% or less.

260. The method of embodiment 258, wherein the subject has a cholesteryl ester (CE) to total cholesterol (TC) ratio of 0% to 60%.

261. The method of embodiment 258, wherein the subject has a cholesteryl ester (CE) to total cholesterol (TC) ratio of 0% to 50%.

262. The method of embodiment 258, wherein the subject has a cholesteryl ester (CE) to total cholesterol (TC) ratio of 0% to 25%.

263. The method of embodiment 258, wherein the subject has a cholesteryl ester (CE) to total cholesterol (TC) ratio of 25% to 60%.

264. The method of embodiment 258, wherein the subject has a cholesteryl ester (CE) to total cholesterol (TC) ratio of 25% to 50%.

265. The method of any one of embodiments 258 to 264, wherein the subject has a plasma LCAT concentration of 0 µg/ml to 4 µg/ml.

266. The method of any one of embodiments 258 to 264, wherein the subject has a plasma LCAT concentration of 0 µg/ml to 3 µg/ml.

267. The method of any one of embodiments 258 to 264, wherein the subject has a plasma LCAT concentration of 0 µg/ml to 2 µg/ml.

268. The method of any one of embodiments 258 to 264, wherein the subject has a plasma LCAT concentration of 1 µg/ml to 4 µg/ml.

269. The method of any one of embodiments 258 to 264, wherein the subject has a plasma LCAT concentration of 1 µg/ml to 3 µg/ml.

270. The method of any one of embodiments 258 to 269, wherein the LCAT deficiency is an acquired LCAT deficiency.

271. The method of embodiment 270, wherein the LCAT deficiency is not due to an LCAT mutation 272. The method of any one of embodiments 150 to 269, wherein the subject has an LCAT mutation.

273. The method of embodiment 272, wherein the subject is homozygous for an LCAT mutation.

274. The method of embodiment 272, wherein the subject is heterozygous for an LCAT mutation.

275. The method of any one of embodiments 150 to 274, wherein the subject has diabetic nephropathy.

276. The method of any one of embodiments 150 to 275, wherein the subject has chronic kidney disease (CKD).

277. The method of any one of embodiments 150 to 276, wherein the subject has liver disease.

278. The method of embodiment 277, wherein the subject has chronic liver disease.

279. The method of embodiment 277, wherein the wherein the subject has alcoholic liver disease.

280. The method of any one of embodiments 150 to 279, wherein the subject is at risk of hepatorenal syndrome (HRS).

281. The method of embodiment 280, wherein the therapeutically effective amount of CER-001 is an amount effective to prevent HRS.

282. The method of embodiment 280, wherein the therapeutically effective amount of CER-001 is an amount effective to delay the onset of HRS and/or reduce the severity of HRS.

283. The method of any one of embodiments 150 to 279, wherein the subject has hepatorenal syndrome (HRS).

284. The method of embodiment 283, wherein the HRS is type 1 HRS.

285. The method of embodiment 283, wherein the HRS is type 2 HRS.

286. The method of any one of embodiments 150 to 285, wherein the subject is undergoing hemodialysis.

287. The method of any one of embodiments 150 to 285, wherein the subject is a candidate for hemodialysis.

288. The method of embodiment 287, wherein the treatment delays the subject's need to initiate hemodialysis.

289. The method of any one of embodiments 150 to 288, wherein the subject has undergone a kidney transplant.

290. The method of any one of embodiments 150 to 288, wherein the subject has not undergone a kidney transplant.

291. The method of any one of embodiments 150 to 290, wherein the treatment delays the subject's need for a kidney transplant.

292. The method of any one of embodiments 150 to 291, wherein an antihistamine is administered prior to administration of one or more of the CER-001 doses.

293. The method of any one of embodiments 150 to 292, wherein the subject is also treated with a lipid control medication.

294. The method of embodiment 293, wherein the lipid control medication comprises a statin.

295. The method of embodiment 294, wherein the statin is atorvastatin, rosuvastatin, simvastatin, fluvastatin, lovastatin, or pravastatin.

296. The method of any one of embodiments 293 to 295, wherein the lipid control medication comprises a cholesterol absorption inhibitor.

297. The method of embodiment 296, wherein the cholesterol absorption inhibitor is ezetimibe.

298. The method of any one of embodiments 293 to 297, wherein the lipid control medication comprises niacin.

299. The method of any one of embodiments 293 to 298, wherein the lipid control medication comprises aspirin.

300. The method of any one of embodiments 293 to 299, wherein the lipid control medication comprises a proprotein convertase subtilisin/kexin type 9 (PCSK9) inhibitor.

301. The method of embodiment 300, wherein the PCSK9 inhibitor is an antibody.

302. The method of embodiment 301, wherein the antibody is alirocumab, bococizumabevolocumab, 1D05-IgG2 or LY3015014.

303. The method of embodiment 300, wherein the PCSK9 inhibitor is RNAi therapeutic.

304. The method of embodiment 303, wherein the RNAi therapeutic is ALN-PCSSC.

305. The method of any one of embodiments 293 to 304, further comprising administering a therapeutically effective amount of the lipid control medication to the subject.

306. A method for treating a subject with kidney disease, comprising administering to the subject a therapeutically effective amount of CER-001, optionally according to a dosing regimen which comprises:
(a) an induction regimen; and/or
(b) a consolidation regimen; and/or
(c) a maintenance regimen.

307. The method of embodiment 306, which comprises administering one or more doses of CER-001 according to an induction regimen.

308. The method of embodiment 307, wherein the induction regimen comprises administering multiple doses of CER-001 to the subject.

309. The method of embodiment 308, wherein the induction regimen comprises administering at least three doses of CER-001 to the subject.

310. The method of embodiment 308 or embodiment 309, in which multiple doses in the induction regimen are separated by 1 or more days.

311. The method of any one any one of embodiments 306 to 310, wherein the doses following the initial dose of the induction regimen are separated by no more than 3 days.

312. The method of embodiment 311, wherein the doses following the initial dose of the induction regimen are separated by one to three days.

313. The method of embodiment 311, wherein the doses following the initial dose of the induction regimen are separated by two to three days.

314. The method of embodiment 311, wherein the doses following the initial dose of the induction regimen are separated by one to two days.

315. The method of any one of embodiments 306 to 314, wherein the induction regimen is for a duration of at least one week.

316. The method of embodiment 315, wherein the induction regimen is for a duration of two weeks.

317. The method of embodiment 315, wherein the induction regimen is for a duration of three weeks.

318. The method of any one of embodiments 306 to 317, in which the induction regimen comprises administering to the subject three doses of CER-001 per week.

319. The method of any one of embodiments 306 to 318, wherein the induction regimen comprises administering four or more doses of CER-001 to the subject.

320. The method of any one of embodiments 306 to 318, wherein the induction regimen comprises administering five or more doses of CER-001 to the subject.

321. The method of any one of embodiments 306 to 318, wherein the induction regimen comprises administering six or more doses of CER-001 to the subject.

322. The method of any one of embodiments 306 to 318, wherein the induction regimen comprises administering seven or more doses of CER-001 to the subject.

323. The method of any one of embodiments 306 to 318, wherein the induction regimen comprises administering eight or more doses of CER-001 to the subject.

324. The method of any one of embodiments 306 to 318, wherein the induction regimen comprises administering nine or more doses of CER-001 to the subject.

325. The method of embodiment 324, wherein the induction regimen comprises administering the first dose of CER-001 to the subject on day 1 and administering subsequent doses of the induction regimen to the subject on days 2, 4, 7, 9, 11, 14, 16, and 18.

326. The method of any one of embodiments 306 to 318, wherein the induction regimen comprises administering ten or more doses of CER-001 to the subject.

327. The method of any one of embodiments 306 to 326, which comprises administering to the subject one or more doses of CER-001 according to a consolidation regimen.

328. The method of embodiment 327, wherein the consolidation regimen comprises administering multiple doses of CER-001 to the subject.

329. The method of embodiment 328, in which multiple doses in the consolidation regimen are separated by 2 or more days.

330. The method of any one of embodiments 327 to 329, wherein the consolidation regimen comprises administering at least two doses of CER-001 to the subject in one week.

331. The method of any one of embodiments 327 to 330, wherein the doses of the consolidation regimen are separated by no more than four days.

332. The method of any one of embodiments 327 to 331, wherein the doses of the consolidation regimen are separated from one another by three or four days.

333. The method of any one of embodiments 327 to 332, wherein the consolidation regimen is for a duration of at least 3 weeks.

334. The method of any one of embodiments 327 to 333, wherein the consolidation regimen comprises administering three or more doses of CER-001 to the subject.

335. The method of any one of embodiments 327 to 333, wherein the consolidation regimen comprises administering four or more doses of CER-001 to the subject.

336. The method of any one of embodiments 327 to 333, wherein the consolidation regimen comprises administering five or more doses of CER-001 to the subject.

337. The method of any one of embodiments 327 to 333, wherein the consolidation regimen comprises administering six or more doses of CER-001 to the subject.

338. The method of embodiment 337, wherein the consolidation regimen comprises administering six doses of CER-001 to the subject.

339. The method of embodiment 338, wherein the consolidation regimen comprises administering the six doses of CER-001 to the subject on days 21, 24, 28, 31, 35, and 38 following an induction regimen which begins on day 1.

340. The method of any one of embodiments 327 to 333, wherein the consolidation regimen comprises administering seven or more doses of CER-001 to the subject.

341. The method of any one of embodiments 327 to 333, wherein the consolidation regimen comprises administering eight or more doses of CER-001 to the subject.

342. The method of any one of embodiments 327 to 333, wherein the consolidation regimen comprises administering nine or more doses of CER-001 to the subject.

343. The method of any one of embodiments 327 to 333, wherein the consolidation regimen comprises administering ten or more doses of CER-001 to the subject.

344. The method of any one of embodiments 306 to 343, which comprises administering to the subject multiple doses of CER-001 according to a maintenance regimen.

345. The method of embodiment 344, wherein the maintenance regimen comprises administering a dose of CER-001 to the subject once every 3 or more days.

346. The method of embodiment 344, wherein the maintenance regimen comprises administering a dose of CER-001 to the subject once every 5 or more days.

347. The method of embodiment 344, wherein the maintenance regimen comprises administering a dose of CER-001 to the subject weekly.

348. The method of embodiment 347, wherein the doses of the maintenance regimen are administered +/−2 days around the strict weekly date.

349. The method of embodiment 344, wherein the maintenance regimen comprises administering a dose of CER-001 to the subject twice weekly.

350. The method of any one of embodiments 344 to 349, wherein the maintenance regimen comprises administering CER-001 to the subject for at least one month.

351. The method of any one of embodiments 344 to 349, wherein the maintenance regimen comprises administering CER-001 to the subject for at least two months.

352. The method of any one of embodiments 344 to 349, wherein the maintenance regimen comprises administering CER-001 to the subject for at least three months.

353. The method of any one of embodiments 344 to 349, wherein the maintenance regimen comprises administering CER-001 to the subject for at least six months.

354. The method of any one of embodiments v, wherein the maintenance regimen comprises administering CER-001 to the subject for at least nine months.

355. The method of any one of embodiments 344 to 349, wherein the maintenance regimen comprises administering CER-001 to the subject for at least a year.

356. The method of any one of embodiments 344 to 349, wherein the maintenance regimen comprises administering CER-001 to the subject for at least 18 months.

357. The method of any one of embodiments 344 to 349, wherein the maintenance regimen comprises administering CER-001 to the subject for at least 2 years.

358. The method of any one of embodiments 344 to 349, wherein the maintenance regimen comprises administering CER-001 to the subject indefinitely.

359. The method of any one of embodiments 344 to 349, wherein the maintenance regimen comprises administering CER-001 to the subject for 16 or more weeks.

360. The method of any one of embodiments 344 to 349, wherein the maintenance regimen comprises administering CER-001 to the subject for 20 or more weeks.

361. The method of any one of embodiments 344 to 349, wherein the maintenance regimen comprises administering CER-001 to the subject for 30 or more weeks.

362. The method of any one of embodiments 344 to 349, wherein the maintenance regimen comprises administering CER-001 to the subject for 40 or more weeks.

363. The method of any one of embodiments 306 to 362, wherein the dose of CER-001 administered in the induction regimen is 4 to 30 mg/kg (on a protein weight basis).

364. The method of any one of embodiments 306 to 362, wherein the dose of CER-001 administered in the induction regimen is 5 to 15 mg/kg (on a protein weight basis).

365. The method of any one of embodiments 306 to 362, wherein the dose of CER-001 administered in the induction regimen is 10 to 20 mg/kg (on a protein weight basis).

366. The method of any one of embodiments 306 to 362, wherein the dose of CER-001 administered in the induction regimen is 15 to 25 mg/kg (on a protein weight basis).

367. The method of any one of embodiments 306 to 362, wherein the dose of CER-001 administered in the induction regimen is 8 mg/kg (on a protein weight basis).

368. The method of any one of embodiments 306 to 362, wherein the dose of CER-001 administered in the induction regimen is 10 mg/kg (on a protein weight basis).

369. The method of any one of embodiments 306 to 362, wherein the dose of CER-001 administered in the induction regimen is 300 mg to 3000 mg.

370. The method of any one of embodiments 306 to 362, wherein the dose of CER-001 administered in the induction regimen is 300 mg to 1500 mg.

371. The method of any one of embodiments 306 to 362, wherein the dose of CER-001 administered in the induction regimen is 400 mg to 1500 mg.

372. The method of any one of embodiments 306 to 362, wherein the dose of CER-001 administered in the induction regimen is 500 mg to 1200 mg.

373. The method of any one of embodiments 306 to 362, wherein the dose of CER-001 administered in the induction regimen is 500 mg to 1000 mg.

374. The method of any one of embodiments 306 to 373, wherein the dose of CER-001 administered in the consolidation regimen is 4 to 30 mg/kg (on a protein weight basis).

375. The method of any one of embodiments 306 to 373, wherein the dose of CER-001 administered in the consolidation regimen is 5 to 15 mg/kg (on a protein weight basis).

376. The method of any one of embodiments 306 to 373, wherein the dose of CER-001 administered in the consolidation regimen is 10 to 20 mg/kg (on a protein weight basis).

377. The method of any one of embodiments 306 to 373, wherein the dose of CER-001 administered in the consolidation regimen is 15 to 25 mg/kg (on a protein weight basis).

378. The method of any one of embodiments 306 to 373, wherein the dose of CER-001 administered in the consolidation regimen is 8 mg/kg (on a protein weight basis).

379. The method of any one of embodiments 306 to 373, wherein the dose of CER-001 administered in the consolidation regimen is 10 mg/kg (on a protein weight basis).

380. The method of any one of embodiments 306 to 373, wherein the dose of CER-001 administered in the consolidation regimen is 300 mg to 3000 mg.

381. The method of any one of embodiments 306 to 373, wherein the dose of CER-001 administered in the consolidation regimen is 300 mg to 1500 mg.

382. The method of any one of embodiments 306 to 373, wherein the dose of CER-001 administered in the consolidation regimen is 400 mg to 1500 mg.

383. The method of any one of embodiments 306 to 373, wherein the dose of CER-001 administered in the consolidation regimen is 500 mg to 1200 mg.

384. The method of any one of embodiments 306 to 373, wherein the dose of CER-001 administered in the consolidation regimen is 500 mg to 1000 mg.

385. The method of any one of embodiments 306 to 384, wherein the dose of CER-001 administered in the maintenance regimen is 4 to 30 mg/kg (on a protein weight basis).

386. The method of any one of embodiments 306 to 384, wherein the dose of CER-001 administered in the maintenance regimen is 5 to 15 mg/kg (on a protein weight basis).

387. The method of any one of embodiments 306 to 384, wherein the dose of CER-001 administered in the maintenance regimen is 10 to 20 mg/kg (on a protein weight basis).

388. The method of any one of embodiments 306 to 384, wherein the dose of CER-001 administered in the maintenance regimen is 15 to 25 mg/kg (on a protein weight basis).

389. The method of any one of embodiments 306 to 384, wherein the dose of CER-001 administered in the maintenance regimen is 8 mg/kg (on a protein weight basis).

390. The method of any one of embodiments 306 to 384, wherein the dose of CER-001 administered in the maintenance regimen is 10 mg/kg (on a protein weight basis).

391. The method of any one of embodiments 306 to 384, wherein the dose of CER-001 administered in the maintenance regimen is 20 mg/kg (on a protein weight basis).

392. The method of any one of embodiments 306 to 384, wherein the dose of CER-001 administered in the maintenance regimen is 300 mg to 3000 mg.

393. The method of any one of embodiments 306 to 384, wherein the dose of CER-001 administered in the maintenance regimen is 300 mg to 1500 mg.

394. The method of any one of embodiments 306 to 384, wherein the dose of CER-001 administered in the maintenance regimen is 400 mg to 1500 mg.

395. The method of any one of embodiments 306 to 384, wherein the dose of CER-001 administered in the maintenance regimen is 500 mg to 1200 mg.

396. The method of any one of embodiments 306 to 384, wherein the dose of CER-001 administered in the maintenance regimen is 500 mg to 1000 mg.

397. The method of any one of embodiments 306 to 396, which comprises a maintenance regimen and wherein the dose of CER-001 administered in the maintenance regimen is administered by infusion.

398. The method of any one of embodiments 306 to 397, which comprises both an induction regimen and a maintenance regimen.

399. The method of embodiment 398, wherein the dose of CER-001 administered in the induction regimen and the dose of CER-001 administered in the maintenance regimen are the same.

400. The method of embodiment 398, wherein the dose of CER-001 administered in the induction regimen and the dose of CER-001 administered in the maintenance regimen are different.

401. The method of embodiment 400, wherein the dose of CER-001 administered in the maintenance regimen is greater than the dose of CER-001 administered in the induction regimen.

402. The method of embodiment 401, wherein the dose of CER-001 administered in the maintenance regimen is 1.5 to 3 times the dose of CER-001 administered in the induction regimen.

403. The method of embodiment 401, wherein the dose of CER-001 administered in the maintenance regimen is 2 times the dose administered in the induction regimen.

404. The method of any one of embodiments 306 to 403, which comprises both a consolidation regimen and a maintenance regimen.

405. The method of embodiment 404, wherein CER-001 is administered by infusion.

406. The method of embodiment 405, wherein the duration of each infusion of CER-001 during the maintenance regimen is longer than the duration of each infusion of CER-001 during the consolidation regimen.

407. The method of embodiment 406, wherein the duration of each infusion of CER-001 during the maintenance regimen is twice as long as the duration of each infusion of CER-001 during the consolidation regimen.

408. The method of any one of embodiments 404 to 407, wherein the dose of CER-001 administered in the consolidation regimen and the dose of CER-001 administered in the maintenance regimen are the same.

409. The method of any one of embodiments 404 to 407, wherein the dose of CER-001 administered in the consolidation regimen and the dose of CER-001 administered in the maintenance regimen are different.

410. The method of embodiment 409, wherein the dose of CER-001 administered in the maintenance regimen is greater than the dose administered in the consolidation regimen.

411. The method of embodiment 409, wherein the dose of CER-001 administered in the maintenance regimen is 1.5 to 3 times the dose of CER-001 administered in the consolidation regimen.

412. The method of embodiment 409, wherein the dose of CER-001 administered in the maintenance regimen is 2 times the dose administered in the consolidation regimen.

413. The method of any one of embodiments 306 to 412, wherein the subject has glomerulopathy.

414. The method of any one of embodiments 306 to 413, wherein the subject has an LCAT deficiency.

415. The method of embodiment 414, wherein the subject has a cholesteryl ester (CE) to total cholesterol (TC) ratio of 60% or less.

416. The method of embodiment 414, wherein the subject has a cholesteryl ester (CE) to total cholesterol (TC) ratio of 0% to 60%.

417. The method of embodiment 414, wherein the subject has a cholesteryl ester (CE) to total cholesterol (TC) ratio of 0% to 50%.

418. The method of embodiment 414, wherein the subject has a cholesteryl ester (CE) to total cholesterol (TC) ratio of 0% to 25%.

419. The method of embodiment 414, wherein the subject has a cholesteryl ester (CE) to total cholesterol (TC) ratio of 25% to 60%.

420. The method of embodiment 414, wherein the subject has a cholesteryl ester (CE) to total cholesterol (TC) ratio of 25% to 50%.

421. The method of any one of embodiments 414 to 420, wherein the subject has a plasma LCAT concentration of 0 μg/ml to 4 μg/ml.

422. The method of any one of embodiments 414 to 420, wherein the subject has a plasma LCAT concentration of 0 μg/ml to 3 μg/ml.

423. The method of any one of embodiments 414 to 420, wherein the subject has a plasma LCAT concentration of 0 μg/ml to 2 μg/ml.

424. The method of any one of embodiments 414 to 420, wherein the subject has a plasma LCAT concentration of 1 μg/ml to 4 μg/ml.

425. The method of any one of embodiments 414 to 420, wherein the subject has a plasma LCAT concentration of 1 μg/ml to 3 μg/ml.

426. The method of any one of embodiments 414 to 425, wherein the LCAT deficiency is an acquired LCAT deficiency.

427. The method of embodiment 426, wherein the LCAT deficiency is not due to an LCAT mutation.

428. The method of any one of embodiments 306 to 425, wherein the subject has an LCAT mutation.

429. The method of embodiment 428, wherein the subject is homozygous for an LCAT mutation.

430. The method of embodiment 428, wherein the subject is heterozygous for an LCAT mutation.

431. The method of any one of embodiments 306 to 430, wherein the subject has diabetic nephropathy.

432. The method of any one of embodiments 306 to 431, wherein the subject has chronic kidney disease (CKD).

433. The method of any one of embodiments 306 to 432, wherein the subject has liver disease.

434. The method of embodiment 433, wherein the subject has chronic liver disease. 435. The method of embodiment 433, wherein the wherein the subject has alcoholic liver disease.

436. The method of any one of embodiments 306 to 435, wherein the subject is at risk of hepatorenal syndrome (HRS).

437. The method of embodiment 436, wherein the therapeutically effective amount of CER-001 is an amount effective to prevent HRS.

438. The method of embodiment 436, wherein the therapeutically effective amount of CER-001 is an amount effective to delay the onset of HRS and/or reduce the severity of HRS.

439. The method of any one of embodiments 306 to 435, wherein the subject has hepatorenal syndrome.

440. The method of embodiment 439, wherein the HRS is type 1 HRS.

441. The method of embodiment 439, wherein the HRS is type 2 HRS.

442. The method of any one of embodiments 306 to 441, wherein the subject is undergoing hemodialysis.

443. The method of any one of embodiments 306 to 441, wherein the subject is a candidate for hemodialysis.

444. The method of embodiment 443, wherein the treatment delays the subject's need to initiate hemodialysis.

445. The method of any one of embodiments 306 to 444, wherein the subject has undergone a kidney transplant.

446. The method of any one of embodiments 306 to 444, wherein the subject has not undergone a kidney transplant.

447. The method of any one of embodiments 306 to 446, wherein the treatment delays the subject's need for a kidney transplant.

448. The method of any one of embodiments 306 to 447, wherein an antihistamine is administered prior to administration of one or more of the CER-001 doses.

449. The method of any one of embodiments 306 to 448, wherein the subject is also treated with a lipid control medication.

450. The method of embodiment 449, wherein the lipid control medication comprises a statin.

451. The method of embodiment 450, wherein the statin is atorvastatin, rosuvastatin, simvastatin, fluvastatin, lovastatin, or pravastatin.

452. The method of any one of embodiments 449 to 451, wherein the lipid control medication comprises a cholesterol absorption inhibitor.

453. The method of embodiment 452, wherein the cholesterol absorption inhibitor is ezetimibe.

454. The method of any one of embodiments 449 to 453, wherein the lipid control medication comprises niacin.

455. The method of any one of embodiments 449 to 454, wherein the lipid control medication comprises aspirin.

456. The method of any one of embodiments 449 to 455, wherein the lipid control medication comprises a proprotein convertase subtilisin/kexin type 9 (PCSK9) inhibitor.

457. The method of embodiment 456, wherein the PCSK9 inhibitor is an antibody.

458. The method of embodiment 457, wherein the antibody is alirocumab, bococizumabevolocumab, 1D05-IgG2 or LY3015014.

459. The method of embodiment 456, wherein the PCSK9 inhibitor is RNAi therapeutic.

460. The method of embodiment 459, wherein the RNAi therapeutic is ALN-PCSSC.

461. The method of any one of embodiments 449 to 460, further comprising administering a therapeutically effective amount of the lipid control medication to the subject.

462. The method of any one of embodiments 1 to 461, wherein the CER-001 is a lipoprotein complex comprising ApoA-I and phospholipids in a ApoA-I weight:total phospholipid weight ratio of 1:2.7+/−20% and the phospholipids sphingomyelin and DPPG in a sphingomyelin:DPPG weight:weight ratio of 97:3+/−20%.

463. The method of any one of embodiments 1 to 461, wherein the CER-001 is a lipoprotein complex comprising ApoA-I and phospholipids in a ApoA-I weight:total phospholipid weight ratio of 1:2.7+/−10% and the phospholipids sphingomyelin and DPPG in a sphingomyelin:DPPG weight:weight ratio of 97:3+/−10%.

464. The method of any one of embodiments 1 to 461, wherein the CER-001 is a lipoprotein complex comprising ApoA-I and phospholipids in a ApoA-I weight:total phospholipid weight ratio of 1:2.7 and the phospholipids sphingomyelin and DPPG in a sphingomyelin:DPPG weight:weight ratio of 97:3.

465. The method of any one of embodiments 462 to 464, wherein the ApoA-I has the amino acid sequence of amino acids 25-267 of SEQ ID NO:1 of WO 2012/109162.

466. The method of any one of embodiments 393 to 396, wherein the ApoA-I is recombinantly expressed.

467. The method of any one of embodiments 462 to 466, wherein the CER-001 comprises natural sphingomyelin.

468. The method of embodiment 467, wherein the natural sphingomyelin is chicken egg sphingomyelin.

469. The method of any one of embodiments 462 to 466, wherein the CER-001 comprises synthetic sphingomyelin.

470. The method of embodiment 469, wherein the synthetic sphingomyelin is palmitoylsphingomyelin.

471. The method of any one of embodiments 1 to 470, wherein CER-001 is administered in the form of a formulation in which the CER-001 is at least 95% homogeneous.

472. The method of embodiment 471, wherein CER-001 is administered in the form of a formulation in which the CER-001 is at least 97% homogeneous.

473. The method of embodiment 471, wherein CER-001 is administered in the form of a formulation in which the CER-001 is at least 98% homogeneous.

474. The method of embodiment 471, wherein CER-001 is administered in the form of a formulation in which the CER-001 is at least 99% homogeneous.

While various specific embodiments have been illustrated and described, it will be appreciated that various changes can be made without departing from the spirit and scope of the disclosure(s).

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

What is claimed is:

1. A method for treating a subject with glomerulopathy, kidney disease associated with lecithin cholesterol acyl transferase (LCAT) deficiency, diabetic nephropathy, chronic kidney disease (CKD), or hepatorenal syndrome (HRS), comprising:
   (a) administering CER-001 to the subject according to an induction regimen comprising administering at least three doses of CER-001 to the subject separated by 1 to 3 days; and, subsequently
   (b) administering CER-001 to the subject according to a consolidation regimen comprising administering at least two doses of CER-001 to the subject separated by 2 to 4 days; and, subsequently
   (c) administering CER-001 to the subject according to a maintenance regimen comprising administering a dose of CER-001 to the subject once every 3 days to weekly.

2. The method of claim 1, wherein the induction regimen comprises administering nine doses of CER-001 to the subject over 3 weeks, the consolidation regimen comprises administering six doses of CER-001 to the subject over 3 weeks, and the maintenance regimen comprises administering CER-001 to the subject weekly.

3. The method of claim 1, wherein the dose of CER-001 administered in the induction regimen is 4 to 30 mg/kg (on a protein weight basis).

4. The method of claim 3, wherein the dose of CER-001 administered in the induction regimen is 10 mg/kg (on a protein weight basis).

5. The method of claim 1, wherein the dose of CER-001 administered in the consolidation regimen is 4 to 30 mg/kg (on a protein weight basis).

6. The method of claim 5, wherein the dose of CER-001 administered in the consolidation regimen is 10 mg/kg (on a protein weight basis).

7. The method claim 1, wherein the dose of CER-001 administered in the maintenance regimen is 10 mg/kg or 20 mg/kg (on a protein weight basis).

8. The method of claim 1, wherein the CER-001 is administered by infusion.

9. The method of claim 1, wherein the subject is undergoing kidney dialysis.

10. The method of claim 1, wherein the subject is not undergoing kidney dialysis.

11. The method of claim 10, wherein the treatment delays the subject's need for kidney dialysis.

12. The method of claim 1, wherein the subject has not undergone a kidney transplant.

13. The method of claim 12, wherein the treatment delays the subject's need for a kidney transplant.

* * * * *